(12) United States Patent
Li et al.

(10) Patent No.: US 11,753,652 B2
(45) Date of Patent: Sep. 12, 2023

(54) CASSETTE ENCODING A FPV/BRACHYURY FUSION PROTEIN

(71) Applicant: Bavarian Nordic A/S, Kvistgaard (DK)

(72) Inventors: Zengji Li, San Ramon, CA (US); Alain Delcayre, San Jose, CA (US); Ryan Rountree, San Mateo, CA (US)

(73) Assignee: Bavarian Nordic A/S, Hellerup (DK)

( * ) Notice: Subject to any disclaimer, the term of this patent is extended or adjusted under 35 U.S.C. 154(b) by 0 days.

(21) Appl. No.: 15/747,844

(22) PCT Filed: Jul. 28, 2016

(86) PCT No.: PCT/IB2016/001183
§ 371 (c)(1),
(2) Date: Jan. 26, 2018

(87) PCT Pub. No.: WO2017/021776
PCT Pub. Date: Feb. 9, 2017

(65) Prior Publication Data
US 2018/0216134 A1 Aug. 2, 2018

Related U.S. Application Data

(60) Provisional application No. 62/199,681, filed on Jul. 31, 2015.

(51) Int. Cl.
C12N 15/00 (2006.01)
C12N 15/86 (2006.01)
C12Q 1/6897 (2018.01)
C07K 14/435 (2006.01)

(52) U.S. Cl.
CPC ............ C12N 15/86 (2013.01); C07K 14/435 (2013.01); C12Q 1/6897 (2013.01); C12N 2710/24043 (2013.01); C12N 2830/15 (2013.01)

(58) Field of Classification Search
CPC ................. C12N 15/86; C12N 2710/24043
See application file for complete search history.

(56) References Cited

U.S. PATENT DOCUMENTS 5,670,367 A 9/1997 Dorner
7,638,134 B2 12/2009 Panicali et al.

FOREIGN PATENT DOCUMENTS

| CN | 101775410 | 7/2010 |
| CN | 102321637 | 1/2012 |
| RU | 2180352 | 3/2002 |
| WO | 2005/038028 | 4/2005 |
| WO | WO 2008/106551 | 9/2008 |
| WO | WO 2010/121180 | 10/2010 |
| WO | WO 2014/043535 | 3/2014 |

OTHER PUBLICATIONS

Jenks, Trends in Comparative Endocrinology and Neurobiology, 2009. Ann. N. Y. Acad. Sci. vol. 1163, pp. 17-30.*
Dickmeis, Briefings in Functional Genomics and Proteomics, 2005. vol. 3, No. 4, pp. 332-350.*
Wang et al. Nucleic Acids Research, 2009. vol. 37, No. 8, pp. 2618-2629.*
Poole et al. Gene, 2001. vol. 269, pp. 1-12.*
Li et al. Accession No. AYG87016, 2010.*
Written Opinion and Search Report of the International Search Authority for PCT/IB2016/001183, dated Feb. 9, 2017.
Zantinge et al., Partial transcriptional mapping of the fowlpox virus genome and analysis of the Eco RI L fragment, Journal of General Virology, 77: 603-614 (1996).
Hamilton et al., "Aberrant expression of the embryonic transcription factor brachyury in human tumors detected with a novel rabbit monoclonal antibody," Oncotarget, 2014, pp. 4853-4862, vol. 6.
Roselli et al., "Brachyury, a driver of the epithelial-mesenchymal transition, is overexpressed in human lung tumors: an opportunity for novel interventions against lung cancer," Clin. Cancer Res., 2012, pp. 3868-3879, vol. 18.

* cited by examiner

Primary Examiner — Michael C Wilson

(57) ABSTRACT

The present invention relates to one or more promoters and/or expression cassettes that can be used for enhancing expression of a heterologous gene, such as Brachury. In particular, the one or more promoters and/or expression cassettes enhance expression of heterologous genes as part of a viral vector, such as a poxvirus.

7 Claims, 6 Drawing Sheets

Specification includes a Sequence Listing.

Expression of Brachyury in human DCs

Expression of Brachyury and TRICOM in CMMT cells

Figure 6

Expression of Brachyury and TRICOM from FPV-mBN345B

SEQUENCE LISTING

```
<160> NUMBER OF SEQ ID NOS: 77

<210> SEQ ID NO 1
<211> LENGTH: 167
<212> TYPE: DNA
<213> ORGANISM: Artificial Sequence
<220> FEATURE:
<223> OTHER INFORMATION: Promoter Sequence with nucleotides 5' of Gene
      FPV 088

<400> SEQUENCE: 1
tatccgtaca ggtttgtttc tgaaattcac tttgtaagat acataattaa caaattcagg      60
gggaaaaatc tttacaaaat tagtatagaa gctatagata tatcaaaagg tagacaacaa     120
ataatcagaa cctaattttt ttatcaaaaa attaaaatat aaataaa                   167

<210> SEQ ID NO 2
<211> LENGTH: 170
<212> TYPE: DNA
<213> ORGANISM: Artificial Sequence
<220> FEATURE:
<223> OTHER INFORMATION: Promoter Sequence with nucleotides 5' of Gene
      FPV 088 + atc sequence

<400> SEQUENCE: 2
tatccgtaca ggtttgtttc tgaaattcac tttgtaagat acataattaa caaattcagg      60
gggaaaaatc tttacaaaat tagtatagaa gctatagata tatcaaaagg tagacaacaa     120
ataatcagaa cctaattttt ttatcaaaaa attaaaatat aaataaaatc                170

<210> SEQ ID NO 3
<211> LENGTH: 183
<212> TYPE: DNA
<213> ORGANISM: Artificial Sequence
<220> FEATURE:
<223> OTHER INFORMATION: Promoter Sequence with nucleotides 5' of Gene
      FPV 088 plus addition of 16 nucleotides of FPV 088

<400> SEQUENCE: 3
tatccgtaca ggtttgtttc tgaaattcac tttgtaagat acataattaa caaattcagg      60
gggaaaaatc tttacaaaat tagtatagaa gctatagata tatcaaaagg tagacaacaa     120
ataatcagaa cctaattttt ttatcaaaaa attaaaatat aaataaaatg aaaaataact     180
tgt                                                                   183

<210> SEQ ID NO 4
<211> LENGTH: 194
<212> TYPE: DNA
```

<213> ORGANISM: Artificial Sequence
<220> FEATURE:
<223> OTHER INFORMATION: Promoter Sequence with region from Gene FPV 088
    plus addition of 27 nucleotides

<400> SEQUENCE: 4

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaa                                                      194
```

<210> SEQ ID NO 5
<211> LENGTH: 200
<212> TYPE: DNA
<213> ORGANISM: Artificial Sequence
<220> FEATURE:
<223> OTHER INFORMATION: Promoter Sequence with region from Gene FPV 088
    plus addition of 33 nucleotides

<400> SEQUENCE: 5

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaaatgaac                                                200
```

<210> SEQ ID NO 6
<211> LENGTH: 212
<212> TYPE: DNA
<213> ORGANISM: Artificial Sequence
<220> FEATURE:
<223> OTHER INFORMATION: Promoter Sequence with region from Gene FPV 088
    plus addition of 45 nucleotides

<400> SEQUENCE: 6

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaaatgaac atgagtaaga aa                                  212
```

<210> SEQ ID NO 7
<211> LENGTH: 232
<212> TYPE: DNA
<213> ORGANISM: Artificial Sequence
<220> FEATURE:
<223> OTHER INFORMATION: Promoter Sequence with region from Gene FPV 088
    plus addition of 65 nucleotides

<400> SEQUENCE: 7

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaaatgaac atgagtaaga acaagtaaaa aactcaaagt aa            232
```

<210> SEQ ID NO 8
<211> LENGTH: 242
<212> TYPE: DNA
<213> ORGANISM: Artificial Sequence
<220> FEATURE:
<223> OTHER INFORMATION: Promoter Sequence with region from Gene FPV 088 plus addition of 75 nucleotides

<400> SEQUENCE: 8

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaatgaac atgagtaaga aacaagtaaa aactcaaagt aaatgtaata    240
at                                                                  242
```

<210> SEQ ID NO 9
<211> LENGTH: 245
<212> TYPE: DNA
<213> ORGANISM: Artificial Sequence
<220> FEATURE:
<223> OTHER INFORMATION: Promoter Sequence with region from Gene FPV 088
    plus addition of 78 nucleotides

<400> SEQUENCE: 9

```
tatccgtaca ggtttgtttc tgaaattcac tttgtaagat acataattaa caaattcagg    60
gggaaaaatc tttacaaaat tagtatagaa gctatagata tatcaaaagg tagacaacaa   120
ataatcagaa cctaattttt ttatcaaaaa attaaaatat aaataaaatg aaaaataact   180
tgtatgaaga aaaatga Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
            195                 200                 205

Lys Tyr Asn Pro Phe Ala Lys Ala Phe Leu Asp Ala Lys Glu Arg Ser
        210                 215                 220

Asp His Lys Glu Met Met Glu Glu Pro Gly Asp Ser Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Gln Tyr Pro Ser Leu Trp Ser
            340                 345                 350

Val Ser Asn Gly Ala Val Thr Pro Gly Ser Gln Ala Ala Val Ser
        355                 360                 365

Asn Gly Leu Gly Ala Gln Phe Phe Arg Gly Ser Pro Ala His Tyr Thr
370                 375                 380

Pro Leu Thr His Pro Val Ser Ala Pro Ser Ser Ser Gly Ser Pro Leu
385                 390                 395                 400

Tyr Glu Gly Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
            420                 425                 430

Pro Ser Met
        435

<210> SEQ ID NO 12
<211> LENGTH: 1308
<212> TYPE: DNA
<213> ORGANISM: Artificial Sequence
<220> FEATURE:
<223> OTHER INFORMATION: Coding sequence for Brachyury protein Isoform 1
      GenBank Accession No. O15178.1

<400> SEQUENCE: 12
atgagctccc ctggcaccga gagcgcggga aagagcctgc agtaccgagt ggaccacctg    60

-continued

```
ctgagcgccg tggagaatga gctgcaggcg ggcagcgaga agggcgaccc cacagagcgc    120
gaactgcgcg tgggcctgga ggagagcgag ctgtggctgc gcttcaagga gctcaccaat    180
gagatgatcg tgaccaagaa cggcaggagg atgtttccgg tgctgaaggt gaacgtgtct    240
ggcctggacc ccaacgccat gtactccttc ctgctggact cgtggcggc ggacaaccac    300 cgctggaagt acgtgaacgg ggaatgggtg ccggggggca agccggagcc gcaggcgccc    360
agctgcgtct acatccaccc cgactcgccc aacttcgggg cccactggat gaaggctccc    420
gtctccttca gcaaagtcaa gctcaccaac aagctcaacg agggggccca gatcatgctg    480
aactccttgc ataagtatga gcctcgaatc cacatagtga gagttggggg tccacagcgc    540
atgatcacca gccactgctt ccctgagacc cagttcatag cggtgactgc ttatcagaac    600
gaggagatca cagctcttaa aattaagtac aatccatttg caaaagcttt ccttgatgca    660
aaggaaagaa gtgatcacaa agagatgatg aggaacccg gagacagcca gcaacctggg    720
tactcccaat gggggtggct tcttcctgga accagcaccc tgtgtccacc tgcaaatcct    780
catcctcagt ttggaggtgc cctctccctc ccctccacgc acagctgtga caggtaccca    840
accctgagga gccaccggtc ctcaccctac cccagcccct atgctcatcg aacaattct    900 ccaacctatt ctgacaactc acctgcatgt ttatccatgc tgcaatccca tgacaattgg    960
tccagccttg gaatgcctgc ccatcccagc atgctccccg tgagccacaa tgccagccca   1020
cctaccagct ccagtcagta ccccagcctg tggtctgtga gcaacggcgc cgtcaccccg   1080
ggctcccagg cagcagccgt gtccaacggg ctgggggccc agttcttccg gggctccccc   1140
gcgcactaca caccccctcac ccatccggtc tcggcgcccct cttcctcggg atcccccactg   1200 tacgaagggg cggccgcggc cacagacatc gtggacagcc agtacgacgc cgcagcccaa   1260
ggccgcctca tagcctcatg gacacctgtg tcgccacctt ccatgtga                 1308
```

<210> SEQ ID NO 13
<211> LENGTH: 435
<212> TYPE: PRT
<213> ORGANISM: Artificial Sequence
<220> FEATURE:
<223> OTHER INFORMATION: Brachyury protein Isoform 1 (L254V)

<400> SEQUENCE: 13

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140
```

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
            165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Val Cys Pro
            245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
            325                 330                 335

Asn Ala Ser Pro Pro Thr Ser Ser Ser Gln Tyr Pro Ser Leu Trp Ser
            340                 345                 350

Val Ser Asn Gly Ala Val Thr Pro Gly Ser Gln Ala Ala Ala Val Ser
        355                 360                 365

Asn Gly Leu Gly Ala Gln Phe Phe Arg Gly Ser Pro Ala His Tyr Thr
        370                 375                 380

Pro Leu Thr His Pro Val Ser Ala Pro Ser Ser Gly Ser Pro Leu
385                 390                 395                 400

Tyr Glu Gly Ala Ala Ala Ala Thr Asp Ile Val Asp Ser Gln Tyr Asp
            405                 410                 415

Ala Ala Ala Gln Gly Arg Leu Ile Ala Ser Trp Thr Pro Val Ser Pro
            420                 425                 430

Pro Ser Met
        435

```
<210> SEQ ID NO 14
<211> LENGTH: 1308
<212> TYPE: DNA
<213> ORGANISM: Artificial Sequence
<220> FEATURE:
<223> OTHER INFORMATION: Coding sequence encoding Brachyury protein
      Isoform 1 with L254V

<400> SEQUENCE: 14
atgagctccc ctggcaccga gagcgcggga aagagcctgc agtaccgagt ggaccacctg    60
ctgagcgccg tggagaatga gctgcaggcg ggcagcgaga agggcgaccc cacagagcgc    120
gaactgcgcg tgggcctgga ggagagcgag ctgtggctgc gcttcaagga gctcaccaat    180
gagatgatcg tgaccaagaa cggcaggagg atgtttccgg tgctgaaggt gaacgtgtct    240
ggcctggacc ccaacgccat gtactccttc ctgctggact cgtggcggc ggacaaccac    300 cgctggaagt acgtgaacgg ggaatggtg ccgggggca agccggagcc gcaggcgccc    360
```

```
agctgcgtct acatccaccc cgactcgccc aacttcgggg cccactggat gaaggctccc    420
gtctccttca gcaaagtcaa gctcaccaac aagctcaacg gagggggcca gatcatgctg    480
aactccttgc ataagtatga gcctcgaatc cacatagtga gagttggggg tccacagcgc    540
atgatcacca gccactgctt ccctgagacc cagttcatag cggtgactgc ttatcagaac    600
gaggagatca cagctcttaa aattaagtac aatccatttg caaaggcttt ccttgatgca    660
aaggaaagaa gtgatcacaa agagatgatg gaggaacccg gagacagcca gcaacctggg    720
tactcccaat gggggtggct tcttcctgga accagcaccg tttgtccacc tgcaaatcct    780
catcctcagt ttggaggtgc cctctccctc ccctccacgc acagctgtga caggtaccca    840
accctgagga gccaccggtc ctcaccctac cccagcccct atgctcatcg gaacaattct    900
ccaacctatt ctgacaactc acctgcatgt ttatccatgc tgcaatccca tgacaattgg    960
tccagccttg aatgcctgcc catcccagca tgctccccg tgagccacaa tgccagccca    1020
cctaccagct ccagtcagta ccccagcctg tggtctgtga gcaacggcgc cgtcaccccg    1080
ggctcccagg cagcagccgt gtccaacggg ctggggccc agttcttccg gggctccccc    1140
gcgcactaca caccccctcac ccatccggtc tcggcgccct cttcctcggg atccccactg    1200
tacgaagggg cggccgcggc cacagacatc gtggacagcc agtacgacgc cgcagcccaa    1260
ggccgcctca tagcctcatg gacacctgtg tcgccacctt ccatgtga                 1308
```

<210> SEQ ID NO 15
<211> LENGTH: 1305
<212> TYPE: DNA
<213> ORGANISM: Artificial Sequence
<220> FEATURE:
<223> OTHER INFORMATION: Coding sequence encoding Brachyury protein
      Isoform 1 with L254V without 5' atg sequence

<400> SEQUENCE: 15

```
agctcccctg gcaccgagag cgcgggaaag agcctgcagt accgagtgga ccacctgctg    60
agcgccgtgg agaatgagct gcaggcgggc agcgagaagg gcgaccccac agagcgcgaa    120
ctgcgcgtgg gcctggagga gagcgagctg tggctgcgct tcaaggagct caccaatgag    180
atgatcgtga ccaagaacgg caggaggatg tttccggtgc tgaaggtgaa cgtgtctggc    240
ctggacccca cgccatgta ctccttcctg ctggacttcg tggcggcgga caaccaccgc    300
tggaagtacg tgaacgggga tgggtgccg ggggcaagc cggagccgca ggcgcccagc    360
tgcgtctaca tccaccccga ctcgcccaac ttcgggccc actggatgaa ggctcccgtc    420
tccttcagca agtcaagct caccaacaag ctcaacggag ggggccagat catgctgaac    480
tccttgcata gtatgagcc tcgaatccac atagtgagag ttgggggtcc acagcgcatg    540
atcaccagcc actgcttccc tgagacccag ttcatagcgg tgactgctta tcagaacgag    600
gagatcacag ctcttaaaat taagtacaat ccatttgcaa aggctttcct tgatgcaaag    660
gaaagaagtg atcacaaaga gatgatggag gaacccggag acagccagca acctgggtac    720
tcccaatggg ggtggcttct tcctggaacc agcaccgttt gtccacctgc aaatcctcat    780
cctcagtttg gaggtgccct ctccctcccc tccacgcaca gctgtgacag gtacccaacc    840
ctgaggagcc accggtcctc accctacccc agcccctatg ctcatcggaa caattctcca    900
acctattctg acaactcacc tgcatgttta tccatgctgc aatcccatga caattggtcc    960
agccttggaa tgcctgccca tcccagcatg ctccccgtga gccacaatgc cagcccacct    1020
accagctcca gtcagtaccc cagcctgtgg tctgtgagca acggcgccgt caccccgggc    1080
```

```
tcccaggcag cagccgtgtc caacgggctg ggggcccagt tcttccgggg ctcccccgcg      1140
cactacacac ccctcaccca tccggtctcg gcgccctctt cctcgggatc ccactgtac       1200 gaagggcgg ccgcggccac agacatcgtg gacagccagt acgacgccgc agcccaaggc      1260
cgcctcatag cctcatggac acctgtgtcg ccaccttcca tgtga                     1305
```

<210> SEQ ID NO 16
<211> LENGTH: 1323
<212> TYPE: DNA
<213> ORGANISM: Artificial Sequence
<220> FEATURE:
<223> OTHER INFORMATION: Coding sequence encoding fusion protein
      comprising Brachyury (L254V) Protein plus addition of 15
      nucleotides from Gene FPV 088

<400> SEQUENCE: 16

```
atgaaaaata acttgatgag ctcccctggc accgagagcg cgggaaagag cctgcagtac      60
cgagtggacc acctgctgag cgccgtggag aatgagctgc aggcgggcag cgagaagggc     120
gaccccacag agcgcgaact gcgcgtgggc ctggaggaga gcgagctgtg gctgcgcttc     180
aaggagctca ccaatgagat gatcgtgacc aagaacggca ggaggatgtt tccggtgctg     240
aaggtgaacg tgtctggcct ggaccccaac gccatgtact ccttcctgct ggacttcgtg     300
gcggcggaca ccaccgctg gaagtacgtg aacggggaat gggtgccggg ggcaagccg       360 gagccgcagg cgcccagctg cgtctacatc caccccgact cgcccaactt cggggcccac     420
tggatgaagg ctcccgtctc cttcagcaaa gtcaagctca ccaacaagct caacggaggg     480
ggccagatca tgctgaactc cttgcataag tatgagcctc gaatccacat agtgagagtt     540
gggggtccac agcgcatgat caccagccac tgcttccctg agacccagtt catagcggtg     600
actgcttatc agaacgagga gatcacagct cttaaaatta gtacaatcc atttgcaaag      660 gctttccttg atgcaaagga agaagtgat cacaaagaga tgatggagga acccggagac      720
agccagcaac ctgggtactc ccaatggggg tggcttcttc ctggaaccag caccgtttgt     780
ccacctgcaa atcctcatcc tcagtttgga ggtgccctct ccctcccctc cacgcacagc     840
tgtgacaggt acccaaccct gaggagccac cggtcctcac cctaccccag cccctatgct     900
catcggaaca attctccaac ctattctgac aactcacctg catgtttatc catgctgcaa     960
tcccatgaca attggtccag ccttggaatg cctgcccatc cagcatgct ccccgtgagc     1020 cacaatgcca gcccacctac cagctccagt cagtacccca gcctgtggtc tgtgagcaac    1080
ggcgccgtca ccccgggctc ccaggcagca gccgtgtcca acgggctggg gcccagttc     1140 ttccggggct cccccgcgca ctacacaccc ctcacccatc cggtctcggc gcctcttcc    1200 tcgggatccc cactgtacga aggggcggcc gcggccacag acatcgtgga cagccagtac    1260
gacgccgcag cccaaggccg cctcatagcc tcatggacac ctgtgtcgcc accttccatg    1320
tga                                                                  1323
```

<210> SEQ ID NO 17
<211> LENGTH: 1320
<212> TYPE: DNA
<213> ORGANISM: Artificial Sequence
<220> FEATURE:
<223> OTHER INFORMATION: Coding sequence encoding fusion protein
      comprising Brachyury (L254V) Protein plus addition of 15
      nucleotides from Gene FPV 088 without Brachyury protein atg start
      codon

<400> SEQUENCE: 17

```
atgaaaaata acttgagctc ccctggcacc gagagcgcgg gaaagagcct gcagtaccga    60
gtggaccacc tgctgagcgc cgtggagaat gagctgcagg cgggcagcga aagggcgac   120
cccacagagc gcgaactgcg cgtgggcctg gaggagagcg agctgtggct gcgcttcaag   180
gagctcacca tgagatgat cgtgaccaag aacggcagga ggatgtttcc ggtgctgaag   240
gtgaacgtgt ctggcctgga ccccaacgcc atgtactcct tcctgctgga cttcgtggcg   300
gcggacaacc accgctggaa gtacgtgaac ggggaatggg tgccggggggg caagccggag   360
ccgcaggcgc ccagctgcgt ctacatccac cccgactcgc ccaacttcgg ggcccactgg   420
atgaaggctc ccgtctcctt cagcaaagtc aagctcacca caagctcaa cggagggggc   480
cagatcatgc tgaactcctt gcataagtat gagcctcgaa tccacatagt gagagttggg   540
ggtccacagc gcatgatcac cagccactgc ttccctgaga cccagttcat agcggtgact   600
gcttatcaga acgaggagat cacagctctt aaaattaagt acaatccatt tgcaaaggct   660
ttccttgatg caaggaaag aagtgatcac aaagagatga tggaggaacc cggagacagc   720
cagcaacctg ggtactccca atgggggtgg cttcttcctg gaaccagcac cgtttgtcca   780
cctgcaaatc ctcatcctca gtttggaggt gccctctccc tcccctccac gcacagctgt   840
gacaggtacc caaccctgag gagccaccgg tcctcaccct accccagccc ctatgctcat   900
cggaacaatt ctccaaccta ttctgacaac tcacctgcat gtttatccat gctgcaatcc   960
catgacaatt ggtccagcct tggaatgcct gcccatccca gcatgctccc cgtgagccac  1020
aatgccagcc cacctaccag ctccagtcag taccccagcc tgtggtctgt gagcaacggc  1080
gccgtcaccc cgggctccca ggcagcagcc gtgtccaacg gctgggggc ccagttcttc  1140
cggggctccc ccgcgcacta cacccctc acccatccgg tctcggcgcc ctcttcctcg  1200
ggatccccac tgtacgaagg ggcggccgcg gccacagaca tcgtggacag ccagtacgac  1260
gccgcagccc aaggccgcct catagcctca tggacacctg tgtcgccacc ttccatgtga  1320
```

<210> SEQ ID NO 18
<211> LENGTH: 440
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:16

<400> SEQUENCE: 18

Met Lys Asn Asn Leu Met Ser Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

```
Tyr Ile His Pro Asp Ser Pro Asn Phe Gly Ala His Trp Met Lys Ala
    130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Gly Pro Gln Arg Met Ile Thr Ser His Cys Phe
            180                 185                 190

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
    210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Val Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
        275                 280                 285

Ser His Arg Ser Ser Pro Tyr Pro Ser Pro Tyr Ala His Arg Asn Asn
    290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
        355                 360                 365

Ala Ala Ala Val Ser Asn Gly Leu Gly Ala Gln Phe Phe Arg Gly Ser
    370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Ala Thr Asp Ile Val
                405                 410                 415

Asp Ser Gln Tyr Asp Ala Ala Ala Gln Gly Arg Leu Ile Ala Ser Trp
            420                 425                 430

Thr Pro Val Ser Pro Pro Ser Met
        435                 440

<210> SEQ ID NO 19
<211> LENGTH: 439
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:17 plus addition of 15 nucleotides
      from Gene FPV 088 without Brachyury atg start codon.

<400> SEQUENCE: 19

Met Lys Asn Asn Leu Ser Ser Pro Gly Thr Glu Ser Ala Gly Lys Ser
1               5                   10                  15

Leu Gln Tyr Arg Val Asp His Leu Leu Ser Ala Val Glu Asn Glu Leu
            20                  25                  30
```

-continued

Gln Ala Gly Ser Glu Lys Gly Asp Pro Thr Glu Arg Glu Leu Arg Val
          35                  40                  45

Gly Leu Glu Glu Ser Glu Leu Trp Leu Arg Phe Lys Glu Leu Thr Asn
     50                  55                  60

Glu Met Ile Val Thr Lys Asn Gly Arg Arg Met Phe Pro Val Leu Lys
65                  70                  75                  80

Val Asn Val Ser Gly Leu Asp Pro Asn Ala Met Tyr Ser Phe Leu Leu
              85                  90                  95

Asp Phe Val Ala Ala Asp Asn His Arg Trp Lys Tyr Val Asn Gly Glu
             100                 105                 110

Trp Val Pro Gly Gly Lys Pro Glu Pro Gln Ala Pro Ser Cys Val Tyr
             115                 120                 125

Ile His Pro Asp Ser Pro Asn Phe Gly Ala His Trp Met Lys Ala Pro
         130                 135                 140

Val Ser Phe Ser Lys Val Lys Leu Thr Asn Lys Leu Asn Gly Gly Gly
145                 150                 155                 160

Gln Ile Met Leu Asn Ser Leu His Lys Tyr Glu Pro Arg Ile His Ile
                 165                 170                 175

Val Arg Val Gly Gly Pro Gln Arg Met Ile Thr Ser His Cys Phe Pro
             180                 185                 190

Glu Thr Gln Phe Ile Ala Val Thr Ala Tyr Gln Asn Glu Glu Ile Thr
             195                 200                 205

Ala Leu Lys Ile Lys Tyr Asn Pro Phe Ala Lys Ala Phe Leu Asp Ala
         210                 215                 220

Lys Glu Arg Ser Asp His Lys Glu Met Met Glu Glu Pro Gly Asp Ser
225                 230                 235                 240

Gln Gln Pro Gly Tyr Ser Gln Trp Gly Trp Leu Leu Pro Gly Thr Ser
                 245                 250                 255

Thr Val Cys Pro Pro Ala Asn Pro His Pro Gln Phe Gly Gly Ala Leu
             260                 265                 270

Ser Leu Pro Ser Thr His Ser Cys Asp Arg Tyr Pro Thr Leu Arg Ser
         275                 280                 285

His Arg Ser Ser Pro Tyr Pro Ser Pro Tyr Ala His Arg Asn Asn Ser
         290                 295                 300

Pro Thr Tyr Ser Asp Asn Ser Pro Ala Cys Leu Ser Met Leu Gln Ser
305                 310                 315                 320

His Asp Asn Trp Ser Ser Leu Gly Met Pro Ala His Pro Ser Met Leu
                 325                 330                 335

Pro Val Ser His Asn Ala Ser Pro Pro Thr Ser Ser Ser Gln Tyr Pro
             340                 345                 350

Ser Leu Trp Ser Val Ser Asn Gly Ala Val Thr Pro Gly Ser Gln Ala
         355                 360                 365

Ala Ala Val Ser Asn Gly Leu Gly Ala Gln Phe Phe Arg Gly Ser Pro
         370                 375                 380

Ala His Tyr Thr Pro Leu Thr His Pro Val Ser Ala Pro Ser Ser Ser
385                 390                 395                 400

Gly Ser Pro Leu Tyr Glu Gly Ala Ala Ala Thr Asp Ile Val Asp
                 405                 410                 415

Ser Gln Tyr Asp Ala Ala Ala Gln Gly Arg Leu Ile Ala Ser Trp Thr
             420                 425                 430

Pro Val Ser Pro Pro Ser Met
             435

<210> SEQ ID NO 20
<211> LENGTH: 1353
<212> TYPE: DNA
<213> ORGANISM: Artificial Sequence
<220> FEATURE:
<223> OTHER INFORMATION: Coding sequence encoding fusion protein
      comprising Brachyury (L254V) Protein plus addition of 45
      nucleotides from Gene FPV 088

<400> SEQUENCE: 20

```
atgaaaaata acttgtatga agaaaaaatg aacatgagta agaaaatgag ctcccctggc      60
accgagagcg cgggaaagag cctgcagtac cgagtggacc acctgctgag cgccgtggag     120
aatgagctgc aggcgggcag cgagaagggc accccacag agcgcgaact gcgcgtgggc      180
ctggaggaga gcgagctgtg gctgcgcttc aaggagctca ccaatgagat gatcgtgacc     240
aagaacggca ggaggatgtt tccggtgctg aaggtgaacg tgtctggcct ggaccccaac     300
gccatgtact cgttcctgct ggacttcgtg gcggcggaca ccaccgctg gaagtacgtg      360
aacggggaat gggtgccggg gggcaagccg agccgcagg cgcccagctg cgtctacatc      420
caccccgact cgcccaactt cggggcccac tggatgaagg ctcccgtctc cttcagcaaa     480
gtcaagctca ccaacaagct caacggaggg ggccagatca tgctgaactc cttgcataag     540
tatgagcctc gaatccacat agtgagagtt ggggtccac agcgcatgat caccagccac      600
tgcttcctg agacccagtt catagcggtg actgcttatc agaacgagga gatcacagct      660
cttaaaatta gtacaatcc atttgcaaag gctttccttg atgcaaagga agaagtgat       720
cacaaagaga tgatggagga acccggagac agccagcaac tgggtactc ccaatggggg      780
tggcttcttc ctggaaccag caccgtttgt ccacctgcaa atcctcatcc tcagtttgga     840
ggtgccctct ccctccctc cacgcacagc tgtgacaggt acccaaccct gaggagccac      900
cggtcctcac cctaccccag ccctatgct catcggaaca attctccaac ctattctgac      960
aactcacctg catgtttatc catgctgcaa tcccatgaca attggtccag ccttggaatg    1020
cctgcccatc ccagcatgct ccccgtgagc acaatgcca gcccacctac cagctccagt     1080
cagtaccccca gcctgtggtc tgtgagcaac ggcgccgtca ccccgggctc ccaggcagca   1140
gccgtgtcca acgggctggg ggcccagttc ttccgggget ccccccgcgca ctacacaccc  1200
ctcacccatc cggtctcggc gccctcttcc tcgggatccc cactgtacga agggcggcc    1260
gcggccacag acatcgtgga cagccagtac gacgccgcag cccaaggccg cctcatagcc  1320
tcatggacac ctgtgtcgcc accttccatg tga                                1353
```

<210> SEQ ID NO 21
<211> LENGTH: 1350
<212> TYPE: DNA
<213> ORGANISM: Artificial Sequence
<220> FEATURE:
<223> OTHER INFORMATION: Coding sequence encoding fusion protein
      comprising Brachyury (L254V) Protein plus addition of 45
      nucleotides from Gene FPV 088 without Brachyury atg

<400> SEQUENCE: 21

```
atgaaaaata acttgtatga agaaaaaatg aacatgagta agaaaagctc ccctggcacc      60
gagagcgcgg gaaagagcct gcagtaccga gtggaccacc tgctgagcgc cgtggagaat    120
gagctgcagg cgggcagcga agggcgac ccacagagc gcgaactgcg cgtgggcctg       180
gaggagagcg agctgtggct gcgcttcaag gagctcacca atgagatgat cgtgaccaag    240
aacggcagga ggatgtttcc ggtgctgaag gtgaacgtgt ctggcctgga ccccaacgcc    300
```

```
atgtactcct tcctgctgga cttcgtggcg gcggacaacc accgctggaa gtacgtgaac      360
ggggaatggg tgccgggggg caagccggag ccgcaggcgc ccagctgcgt ctacatccac      420
cccgactcgc ccaacttcgg ggcccactgg atgaaggctc ccgtctcctt cagcaaagtc      480
aagctcacca acaagctcaa cggagggggc cagatcatgc tgaactcctt cataagtat       540 gagcctcgaa tccacatagt gagagttggg ggtccacagc gcatgatcac cagccactgc      600
ttccctgaga cccagttcat agcggtgact gcttatcaga acgaggagat cacagctctt      660
aaaattaagt acaatccatt tgcaaaggct ttccttgatg caaaggaaag aagtgatcac      720
aaagagatga tggaggaacc cggagacagc cagcaacctg ggtactccca atggggtgg       780 cttcttcctg aaccagcac cgtttgtcca cctgcaaatc ctcatcctca gtttggaggt       840
gccctctccc tcccctccac gcacagctgt gacaggtacc caaccctgag gagccaccgg      900 tcctcacccct accccagccc ctatgctcat cggaacaatt ctccaaccta ttctgacaac      960
tcacctgcat gtttatccat gctgcaatcc catgacaatt ggtccagcct tggaatgcct     1020
gcccatccca gcatgctccc cgtgagccac aatgccagcc acctaccag ctccagtcag      1080 taccccagcc tgtggtctgt gagcaacggc gccgtcaccc cgggctccca ggcagcagcc     1140
gtgtccaacg gctgggggc ccagttcttc cggggctccc ccgcgcacta cacaccccctc    1200 acccatccgg tctcggcgcc ctcttcctcg ggatccccac tgtacgaagg ggcggccgcg     1260
gccacagaca tcgtggacag ccagtacgac gccgcagccc aaggccgcct catagcctca     1320
tggacacctg tgtcgccacc ttccatgtga                                       1350
```

<210> SEQ ID NO 22
<211> LENGTH: 450
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:20

<400> SEQUENCE: 22

```
Met Lys Asn Asn Leu Tyr Glu Glu Lys Met Asn Met Ser Lys Met
1               5                   10                  15

Ser Ser Pro Gly Thr Glu Ser Ala Gly Lys Ser Leu Gln Tyr Arg Val
                20                  25                  30

Asp His Leu Leu Ser Ala Val Glu Asn Glu Leu Gln Ala Gly Ser Glu
            35                  40                  45

Lys Gly Asp Pro Thr Glu Arg Glu Leu Arg Val Gly Leu Glu Glu Ser
        50                  55                  60

Glu Leu Trp Leu Arg Phe Lys Glu Leu Thr Asn Glu Met Ile Val Thr
65                  70                  75                  80

Lys Asn Gly Arg Arg Met Phe Pro Val Leu Lys Val Asn Val Ser Gly
                85                  90                  95

Leu Asp Pro Asn Ala Met Tyr Ser Phe Leu Leu Asp Phe Val Ala Ala
                100                 105                 110

Asp Asn His Arg Trp Lys Tyr Val Asn Gly Glu Trp Val Pro Gly Gly
            115                 120                 125

Lys Pro Glu Pro Gln Ala Pro Ser Cys Val Tyr Ile His Pro Asp Ser
        130                 135                 140

Pro Asn Phe Gly Ala His Trp Met Lys Ala Pro Val Ser Phe Ser Lys
145                 150                 155                 160

Val Lys Leu Thr Asn Lys Leu Asn Gly Gly Gly Gln Ile Met Leu Asn
                165                 170                 175
```

```
Ser Leu His Lys Tyr Glu Pro Arg Ile His Ile Val Arg Val Gly Gly
            180                 185                 190

Pro Gln Arg Met Ile Thr Ser His Cys Phe Pro Glu Thr Gln Phe Ile
        195                 200                 205

Ala Val Thr Ala Tyr Gln Asn Glu Glu Ile Thr Ala Leu Lys Ile Lys
    210                 215                 220

Tyr Asn Pro Phe Ala Lys Ala Phe Leu Asp Ala Lys Glu Arg Ser Asp
225                 230                 235                 240

His Lys Glu Met Met Glu Pro Gly Asp Ser Gln Gln Pro Gly Tyr
            245                 250                 255

Ser Gln Trp Gly Trp Leu Leu Pro Gly Thr Ser Thr Val Cys Pro Pro
            260                 265                 270

Ala Asn Pro His Pro Gln Phe Gly Gly Ala Leu Ser Leu Pro Ser Thr
        275                 280                 285

His Ser Cys Asp Arg Tyr Pro Thr Leu Arg Ser His Arg Ser Ser Pro
        290                 295                 300

Tyr Pro Ser Pro Tyr Ala His Arg Asn Asn Ser Pro Thr Tyr Ser Asp
305                 310                 315                 320

Asn Ser Pro Ala Cys Leu Ser Met Leu Gln Ser His Asp Asn Trp Ser
            325                 330                 335

Ser Leu Gly Met Pro Ala His Pro Ser Met Leu Pro Val Ser His Asn
            340                 345                 350

Ala Ser Pro Pro Thr Ser Ser Gln Tyr Pro Ser Leu Trp Ser Val
        355                 360                 365

Ser Asn Gly Ala Val Thr Pro Gly Ser Gln Ala Ala Val Ser Asn
        370                 375                 380

Gly Leu Gly Ala Gln Phe Phe Arg Gly Ser Pro Ala His Tyr Thr Pro
385                 390                 395                 400

Leu Thr His Pro Val Ser Ala Pro Ser Ser Gly Ser Pro Leu Tyr
            405                 410                 415

Glu Gly Ala Ala Ala Ala Thr Asp Ile Val Asp Ser Gln Tyr Asp Ala
            420                 425                 430

Ala Ala Gln Gly Arg Leu Ile Ala Ser Trp Thr Pro Val Ser Pro Pro
        435                 440                 445

Ser Met
    450

<210> SEQ ID NO 23
<211> LENGTH: 449
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:21

<400> SEQUENCE: 23

Met Lys Asn Asn Leu Tyr Glu Glu Lys Met Asn Met Ser Lys Lys Ser
1               5                   10                  15

Ser Pro Gly Thr Glu Ser Ala Gly Lys Ser Leu Gln Tyr Arg Val Asp
            20                  25                  30

His Leu Leu Ser Ala Val Glu Asn Glu Leu Gln Ala Gly Ser Glu Lys
        35                  40                  45

Gly Asp Pro Thr Glu Arg Glu Leu Arg Val Gly Leu Glu Glu Ser Glu
    50                  55                  60

Leu Trp Leu Arg Phe Lys Glu Leu Thr Asn Glu Met Ile Val Thr Lys
```

```
             65                  70                  75                  80
    Asn Gly Arg Arg Met Phe Pro Val Leu Lys Val Asn Val Ser Gly Leu
                     85                  90                  95

Asp Pro Asn Ala Met Tyr Ser Phe Leu Leu Asp Phe Val Ala Ala Asp
                    100                 105                 110

Asn His Arg Trp Lys Tyr Val Asn Gly Glu Trp Val Pro Gly Gly Lys
                    115                 120                 125

Pro Glu Pro Gln Ala Pro Ser Cys Val Tyr Ile His Pro Asp Ser Pro
                    130                 135                 140

Asn Phe Gly Ala His Trp Met Lys Ala Pro Val Ser Phe Ser Lys Val
    145                 150                 155                 160

Lys Leu Thr Asn Lys Leu Asn Gly Gly Gln Ile Met Leu Asn Ser
                    165                 170                 175

Leu His Lys Tyr Glu Pro Arg Ile His Ile Val Arg Val Gly Gly Pro
                    180                 185                 190

Gln Arg Met Ile Thr Ser His Cys Phe Pro Glu Thr Gln Phe Ile Ala
                    195                 200                 205

Val Thr Ala Tyr Gln Asn Glu Glu Ile Thr Ala Leu Lys Ile Lys Tyr
                    210                 215                 220

Asn Pro Phe Ala Lys Ala Phe Leu Asp Ala Lys Glu Arg Ser Asp His
    225                 230                 235                 240

Lys Glu Met Met Glu Glu Pro Gly Asp Ser Gln Gln Pro Gly Tyr Ser
                    245                 250                 255

Gln Trp Gly Trp Leu Leu Pro Gly Thr Ser Thr Val Cys Pro Pro Ala
                    260                 265                 270

Asn Pro His Pro Gln Phe Gly Gly Ala Leu Ser Leu Pro Ser Thr His
                    275                 280                 285

Ser Cys Asp Arg Tyr Pro Thr Leu Arg Ser His Arg Ser Ser Pro Tyr
                    290                 295                 300

Pro Ser Pro Tyr Ala His Arg Asn Asn Ser Pro Thr Tyr Ser Asp Asn
    305                 310                 315                 320

Ser Pro Ala Cys Leu Ser Met Leu Gln Ser His Asp Asn Trp Ser Ser
                    325                 330                 335

Leu Gly Met Pro Ala His Pro Ser Met Leu Pro Val Ser His Asn Ala
                    340                 345                 350

Ser Pro Pro Thr Ser Ser Ser Gln Tyr Pro Ser Leu Trp Ser Val Ser
                    355                 360                 365

Asn Gly Ala Val Thr Pro Gly Ser Gln Ala Ala Val Ser Asn Gly
    370                 375                 380

Leu Gly Ala Gln Phe Phe Arg Gly Ser Pro Ala His Tyr Thr Pro Leu
    385                 390                 395                 400

Thr His Pro Val Ser Ala Pro Ser Ser Gly Ser Pro Leu Tyr Glu
                    405                 410                 415

Gly Ala Ala Ala Ala Thr Asp Ile Val Asp Ser Gln Tyr Asp Ala Ala
                    420                 425                 430

Ala Gln Gly Arg Leu Ile Ala Ser Trp Thr Pro Val Ser Pro Pro Ser
                    435                 440                 445

Met

<210> SEQ ID NO 24
<211> LENGTH: 1326
<212> TYPE: DNA
<213> ORGANISM: Artificial Sequence
<220> FEATURE:
```

<223> OTHER INFORMATION: Coding sequence encoding fusion protein
comprising Brachyury (L254V) Protein plus addition of 18
nucleotides from Gene FPV 088

<400> SEQUENCE: 24

```
atgaacatga gtaagaaaat gagctcccct ggcaccgaga gcgcgggaaa gagcctgcag     60
taccgagtgg accacctgct gagcgccgtg gagaatgagc tgcaggcggg cagcgagaag    120
ggcgacccca cagagcgcga actgcgcgtg ggcctggagg agagcgagct gtggctgcgc    180
ttcaaggagc tcaccaatga gatgatcgtg accaagaacg gcaggaggat gtttccggtg    240
ctgaaggtga acgtgtctgg cctggacccc aacgccatgt actccttcct gctggacttc    300
gtggcggcgg acaaccaccg ctggaagtac gtgaacgggg aatgggtgcc ggggggcaag    360
ccggagccgc aggcgcccag ctgcgtctac atccaccccg actcgcccaa cttcggggcc    420
cactggatga aggctcccgt ctccttcagc aaagtcaagc tcaccaacaa gctcaacgga    480
gggggccaga tcatgctgaa ctccttgcat aagtatgagc ctcgaatcca catagtgaga    540
gttgggggtc cacagcgcat gatcaccagc cactgcttcc ctgagaccca gttcatagcg    600
gtgactgctt atcagaacga ggagatcaca gctcttaaaa ttaagtacaa tccatttgca    660
aaggctttcc ttgatgcaaa ggaaagaagt gatcacaaag agatgatgga ggaacccgga    720
gacagccagc aacctgggta ctcccaatgg gggtggcttc ttcctggaac cagcaccgtt    780
tgtccacctg caaatcctca tcctcagttt ggaggtgccc tctccctccc ctccacgcac    840
agctgtgaca ggtacccaac cctgaggagc caccggtcct caccctaccc cagcccctat    900
gctcatcgga acaattctcc aacctattct gacaactcac ctgcatgttt atccatgctg    960
caatcccatg acaattggtc cagccttgga atgcctgccc atcccagcat gctccccgtg   1020
agccacaatg ccagcccacc taccagctcc agtcagtacc ccagcctgtg gtctgtgagc   1080
aacggcgccg tcaccccggg ctcccaggca gcagccgtgt ccaacgggct gggggcccag   1140
ttcttccggg gctcccccgc gcactacaca cccctcaccc atccggtctc ggcgccctct   1200
tcctcgggat ccccactgta cgaaggggcg gccgcggcca cagacatcgt ggacagccag   1260
tacgacgccg cagcccaagg ccgcctcata gcctcatgga cacctgtgtc gccaccttcc   1320
atgtga                                                              1326
```

<210> SEQ ID NO 25
<211> LENGTH: 1323
<212> TYPE: DNA
<213> ORGANISM: Artificial Sequence
<220> FEATURE:
<223> OTHER INFORMATION: Coding sequence encoding fusion protein
comprising Brachyury (L254V) Protein plus addition of 18
nucleotides from Gene FPV 088 without Brachyury atg

<400> SEQUENCE: 25

```
atgaacatga gtaagaaaag ctcccctggc accgagagcg cgggaaagag cctgcagtac     60
cgagtggacc acctgctgag cgccgtggag aatgagctgc aggcgggcag cgagaagggc    120
gaccccacag agcgcgaact gcgcgtgggc ctggaggaga gcgagctgtg gctgcgcttc    180
aaggagctca ccaatgagat gatcgtgacc aagaacggca ggaggatgtt tccggtgctg    240
aaggtgaacg tgtctggcct ggaccccaac gccatgtact ccttcctgct ggacttcgtg    300
gcggcggaca accaccgctg gaagtacgtg aacggggaat gggtgccggg gggcaagccg    360
gagccgcagg cgcccagctg cgtctacatc caccccgact cgcccaactt cggggcccac    420
tggatgaagg ctcccgtctc cttcagcaaa gtcaagctca ccaacaagct caacggaggg    480
```

```
ggccagatca tgctgaactc cttgcataag tatgagcctc gaatccacat agtgagagtt      540 ggggtccac agcgcatgat caccagccac tgcttccctg agacccagtt catagcggtg       600
actgcttatc agaacgagga gatcacagct cttaaaatta agtacaatcc atttgcaaag      660
gctttccttg atgcaaagga aagaagtgat cacaaagaga tgatggagga acccggagac      720
agccagcaac tgggtactcc caatggggg tggcttcttc ctggaaccag caccgtttgt       780
ccacctgcaa atcctcatcc tcagtttgga ggtgccctct ccctcccctc cacgcacagc      840
tgtgacaggt acccaaccct gaggagccac cggtcctcac cctaccccag ccctatgct      900 catcggaaca attctccaac ctattctgac aactcacctg catgtttatc catgctgcaa      960
tcccatgaca attggtccag ccttggaatg cctgcccatc ccagcatgct cccgtgagc      1020 cacaatgcca gcccacctac cagctccagt cagtacccca gcctgtggtc tgtgagcaac      1080
ggcgccgtca ccccgggctc ccaggcagca gccgtgtcca acgggctggg ggcccagttc      1140
ttccggggct cccccgcgca ctacacaccc ctcacccatc cggtctcggc gccctcttcc      1200
tcgggatccc cactgtacga aggggcggcc gcggccacag acatcgtgga cagccagtac      1260
gacgccgcag cccaaggccg cctcatagcc tcatggacac tgtgtcgcc accttccatg      1320 tga                                                                   1323
```

<210> SEQ ID NO 26
<211> LENGTH: 441
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:24

<400> SEQUENCE: 26

```
Met Asn Met Ser Lys Lys Met Ser Ser Pro Gly Thr Glu Ser Ala Gly
1               5                   10                  15

Lys Ser Leu Gln Tyr Arg Val Asp His Leu Leu Ser Ala Val Glu Asn
            20                  25                  30

Glu Leu Gln Ala Gly Ser Glu Lys Gly Asp Pro Thr Glu Arg Glu Leu
        35                  40                  45

Arg Val Gly Leu Glu Glu Ser Glu Leu Trp Leu Arg Phe Lys Glu Leu
    50                  55                  60

Thr Asn Glu Met Ile Val Thr Lys Asn Gly Arg Arg Met Phe Pro Val
65                  70                  75                  80

Leu Lys Val Asn Val Ser Gly Leu Asp Pro Asn Ala Met Tyr Ser Phe
                85                  90                  95

Leu Leu Asp Phe Val Ala Ala Asp Asn His Arg Trp Lys Tyr Val Asn
            100                 105                 110

Gly Glu Trp Val Pro Gly Gly Lys Pro Glu Pro Gln Ala Pro Ser Cys
        115                 120                 125

Val Tyr Ile His Pro Asp Ser Pro Asn Phe Gly Ala His Trp Met Lys
    130                 135                 140

Ala Pro Val Ser Phe Ser Lys Val Lys Leu Thr Asn Lys Leu Asn Gly
145                 150                 155                 160

Gly Gly Gln Ile Met Leu Asn Ser Leu His Lys Tyr Glu Pro Arg Ile
                165                 170                 175

His Ile Val Arg Val Gly Gly Pro Gln Arg Met Ile Thr Ser His Cys
            180                 185                 190

Phe Pro Glu Thr Gln Phe Ile Ala Val Thr Ala Tyr Gln Asn Glu Glu
```

```
                    195                 200                 205
Ile Thr Ala Leu Lys Ile Lys Tyr Asn Pro Phe Ala Lys Ala Phe Leu
    210                 215                 220

Asp Ala Lys Glu Arg Ser Asp His Lys Glu Met Met Glu Pro Gly
225                 230                 235                 240

Asp Ser Gln Gln Pro Gly Tyr Ser Gln Trp Gly Trp Leu Leu Pro Gly
                245                 250                 255

Thr Ser Thr Val Cys Pro Pro Ala Asn Pro His Pro Gln Phe Gly Gly
            260                 265                 270

Ala Leu Ser Leu Pro Ser Thr His Ser Cys Asp Arg Tyr Pro Thr Leu
        275                 280                 285

Arg Ser His Arg Ser Ser Pro Tyr Pro Ser Pro Tyr Ala His Arg Asn
    290                 295                 300

Asn Ser Pro Thr Tyr Ser Asp Asn Ser Pro Ala Cys Leu Ser Met Leu
305                 310                 315                 320

Gln Ser His Asp Asn Trp Ser Ser Leu Gly Met Pro Ala His Pro Ser
                325                 330                 335

Met Leu Pro Val Ser His Asn Ala Ser Pro Pro Thr Ser Ser Ser Gln
            340                 345                 350

Tyr Pro Ser Leu Trp Ser Val Ser Asn Gly Ala Val Thr Pro Gly Ser
        355                 360                 365

Gln Ala Ala Val Ser Asn Gly Leu Gly Ala Gln Phe Phe Arg Gly
    370                 375                 380

Ser Pro Ala His Tyr Thr Pro Leu Thr His Pro Val Ser Ala Pro Ser
385                 390                 395                 400

Ser Ser Gly Ser Pro Leu Tyr Glu Gly Ala Ala Ala Thr Asp Ile
                405                 410                 415

Val Asp Ser Gln Tyr Asp Ala Ala Gln Gly Arg Leu Ile Ala Ser
            420                 425                 430

Trp Thr Pro Val Ser Pro Pro Ser Met
        435                 440

<210> SEQ ID NO 27
<211> LENGTH: 440
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:25

<400> SEQUENCE: 27

Met Asn Met Ser Lys Lys Ser Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110
```

| | | | | | | | | | | | |
|---|---|---|---|---|---|---|---|---|---|---|---|
|Glu|Trp|Val|Pro|Gly|Gly|Lys|Pro|Glu|Pro|Gln|Ala|Pro|Ser|Cys|Val|
| |115| | | | |120| | | |125| |

Glu Trp Val Pro Gly Gly Lys Pro Glu Pro Gln Ala Pro Ser Cys Val
     115                    120               125

Tyr Ile His Pro Asp Ser Pro Asn Phe Gly Ala His Trp Met Lys Ala
130                 135                 140

Pro Val Ser Phe Ser Lys Val Lys Leu Thr Asn Lys Leu Asn Gly Gly
145            150               155           160

Gly Gln Ile Met Leu Asn Ser Leu His Lys Tyr Glu Pro Arg Ile His
         165              170            175

Ile Val Arg Val Gly Gly Pro Gln Arg Met Ile Thr Ser His Cys Phe
        180             185             190

Pro Glu Thr Gln Phe Ile Ala Val Thr Ala Tyr Gln Asn Glu Glu Ile
     195              200            205

Thr Ala Leu Lys Ile Lys Tyr Asn Pro Phe Ala Lys Ala Phe Leu Asp
210               215            220

Ala Lys Glu Arg Ser Asp His Lys Glu Met Met Glu Glu Pro Gly Asp
225            230               235           240

Ser Gln Gln Pro Gly Tyr Ser Gln Trp Gly Trp Leu Leu Pro Gly Thr
         245              250            255

Ser Thr Val Cys Pro Pro Ala Asn Pro His Pro Gln Phe Gly Gly Ala
        260             265            270

Leu Ser Leu Pro Ser Thr His Ser Cys Asp Arg Tyr Pro Thr Leu Arg
     275              280            285

Ser His Arg Ser Ser Pro Tyr Pro Ser Pro Tyr Ala His Arg Asn Asn
     290              295            300

Ser Pro Thr Tyr Ser Asp Asn Ser Pro Ala Cys Leu Ser Met Leu Gln
305               310            315           320

Ser His Asp Asn Trp Ser Ser Leu Gly Met Pro Ala His Pro Ser Met
         325              330           335

Leu Pro Val Ser His Asn Ala Ser Pro Pro Thr Ser Ser Ser Gln Tyr
         340            345           350

Pro Ser Leu Trp Ser Val Ser Asn Gly Ala Val Thr Pro Gly Ser Gln
        355            360           365

Ala Ala Ala Val Ser Asn Gly Leu Gly Ala Gln Phe Phe Arg Gly Ser
370               375            380

Pro Ala His Tyr Thr Pro Leu Thr His Pro Val Ser Ala Pro Ser Ser
385               390            395           400

Ser Gly Ser Pro Leu Tyr Glu Gly Ala Ala Ala Thr Asp Ile Val
          405           410            415

Asp Ser Gln Tyr Asp Ala Ala Gln Gly Arg Leu Ile Ala Ser Trp
        420            425            430

Thr Pro Val Ser Pro Pro Ser Met
435               440

<210> SEQ ID NO 28
<211> LENGTH: 1320
<212> TYPE: DNA
<213> ORGANISM: Artificial Sequence
<220> FEATURE:
<223> OTHER INFORMATION: Coding sequence encoding Fusion protein
     comprising Brachyury (L254V) Protein plus addition of 12
     nucleotides from Gene FPV 088

<400> SEQUENCE: 28
atgagtaaga aaatgagctc ccctggcacc gagagcgcgg gaaagagcct gcagtaccga   60
gtggaccacc tgctgagcgc cgtggagaat gagctgcagg cgggcagcga gaagggcgac  120

| | |
|---|---:|
| cccacagagc gcgaactgcg cgtgggcctg gaggagagcg agctgtggct gcgcttcaag | 180 |
| gagctcacca atgagatgat cgtgaccaag aacggcagga ggatgtttcc ggtgctgaag | 240 |
| gtgaacgtgt ctggcctgga ccccaacgcc atgtactcct tcctgctgga cttcgtggcg | 300 |
| gcggacaacc accgctggaa gtacgtgaac ggggaatggg tgccgggggg caagccggag | 360 |
| ccgcaggcgc ccagctgcgt ctacatccac cccgactcgc ccaacttcgg ggcccactgg | 420 |
| atgaaggctc ccgtctcctt cagcaaagtc aagctcacca acaagctcaa cggagggggc | 480 |
| cagatcatgc tgaactcctt gcataagtat gagcctcgaa tccacatagt gagagttggg | 540 |
| ggtccacagc gcatgatcac cagccactgc ttccctgaga cccagttcat agcggtgact | 600 |
| gcttatcaga cgaggagat cacagctctt aaaattaagt acaatccatt tgcaaaggct | 660 |
| ttccttgatg caaggaaag aagtgatcac aaagagatga tggaggaacc cggagacagc | 720 |
| cagcaacctg gtactccca atgggggtgg cttcttcctg gaaccagcac cgtttgtcca | 780 |
| cctgcaaatc ctcatcctca gtttggaggt gccctctccc tccctccac gcacagctgt | 840 |
| gacaggtacc caaccctgag gagccaccgg tcctcaccct accccagccc ctatgctcat | 900 |
| cggaacaatt ctccaaccta ttctgacaac tcacctgcat gtttatccat gctgcaatcc | 960 |
| catgacaatt ggtccagcct ggaatgcct gcccatccca gcatgctccc cgtgagccac | 1020 |
| aatgccagcc cacctaccag ctccagtcag taccccagcc tgtggtctgt gagcaacggc | 1080 |
| gccgtcaccc cgggctccca ggcagcagcc gtgtccaacg gctgggggc ccagttcttc | 1140 |
| cggggctccc ccgcgcacta cacacccctc acccatccgg tctcggcgcc ctcttcctcg | 1200 |
| ggatccccac tgtacgaagg ggcggccgcg ccacagaca tcgtggacag ccagtacgac | 1260 |
| gccgcagccc aaggccgcct catagcctca tggacacctg tgtcgccacc ttccatgtga | 1320 |

<210> SEQ ID NO 29
<211> LENGTH: 1317
<212> TYPE: DNA
<213> ORGANISM: Artificial Sequence
<220> FEATURE:
<223> OTHER INFORMATION: Coding sequence encoding Fusion protein comprising Brachyury (L254V) Protein plus addition of 12 nucleotides from Gene FPV 088 without Brachyury atg start codon

<400> SEQUENCE: 29

| | |
|---|---:|
| atgagtaaga aaagctcccc tggcaccgag agcgcgggaa agagcctgca gtaccgagtg | 60 |
| gaccacctgc tgagcgccgt ggagaatgag ctgcaggcgg gcagcgagaa gggcgacccc | 120 |
| acagagcgcg aactgcgcgt gggcctggag gagagcgagc tgtggctgcg cttcaaggag | 180 |
| ctcaccaatg agatgatcgt gaccaagaac ggcaggagga tgtttccggt gctgaaggtg | 240 |
| aacgtgtctg gcctggaccc caacgccatg tactccttcc tgctggactt cgtggcggcg | 300 |
| gacaaccacc gctggaagta cgtgaacggg gaatgggtgc cggggggcaa gccggagccg | 360 |
| caggcgccca gctgcgtcta catccacccc gactcgccca acttcggggc ccactggatg | 420 |
| aaggctcccg tctccttcag caaagtcaag ctcaccaaca agctcaacgg agggggccag | 480 |
| atcatgctga actccttgca taagtatgag cctcgaatcc acatagtgag agttgggggt | 540 |
| ccacagcgca tgatcaccag ccactgcttc cctgagaccc agttcatagc ggtgactgct | 600 |
| tatcagaacg aggagatcac agctcttaaa attaagtaca atccatttgc aaaggctttc | 660 |
| cttgatgcaa ggaaagaag tgatcacaaa gagatgatgg aggaacccgg agacagccag | 720 |
| caacctgggt actcccaatg ggggtggctt cttcctggaa ccagcaccgt ttgtccacct | 780 |
| gcaaatcctc atcctcagtt tggaggtgcc ctctccctcc cctccacgca cagctgtgac | 840 |

-continued

```
aggtacccaa ccctgaggag ccaccggtcc tcaccctacc ccagccccta tgctcatcgg      900
aacaattctc caacctattc tgacaactca cctgcatgtt tatccatgct gcaatcccat      960
gacaattggt ccagccttgg aatgcctgcc catcccagca tgctccccgt gagccacaat     1020
gccagcccac ctaccagctc cagtcagtac cccagcctgt ggtctgtgag caacggcgcc     1080
gtcaccccgg ctcccaggc agcagccgtg tccaacgggc tgggggccca gttcttccgg      1140
ggctcccccg cgcactacac acccctcacc catccggtct cggcgccctc ttcctcggga     1200
tccccactgt acgaaggggc ggccgcggcc acagacatcg tggacagcca gtacgacgcc     1260
gcagcccaag ccgcctcat agcctcatgg acacctgtgt cgccaccttc catgtga       1317
```

<210> SEQ ID NO 30
<211> LENGTH: 439
<212> TYPE: PRT
<213> ORGANISM: Artificial Sequence
<220> FEATURE:
<223> OTHER INFORMATION: Fusion protein comprising Brachyury (L254V) Protein encoded by SEQ ID NO:28

<400> SEQUENCE: 30

```
Met Ser Lys Lys Met Ser Ser Pro Gly Thr Glu Ser Ala Gly Lys Ser
1               5                   10                  15

Leu Gln Tyr Arg Val Asp His Leu Leu Ser Ala Val Glu Asn Glu Leu
            20                  25                  30

Gln Ala Gly Ser Glu Lys Gly Asp Pro Thr Glu Arg Glu Leu Arg Val
        35                  40                  45

Gly Leu Glu Glu Ser Glu Leu Trp Leu Arg Phe Lys Glu Leu Thr Asn
    50                  55                  60

Glu Met Ile Val Thr Lys Asn Gly Arg Arg Met Phe Pro Val Leu Lys
65                  70                  75                  80

Val Asn Val Ser Gly Leu Asp Pro Asn Ala Met Tyr Ser Phe Leu Leu
                85                  90                  95

Asp Phe Val Ala Ala Asp Asn His Arg Trp Lys Tyr Val Asn Gly Glu
            100                 105                 110

Trp Val Pro Gly Gly Lys Pro Glu Pro Gln Ala Pro Ser Cys Val Tyr
        115                 120                 125

Ile His Pro Asp Ser Pro Asn Phe Gly Ala His Trp Met Lys Ala Pro
    130                 135                 140

Val Ser Phe Ser Lys Val Lys Leu Thr Asn Lys Leu Asn Gly Gly Gly
145                 150                 155                 160

Gln Ile Met Leu Asn Ser Leu His Lys Tyr Glu Pro Arg Ile His Ile
                165                 170                 175

Val Arg Val Gly Gly Pro Gln Arg Met Ile Thr Ser His Cys Phe Pro
            180                 185                 190

Glu Thr Gln Phe Ile Ala Val Thr Ala Tyr Gln Asn Glu Glu Ile Thr
        195                 200                 205

Ala Leu Lys Ile Lys Tyr Asn Pro Phe Ala Lys Ala Phe Leu Asp Ala
    210                 215                 220

Lys Glu Arg Ser Asp His Lys Glu Met Met Glu Glu Pro Gly Asp Ser
225                 230                 235                 240

Gln Gln Pro Gly Tyr Ser Gln Trp Gly Trp Leu Leu Pro Gly Thr Ser
                245                 250                 255

Thr Val Cys Pro Pro Ala Asn Pro His Pro Gln Phe Gly Gly Ala Leu
            260                 265                 270
```

```
Ser Leu Pro Ser Thr His Ser Cys Asp Arg Tyr Pro Thr Leu Arg Ser
            275                 280                 285

His Arg Ser Ser Pro Tyr Pro Ser Pro Tyr Ala His Arg Asn Asn Ser
            290                 295                 300

Pro Thr Tyr Ser Asp Asn Ser Pro Ala Cys Leu Ser Met Leu Gln Ser
305                 310                 315                 320

His Asp Asn Trp Ser Ser Leu Gly Met Pro Ala His Pro Ser Met Leu
            325                 330                 335

Pro Val Ser His Asn Ala Ser Pro Pro Thr Ser Ser Ser Gln Tyr Pro
            340                 345                 350

Ser Leu Trp Ser Val Ser Asn Gly Ala Val Thr Pro Gly Ser Gln Ala
            355                 360                 365

Ala Ala Val Ser Asn Gly Leu Gly Ala Gln Phe Phe Arg Gly Ser Pro
            370                 375                 380

Ala His Tyr Thr Pro Leu Thr His Pro Val Ser Ala Pro Ser Ser Ser
385                 390                 395                 400

Gly Ser Pro Leu Tyr Glu Gly Ala Ala Ala Thr Asp Ile Val Asp
                    405                 410                 415

Ser Gln Tyr Asp Ala Ala Ala Gln Gly Arg Leu Ile Ala Ser Trp Thr
            420                 425                 430

Pro Val Ser Pro Pro Ser Met
            435

<210> SEQ ID NO 31
<211> LENGTH: 438
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:29

<400> SEQUENCE: 31

Met Ser Lys Lys Ser Ser Pro Gly Thr Glu Ser Ala Gly Lys Ser Leu
1               5                   10                  15

Gln Tyr Arg Val Asp His Leu Leu Ser Ala Val Glu Asn Glu Leu Gln
            20                  25                  30

Ala Gly Ser Glu Lys Gly Asp Pro Thr Glu Arg Glu Leu Arg Val Gly
        35                  40                  45

Leu Glu Glu Ser Glu Leu Trp Leu Arg Phe Lys Glu Leu Thr Asn Glu
    50                  55                  60

Met Ile Val Thr Lys Asn Gly Arg Arg Met Phe Pro Val Leu Lys Val
65                  70                  75                  80

Asn Val Ser Gly Leu Asp Pro Asn Ala Met Tyr Ser Phe Leu Leu Asp
            85                  90                  95

Phe Val Ala Ala Asp Asn His Arg Trp Lys Tyr Val Asn Gly Glu Trp
            100                 105                 110

Val Pro Gly Gly Lys Pro Glu Pro Gln Ala Pro Ser Cys Val Tyr Ile
        115                 120                 125

His Pro Asp Ser Pro Asn Phe Gly Ala His Trp Met Lys Ala Pro Val
130                 135                 140

Ser Phe Ser Lys Val Lys Leu Thr Asn Lys Leu Asn Gly Gly Gly Gln
145                 150                 155                 160

Ile Met Leu Asn Ser Leu His Lys Tyr Glu Pro Arg Ile His Ile Val
            165                 170                 175

Arg Val Gly Gly Pro Gln Arg Met Ile Thr Ser His Cys Phe Pro Glu
            180                 185                 190
```

Thr Gln Phe Ile Ala Val Thr Ala Tyr Gln Asn Glu Glu Ile Thr Ala
        195                 200                 205

Le

-continued

```
gggggccaga tcatgctgaa ctccttgcat aagtatgagc ctcgaatcca catagtgaga    600
gttgggggtc cacagcgcat gatcaccagc cactgcttcc ctgagaccca gttcatagcg    660
gtgactgctt atcagaacga ggagatcaca gctcttaaaa ttaagtacaa tccatttgca    720
aaggctttcc ttgatgcaaa ggaaagaagt gatcacaaag agatgatgga ggaacccgga    780
gacagccagc aacctgggta ctcccaatgg gggtggcttc ttcctggaac cagcaccgtt    840
tgtccacctg caaatcctca tcctcagttt ggaggtgccc tctccctccc ctccacgcac    900
agctgtgaca ggtacccaac cctgaggagc caccggtcct caccctaccc cagcccctat    960
gctcatcgga acaattctcc aacctattct gacaactcac ctgcatgttt atccatgctg   1020
caatcccatg acaattggtc cagccttgga atgcctgccc atcccagcat gctccccgtg   1080
agccacaatg ccagcccacc taccagctcc agtcagtacc ccagcctgtg gtctgtgagc   1140
aacggcgccg tcaccccggg ctcccaggca gcagccgtgt ccaacgggct ggggggcccag  1200
ttcttccggg gctcccccgc gcactacaca cccctcaccc atccggtctc ggcgccctct   1260
tcctcgggat ccccactgta cgaaggggcg ccgcggccca cagacatcgt ggacagccag   1320
tacgacgccg cagcccaagg ccgcctcata gcctcatgga cacctgtgtc gccaccttcc   1380
atgtga                                                             1386
```

<210> SEQ ID NO 33
<211> LENGTH: 1383
<212> TYPE: DNA
<213> ORGANISM: Artificial Sequence
<220> FEATURE:
<223> OTHER INFORMATION: Coding sequence encoding Fusion protein
      comprising Brachyury (L254V) Protein plus addition of 75
      nucleotides from Gene FPV 088 and an atc, without Brachyury atg
      start codon

<400> SEQUENCE: 33

```
atgaaaaata acttgtatga agaaaaaatg aacatgagta agaaacaagt aaaaactcaa     60
agtaaatgta ataatatcag ctcccctggc accgagagcg cgggaaagag cctgcagtac   120
cgagtggacc acctgctgag cgccgtggag aatgagctgc aggcgggcag cgagaagggc   180
gaccccacag agcgcgaact gcgcgtgggc ctggaggaga cgcgagctgtg gctgcgcttc   240
aaggagctca ccaatgagat gatcgtgacc aagaacggca ggaggatgtt tccggtgctg   300
aaggtgaacg tgtctggcct ggaccccaac gccatgtact ccttcctgct ggacttcgtg   360
gcggcggaca ccaccgctg gaagtacgtg aacggggaat gggtgccggg gggcaagccg   420
gagccgcagg cgcccagctg cgtctacatc caccccgact cgcccaactt cggggcccac   480
tggatgaagg ctcccgtctc cttcagcaaa gtcaagctca ccaacaagct caacggaggg   540
ggccagatca tgctgaactc cttgcataag tatgagcctc gaatccacat agtgagagtt   600
ggggggtccac agcgcatgat caccagccac tgcttccctg agacccagtt catagcggtg   660
actgcttatc agaacgagga gatcacagct cttaaaatta gtacaatcc atttgcaaag   720
gctttccttg atgcaaagga agaagtgat cacaaagaga tgatggagga acccggagac   780
agccagcaac ctgggtactc ccaatggggg tggcttcttc ctggaaccag caccgtttgt   840
ccacctgcaa atcctcatcc tcagtttgga ggtgccctct ccctccctc acgcacagc   900
tgtgacaggt acccaaccct gaggagccac cggtcctcac cctacccag ccctatgct   960
catcggaaca attctccaac ctattctgac aactcacctg catgtttatc catgctgcaa  1020
tcccatgaca attggtccag ccttggaatg cctgcccatc ccagcatgct ccccgtgagc  1080
```

```
cacaatgcca gcccacctac cagctccagt cagtaccccca gcctgtggtc tgtgagcaac   1140
ggcgccgtca ccccgggctc ccaggcagca gccgtgtcca acgggctggg ggcccagttc   1200
ttccggggct cccccgcgca ctacacaccc ctcacccatc cggtctcggc gccctcttcc   1260
tcgggatccc cactgtacga aggggcggcc gcggccacag acatcgtgga cagccagtac   1320
gacgccgcag cccaaggccg cctcatagcc tcatggacac tgtgtcgcc accttccatg   1380 tga                                                                1383
```

```
<210> SEQ ID NO 34
<211> LENGTH: 461
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO: 32

<400> SEQUENCE: 34
```

```
Met Lys Asn Asn Leu Tyr Glu Glu Lys Met Asn Met Ser Lys Lys Gln
1               5                   10                  15

Val Lys Thr Gln Ser Lys Cys Asn Asn Ile Met Ser Ser Pro Gly Thr
            20                  25                  30

Glu Ser Ala Gly Lys Ser Leu Gln Tyr Arg Val Asp His Leu Leu Ser
        35                  40                  45

Ala Val Glu Asn Glu Leu Gln Ala Gly Ser Glu Lys Gly Asp Pro Thr
    50                  55                  60

Glu Arg Glu Leu Arg Val Gly Leu Glu Glu Ser Glu Leu Trp Leu Arg
65                  70                  75                  80

Phe Lys Glu Leu Thr Asn Glu Met Ile Val Thr Lys Asn Gly Arg Arg
                85                  90                  95

Met Phe Pro Val Leu Lys Val Asn Val Ser Gly Leu Asp Pro Asn Ala
            100                 105                 110

Met Tyr Ser Phe Leu Leu Asp Phe Val Ala Ala Asp Asn His Arg Trp
        115                 120                 125

Lys Tyr Val Asn Gly Glu Trp Val Pro Gly Gly Lys Pro Glu Pro Gln
    130                 135                 140

Ala Pro Ser Cys Val Tyr Ile His Pro Asp Ser Pro Asn Phe Gly Ala
145                 150                 155                 160

His Trp Met Lys Ala Pro Val Ser Phe Ser Lys Val Lys Leu Thr Asn
                165                 170                 175

Lys Leu Asn Gly Gly Gly Gln Ile Met Leu Asn Ser Leu His Lys Tyr
            180                 185                 190

Glu Pro Arg Ile His Ile Val Arg Val Gly Gly Pro Gln Arg Met Ile
        195                 200                 205

Thr Ser His Cys Phe Pro Glu Thr Gln Phe Ile Ala Val Thr Ala Tyr
    210                 215                 220

Gln Asn Glu Glu Ile Thr Ala Leu Lys Ile Lys Tyr Asn Pro Phe Ala
225                 230                 235                 240

Lys Ala Phe Leu Asp Ala Lys Glu Arg Ser Asp His Lys Glu Met Met
                245                 250                 255

Glu Glu Pro Gly Asp Ser Gln Gln Pro Gly Tyr Ser Gln Trp Gly Trp
            260                 265                 270

Leu Leu Pro Gly Thr Ser Thr Val Cys Pro Pro Ala Asn Pro His Pro
        275                 280                 285

Gln Phe Gly Gly Ala Leu Ser Leu Pro Ser Thr His Ser Cys Asp Arg
    290                 295                 300
```

```
Tyr Pro Thr Leu Arg Ser His Arg Ser Ser Pro Tyr Pro Ser Pro Tyr
305                 310                 315                 320

Ala His Arg Asn Asn Ser Pro Thr Tyr Ser Asp Asn Ser Pro Ala Cys
            325                 330                 335

Leu Ser Met Leu Gln Ser His Asp Asn Trp Ser Ser Leu Gly Met Pro
        340                 345                 350

Ala His Pro Ser Met Leu Pro Val Ser His Asn Ala Ser Pro Pro Thr
    355                 360                 365

Ser Ser Ser Gln Tyr Pro Ser Leu Trp Ser Val Ser Asn Gly Ala Val
370                 375                 380

Thr Pro Gly Ser Gln Ala Ala Val Ser Asn Gly Leu Gly Ala Gln
385                 390                 395                 400

Phe Phe Arg Gly Ser Pro Ala His Tyr Thr Pro Leu Thr His Pro Val
                405                 410                 415

Ser Ala Pro Ser Ser Ser Gly Ser Pro Leu Tyr Glu Gly Ala Ala Ala
            420                 425                 430

Ala Thr Asp Ile Val Asp Ser Gln Tyr Asp Ala Ala Ala Gln Gly Arg
        435                 440                 445

Leu Ile Ala Ser Trp Thr Pro Val Ser Pro Ser Met
    450                 455                 460

<210> SEQ ID NO 35
<211> LENGTH: 460
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO: 33

<400> SEQUENCE: 35

Met Lys Asn Asn Leu Tyr Glu Glu Lys Met Asn Met Ser Lys Lys Gln
1               5                   10                  15

Val Lys Thr Gln Ser Lys Cys Asn Asn Ile Ser Ser Pro Gly Thr Glu
            20                  25                  30

Ser Ala Gly Lys Ser Leu Gln Tyr Arg Val Asp His Leu Leu Ser Ala
        35                  40                  45

Val Glu Asn Glu Leu Gln Ala Gly Ser Glu Lys Gly Asp Pro Thr Glu
    50                  55                  60

Arg Glu Leu Arg Val Gly Leu Glu Glu Ser Glu Leu Trp Leu Arg Phe
65                  70                  75                  80

Lys Glu Leu Thr Asn Glu Met Ile Val Thr Lys Asn Gly Arg Arg Met
                85                  90                  95

Phe Pro Val Leu Lys Val Asn Val Ser Gly Leu Asp Pro Asn Ala Met
            100                 105                 110

Tyr Ser Phe Leu Leu Asp Phe Val Ala Ala Asp Asn His Arg Trp Lys
        115                 120                 125

Tyr Val Asn Gly Glu Trp Val Pro Gly Gly Lys Pro Glu Pro Gln Ala
    130                 135                 140

Pro Ser Cys Val Tyr Ile His Pro Asp Ser Pro Asn Phe Gly Ala His
145                 150                 155                 160

Trp Met Lys Ala Pro Val Ser Phe Ser Lys Val Lys Leu Thr Asn Lys
                165                 170                 175

Leu Asn Gly Gly Gly Gln Ile Met Leu Asn Ser Leu His Lys Tyr Glu
            180                 185                 190

Pro Arg Ile His Ile Val Arg Val Gly Gly Pro Gln Arg Met Ile Thr
```

| | | | 195 | | | | 200 | | | | 205 | | |
|---|---|---|---|---|---|---|---|---|---|---|---|---|---|
Ser His Cys Phe Pro Glu Thr Gln Phe Ile Ala Val Thr Ala Tyr Gln
210 215 220

Asn Glu Glu Ile Thr Ala Leu Lys Ile Lys Tyr Asn Pro Phe Ala Lys
225 230 235 240

Ala Phe Leu Asp Ala Lys Glu Arg Ser Asp His Lys Glu Met Met Glu
245 250 255

Glu Pro Gly Asp Ser Gln Gln Pro Gly Tyr Ser Gln Trp Gly Trp Leu
260 265 270

Leu Pro Gly Thr Ser Thr Val Cys Pro Pro Ala Asn Pro His Pro Gln
275 280 285

Phe Gly Gly Ala Leu Ser Leu Pro Ser Thr His Ser Cys Asp Arg Tyr
290 295 300

Pro Thr Leu Arg Ser His Arg Ser Ser Pro Tyr Pro Ser Pro Tyr Ala
305 310 315 320

His Arg Asn Asn Ser Pro Thr Tyr Ser Asp Asn Ser Pro Ala Cys Leu
325 330 335

Ser Met Leu Gln Ser His Asp Asn Trp Ser Ser Leu Gly Met Pro Ala
340 345 350

His Pro Ser Met Leu Pro Val Ser His Asn Ala Ser Pro Pro Thr Ser
355 360 365

Ser Ser Gln Tyr Pro Ser Leu Trp Ser Val Ser Asn Gly Ala Val Thr
370 375 380

Pro Gly Ser Gln Ala Ala Ala Val Ser Asn Gly Leu Gly Ala Gln Phe
385 390 395 400

Phe Arg Gly Ser Pro Ala His Tyr Thr Pro Leu Thr His Pro Val Ser
405 410 415

Ala Pro Ser Ser Ser Gly Ser Pro Leu Tyr Glu Gly Ala Ala Ala Ala
420 425 430

Thr Asp Ile Val Asp Ser Gln Tyr Asp Ala Ala Ala Gln Gly Arg Leu
435 440 445

Ile Ala Ser Trp Thr Pro Val Ser Pro Pro Ser Met
450 455 460

<210> SEQ ID NO 36
<211> LENGTH: 1359
<212> TYPE: DNA
<213> ORGANISM: Artificial Sequence
<220> FEATURE:
<223> OTHER INFORMATION: Coding sequence encoding Fusion protein
 comprising Brachyury (L254V) Protein plus addition of 48
 nucleotides from Gene FPV 088 and an atc

<400> SEQUENCE: 36

```
atgaacatga gtaagaaaca agtaaaaact caaagtaaat gtaataatat catgagctcc      60
cctggcaccg agagcgcggg aaagagcctg cagtaccgag tggaccacct gctgagcgcc     120
gtggagaatg agctgcaggc gggcagcgag aagggcgacc ccacagagcg cgaactgcgc     180
gtgggcctgg aggagagcga gctgtggctg cgcttcaagg agctcaccaa tgagatgatc     240
gtgaccaaga acggcaggag gatgtttccg gtgctgaagg tgaacgtgtc tggcctggac     300
cccaacgcca tgtactcctt cctgctggac ttcgtggcgg cggacaacca ccgctggaag     360
tacgtgaacg gggaatgggt gccggggggc aagccggagc gcaggcgcc cagctgcgtc     420 tacatccacc ccgactcgcc caacttcggg gcccactgga tgaaggctcc cgtctccttc     480
agcaaagtca agctcaccaa caagctcaac ggagggggcc agatcatgct gaactccttg     540
```

```
cataagtatg agcctcgaat ccacatagtg agagttgggg gtccacagcg catgatcacc     600
agccactgct tccctgagac ccagttcata gcggtgactg cttatcagaa cgaggagatc     660
acagctctta aaattaagta caatccattt gcaaaggctt tccttgatgc aaaggaaaga     720
agtgatcaca aagagatgat ggaggaaccc ggagacagcc agcaacctgg gtactcccaa     780
tgggggtggc ttcttcctgg aaccagcacc gtttgtccac ctgcaaatcc tcatcctcag     840
tttggaggtg ccctctccct cccctccacg cacagctgtg acaggtaccc aaccctgagg     900
agccaccggt cctcacccta ccccagcccc tatgctcatc ggaacaattc tccaacctat     960
tctgacaact cacctgcatg tttatccatg ctgcaatccc atgacaattg gtccagcctt    1020
ggaatgcctg cccatcccag catgctcccc gtgagccaca atgccagccc acctaccagc    1080
tccagtcagt accccagcct gtggtctgtg agcaacggcg ccgtcacccc gggctcccag    1140
gcagcagccg tgtccaacgg gctgggggcc cagttcttcc ggggctcccc cgcgcactac    1200
acacccctca cccatccggt ctcggcgccc tcttcctcgg atccccact gtacgaaggg     1260 gcggccgcgg ccacagacat cgtggacagc cagtacgacg ccgcagccca aggccgcctc    1320
atagcctcat ggacacctgt gtcgccacct tccatgtga                            1359

<210> SEQ ID NO 37
<211> LENGTH: 1356
<212> TYPE: DNA
<213> ORGANISM: Artificial Sequence
<220> FEATURE:
<223> OTHER INFORMATION: Coding sequence encoding Fusion protein
      comprising Brachyury (L254V) Protein plus addition of 48
      nucleotides from Gene FPV 088 and an atc, without Brachyury atg
      start codon

<400> SEQUENCE: 37
atgaacatga gtaagaaaca agtaaaaact caaagtaaat gtaataatat cagctcccct      60
ggcaccgaga gcgcgggaaa gagcctgcag taccgagtgg accacctgct gagcgccgtg     120
gagaatgagc tgcaggcggg cagcgagaag ggcgacccca gagcgcgcga actgcgcgtg     180
ggcctggaga gagcgagct gtggctgcgc ttcaaggagc tcaccaatga gatgatcgtg     240
accaagaacg gcaggaggat gtttccggtg ctgaaggtga acgtgtctgg cctggacccc     300
aacgccatgt actccttcct gctggacttc gtggcggcgg acaaccaccg ctggaagtac     360
gtgaacgggg aatgggtgcc gggggcaag ccggagccgc aggcgcccag ctgcgtctac     420
atccaccccg actcgcccaa cttcggggcc cactggatga aggctcccgt cccttcagc     480 aaagtcaagc tcaccaacaa gctcaacgga ggggccaga tcatgctgaa ctccttgcat     540
aagtatgagc tcgaatcca catagtgaga gttggggtc acagcgcat gatcaccagc      600 cactgcttcc ctgagaccca gttcatagcg gtgactgctt atcagaacga ggagatcaca     660
gctcttaaaa ttaagtacaa tccatttgca aaggctttcc ttgatgcaaa ggaagaagt     720 gatcacaaag agatgatgga ggaacccgga cagcagc aacctgggta ctcccaatgg     780
gggtggcttc ttcctggaac cagcaccgtt tgtccacctg caaatcctca tcctcagttt     840
ggaggtgccc tctccctccc ctccacgcac agctgtgaca ggtacccaac cctgaggagc     900
caccggtcct cacctaccc cagccctat gctcatcgga caattctcc aacctattct     960 gacaactcac ctgcatgttt atccatgctg caatcccatg acaattggtc agcctttgga    1020
atgcctgccc atcccagcat gctccccgtg agccacaatg ccagcccacc taccagctcc    1080
agtcagtacc ccagcctgtg gtctgtgagc aacggcgccg tcaccccggg ctcccaggca    1140
```

```
gcagccgtgt ccaacgggct gggggcccag ttcttccggg gctcccccgc gcactacaca    1200
cccctcaccc atccggtctc ggcgccctct tcctcgggat ccccactgta cgaaggggcg    1260
gccgcggcca cagacatcgt ggacagccag tacgacgccg cagcccaagg ccgcctcata    1320
gcctcatgga cacctgtgtc gccaccttcc atgtga                              1356
```

<210> SEQ ID NO 38
<211> LENGTH: 452
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:36

<400> SEQUENCE: 38

```
Met Asn Met Ser Lys Lys Gln Val Lys Thr Gln Ser Lys Cys Asn Asn
1               5                   10                  15

Ile Met Ser Ser Pro Gly Thr Glu Ser Ala Gly Lys Ser Leu Gln Tyr
            20                  25                  30

Arg Val Asp His Leu Leu Ser Ala Val Glu Asn Glu Leu Gln Ala Gly
        35                  40                  45

Ser Glu Lys Gly Asp Pro Thr Glu Arg Glu Leu Arg Val Gly Leu Glu
    50                  55                  60

Glu Ser Glu Leu Trp Leu Arg Phe Lys Glu Leu Thr Asn Glu Met Ile
65              70                  75                  80

Val Thr Lys Asn Gly Arg Arg Met Phe Pro Val Leu Lys Val Asn Val
                85                  90                  95

Ser Gly Leu Asp Pro Asn Ala Met Tyr Ser Phe Leu Leu Asp Phe Val
            100                 105                 110

Ala Ala Asp Asn His Arg Trp Lys Tyr Val Asn Gly Glu Trp Val Pro
        115                 120                 125

Gly Gly Lys Pro Glu Pro Gln Ala Pro Ser Cys Val Tyr Ile His Pro
    130                 135                 140

Asp Ser Pro Asn Phe Gly Ala His Trp Met Lys Ala Pro Val Ser Phe
145             150                 155                 160

Ser Lys Val Lys Leu Thr Asn Lys Leu Asn Gly Gly Gly Gln Ile Met
                165                 170                 175

Leu Asn Ser Leu His Lys Tyr Glu Pro Arg Ile His Ile Val Arg Val
            180                 185                 190

Gly Gly Pro Gln Arg Met Ile Thr Ser His Cys Phe Pro Glu Thr Gln
        195                 200                 205

Phe Ile Ala Val Thr Ala Tyr Gln Asn Glu Glu Ile Thr Ala Leu Lys
    210                 215                 220

Ile Lys Tyr Asn Pro Phe Ala Lys Ala Phe Leu Asp Ala Lys Glu Arg
225             230                 235                 240

Ser Asp His Lys Glu Met Met Glu Glu Pro Gly Asp Ser Gln Gln Pro
                245                 250                 255

Gly Tyr Ser Gln Trp Gly Trp Leu Leu Pro Gly Thr Ser Thr Val Cys
            260                 265                 270

Pro Pro Ala Asn Pro His Pro Gln Phe Gly Gly Ala Leu Ser Leu Pro
        275                 280                 285

Ser Thr His Ser Cys Asp Arg Tyr Pro Thr Leu Arg Ser His Arg Ser
    290                 295                 300

Ser Pro Tyr Pro Ser Pro Tyr Ala His Arg Asn Asn Ser Pro Thr Tyr
305             310                 315                 320
```

```
Ser Asp Asn Ser Pro Ala Cys Leu Ser Met Leu Gln Ser His Asp Asn
            325                 330                 335

Trp Ser Ser Leu Gly Met Pro Ala His Pro Ser Met Leu Pro Val Ser
            340                 345                 350

His Asn Ala Ser Pro Pro Thr Ser Ser Ser Gln Tyr Pro Ser Leu Trp
            355                 360                 365

Ser Val Ser Asn Gly Ala Val Thr Pro Gly Ser Gln Ala Ala Ala Val
            370                 375                 380

Ser Asn Gly Leu Gly Ala Gln Phe Phe Arg Gly Ser Pro Ala His Tyr
385                 390                 395                 400

Thr Pro Leu Thr His Pro Val Ser Ala Pro Ser Ser Gly Ser Pro
            405                 410                 415

Leu Tyr Glu Gly Ala Ala Ala Thr Asp Ile Val Asp Ser Gln Tyr
            420                 425                 430

Asp Ala Ala Gln Gly Arg Leu Ile Ala Ser Trp Thr Pro Val Ser
            435                 440                 445

Pro Pro Ser Met
        450

<210> SEQ ID NO 39
<211> LENGTH: 451
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:37

<400> SEQUENCE: 39

Met Asn Met Ser Lys Lys Gln Val Lys Thr Gln Ser Lys Cys Asn Asn
1               5                   10                  15

Ile Ser Ser Pro Gly Thr Glu Ser Ala Gly Lys Ser Leu Gln Tyr Arg
            20                  25                  30

Val Asp His Leu Leu Ser Ala Val Glu Asn Glu Leu Gln Ala Gly Ser
            35                  40                  45

Glu Lys Gly Asp Pro Thr Glu Arg Glu Leu Arg Val Gly Leu Glu Glu
50                  55                  60

Ser Glu Leu Trp Leu Arg Phe Lys Glu Leu Thr Asn Glu Met Ile Val
65                  70                  75                  80

Thr Lys Asn Gly Arg Arg Met Phe Pro Val Leu Lys Val Asn Val Ser
            85                  90                  95

Gly Leu Asp Pro Asn Ala Met Tyr Ser Phe Leu Leu Asp Phe Val Ala
            100                 105                 110

Ala Asp Asn His Arg Trp Lys Tyr Val Asn Gly Glu Trp Val Pro Gly
            115                 120                 125

Gly Lys Pro Glu Pro Gln Ala Pro Ser Cys Val Tyr Ile His Pro Asp
            130                 135                 140

Ser Pro Asn Phe Gly Ala His Trp Met Lys Ala Pro Val Ser Phe Ser
145                 150                 155                 160

Lys Val Lys Leu Thr Asn Lys Leu Asn Gly Gly Gly Gln Ile Met Leu
            165                 170                 175

Asn Ser Leu His Lys Tyr Glu Pro Arg Ile His Ile Val Arg Val Gly
            180                 185                 190

Gly Pro Gln Arg Met Ile Thr Ser His Cys Phe Pro Glu Thr Gln Phe
            195                 200                 205

Ile Ala Val Thr Ala Tyr Gln Asn Glu Glu Ile Thr Ala Leu Lys Ile
```

```
    210                 215                 220

Lys Tyr Asn Pro Phe Ala Lys Ala Phe Leu Asp Ala Lys Glu Arg Ser
225                 230                 235                 240

Asp His Lys Glu Met Met Glu Glu Pro Gly Asp Ser Gln Gln Pro Gly
                245                 250                 255

Tyr Ser Gln Trp Gly Trp Leu Leu Pro Gly Thr Ser Thr Val Cys Pro
            260                 265                 270

Pro Ala Asn Pro His Pro Gln Phe Gly Gly Ala Leu Ser Leu Pro Ser
        275                 280                 285

Thr His Ser Cys Asp Arg Tyr Pro Thr Leu Arg Ser His Arg Ser Ser
    290                 295                 300

Pro Tyr Pro Ser Pro Tyr Ala His Arg Asn Asn Ser Pro Thr Tyr Ser
305                 310                 315                 320

Asp Asn Ser Pro Ala Cys Leu Ser Met Leu Gln Ser His Asp Asn Trp
                325                 330                 335

Ser Ser Leu Gly Met Pro Ala His Pro Ser Met Leu Pro Val Ser His
            340                 345                 350

Asn Ala Ser Pro Pro Thr Ser Ser Ser Gln Tyr Pro Ser Leu Trp Ser
        355                 360                 365

Val Ser Asn Gly Ala Val Thr Pro Gly Ser Gln Ala Ala Ala Val Ser
    370                 375                 380

Asn Gly Leu Gly Ala Gln Phe Phe Arg Gly Ser Pro Ala His Tyr Thr
385                 390                 395                 400

Pro Leu Thr His Pro Val Ser Ala Pro Ser Ser Ser Gly Ser Pro Leu
                405                 410                 415

Tyr Glu Gly Ala Ala Ala Ala Thr Asp Ile Val Asp Ser Gln Tyr Asp
            420                 425                 430

Ala Ala Ala Gln Gly Arg Leu Ile Ala Ser Trp Thr Pro Val Ser Pro
        435                 440                 445

Pro Ser Met
    450

<210> SEQ ID NO 40
<211> LENGTH: 1353
<212> TYPE: DNA
<213> ORGANISM: Artificial Sequence
<220> FEATURE:
<223> OTHER INFORMATION: Coding sequence encoding Fusion protein
      comprising Brachyury (L254V) Protein plus addition of 42
      nucleotides from Gene FPV 088 and an atc

<400> SEQUENCE: 40
atgagtaaga aacaagtaaa aactcaaagt aaatgtaata atatcatgag ctcccctggc     60
accgagagcg cgggaaagag cctgcagtac cgagtggacc acctgctgag cgccgtggag    120
aatgagctgc aggcgggcag cgagaagggc gaccccacag agcgcgaact gcgcgtgggc    180
ctggaggaga gcgagctgtg gctgcgcttc aaggagctca ccaatgagat gatcgtgacc    240
aagaacggca ggaggatgtt tccggtgctg aaggtgaacg tgtctggcct ggaccccaac    300
gccatgtact ccttcctgct ggacttcgtg gcggcggaca accaccgctg gaagtacgtg    360
aacggggaat gggtgccggg gggcaagccg gagccgcagg cgcccagctg cgtctacatc    420
caccccgact cgcccaactt cggggcccac tggatgaagg ctcccgtctc cttcagcaaa    480
gtcaagctca ccaacaagct caacggaggg ggccagatca tgctgaactc cttgcataag    540
tatgagcctc gaatccacat agtgagagtt gggggtccac agcgcatgat caccagccac    600
```

```
tgcttccctg agacccagtt catagcggtg actgcttatc agaacgagga gatcacagct    660
cttaaaatta agtacaatcc atttgcaaag gctttccttg atgcaaagga agaagtgat     720 cacaaagaga tgatggagga acccggagac agccagcaac ctgggtactc ccaatggggg    780
tggcttcttc ctggaaccag caccgtttgt ccacctgcaa atcctcatcc tcagtttgga    840
ggtgccctct ccctcccctc cacgcacagc tgtgacaggt acccaaccct gaggagccac    900
cggtcctcac cctaccccag ccctatgct catcggaaca attctccaac ctattctgac     960
aactcacctg catgtttatc catgctgcaa tcccatgaca attggtccag ccttggaatg   1020
cctgcccatc ccagcatgct ccccgtgagc acaatgcca gcccacctac cagctccagt    1080
cagtacccca gcctgtggtc tgtgagcaac ggcgccgtca ccccgggctc ccaggcagca   1140
gccgtgtcca acgggctggg ggccagttc ttccggggct cccccgcgca ctacacaccc    1200
ctcacccatc cggtctcggc gccctcttcc tcgggatccc cactgtacga aggggcggcc   1260
gcggccacag acatcgtgga cagccagtac gacgccgcag cccaaggccg cctcatagcc   1320
tcatggacac ctgtgtcgcc accttccatg tga                                 1353

<210> SEQ ID NO 41
<211> LENGTH: 1350
<212> TYPE: DNA
<213> ORGANISM: Artificial Sequence
<220> FEATURE:
<223> OTHER INFORMATION: Coding sequence encoding Fusion protein
      comprising Brachyury (L254V) Protein plus addition of 42
      nucleotides from Gene FPV 088 and an atc, without Brachyury atg
      start codon

<400> SEQUENCE: 41
atgagtaaga aacaagtaaa aactcaaagt aaatgtaata atatcagctc ccctggcacc     60
gagagcgcgg gaaagagcct gcagtaccga gtggaccacc tgctgagcgc cgtggagaat    120
gagctgcagg cgggcagcga aagggcgac cccacagagc gcgaactgcg cgtgggcctg     180
gaggagagcg agctgtggct gcgcttcaag gagctcacca tgagatgat cgtgaccaag     240 aacggcagga ggatgtttcc ggtgctgaag gtgaacgtgt ctggcctgga ccccaacgcc    300
atgtactcct tcctgctgga cttcgtggcg gcggacaacc accgctggaa gtacgtgaac    360 gggggaatggg tgccgggggg caagccggag ccgcaggcgc ccagctgcgt ctacatccac    420
cccgactcgc ccaacttcgg ggcccactgg atgaaggctc ccgtctcctt cagcaaagtc    480
aagctcacca caagctcaa cggaggggggc cagatcatgc tgaactcctt gcataagtat    540
gagcctcgaa tccacatagt gagagttggg ggtccacagc gcatgatcac cagccactgc    600
ttccctgaga cccagttcat agcggtgact gcttatcaga acgaggagat cacagctctt    660
aaaattaagt acaatccatt tgcaaaggct ttccttgatg caaaggaaag aagtgatcac    720
aaagagatga tggaggaacc cggagacagc cagcaacctg gtactccca atggggggtgg    780 cttcttcctg gaaccagcac cgtttgtcca cctgcaaatc ctcatcctca gtttggaggt    840
gccctctccc tcccctccac gcacagctgt gacaggtacc caaccctgag gagccaccgg    900
tcctcaccct accccagccc ctatgctcat cggaacaatt ctccaaccta ttctgacaac   960
tcacctgcat gtttatccat gctgcaatcc catgacaatt ggtccagcct tggaatgcct   1020
gcccatccca gcatgctccc cgtgagccac aatgccagcc acctaccag ctccagtcag   1080 taccccagcc tgtggtctgt gagcaacggc cgtcaccc cgggctccca ggcagcagcc   1140
gtgtccaacg gctggggggc ccagttcttc cggggctccc ccgcgcacta cacacccctc   1200
```

```
acccatccgg tctcggcgcc ctcttcctcg ggatccccac tgtacgaagg ggcggccgcg    1260
gccacagaca tcgtggacag ccagtacgac gccgcagccc aaggccgcct catagcctca    1320
tggacacctg tgtcgccacc ttccatgtga                                     1350
```

<210> SEQ ID NO 42
<211> LENGTH: 450
<212> TYPE: PRT
<213> ORGANISM: Artificial Sequence
<220> FEATURE:
<223> OTHER INFORMATION: Fusion protein comprising Brachyury (L254V)
       Protein encoded by SEQ ID NO:40

<400> SEQUENCE: 42

```
Met Ser Lys Lys Gln Val Lys Thr Gln Ser Lys Cys Asn Asn Ile Met
1               5                   10                  15

Ser Ser Pro Gly Thr Glu Ser Ala Gly Lys Ser Leu Gln Tyr Arg Val
            20                  25                  30

Asp His Leu Leu Ser Ala Val Glu Asn Glu Leu Gln Ala Gly Ser Glu
        35                  40                  45

Lys Gly Asp Pro Thr Glu Arg Glu Leu Arg Val Gly Leu Glu Glu Ser
    50                  55                  60

Glu Leu Trp Leu Arg Phe Lys Glu Leu Thr Asn Glu Met Ile Val Thr
65                  70                  75                  80

Lys Asn Gly Arg Arg Met Phe Pro Val Leu Lys Val Asn Val Ser Gly
                85                  90                  95

Leu Asp Pro Asn Ala Met Tyr Ser Phe Leu Leu Asp Phe Val Ala Ala
            100                 105                 110

Asp Asn His Arg Trp Lys Tyr Val Asn Gly Glu Trp Val Pro Gly Gly
        115                 120                 125

Lys Pro Glu Pro Gln Ala Pro Ser Cys Val Tyr Ile His Pro Asp Ser
    130                 135                 140

Pro Asn Phe Gly Ala His Trp Met Lys Ala Pro Val Ser Phe Ser Lys
145                 150                 155                 160

Val Lys Leu Thr Asn Lys Leu Asn Gly Gly Gly Gln Ile Met Leu Asn
                165                 170                 175

Ser Leu His Lys Tyr Glu Pro Arg Ile His Ile Val Arg Val Gly Gly
            180                 185                 190

Pro Gln Arg Met Ile Thr Ser His Cys Phe Pro Glu Thr Gln Phe Ile
        195                 200                 205

Ala Val Thr Ala Tyr Gln Asn Glu Glu Ile Thr Ala Leu Lys Ile Lys
    210                 215                 220

Tyr Asn Pro Phe Ala Lys Ala Phe Leu Asp Ala Lys Glu Arg Ser Asp
225                 230                 235                 240

His Lys Glu Met Met Glu Glu Pro Gly Asp Ser Gln Gln Pro Gly Tyr
                245                 250                 255

Ser Gln Trp Gly Trp Leu Leu Pro Gly Thr Ser Thr Val Cys Pro Pro
            260                 265                 270

Ala Asn Pro His Pro Gln Phe Gly Gly Ala Leu Ser Leu Pro Ser Thr
        275                 280                 285

His Ser Cys Asp Arg Tyr Pro Thr Leu Arg Ser His Arg Ser Ser Pro
    290                 295                 300

Tyr Pro Ser Pro Tyr Ala His Arg Asn Asn Ser Pro Thr Tyr Ser Asp
305                 310                 315                 320

Asn Ser Pro Ala Cys Leu Ser Met Leu Gln Ser His Asp Asn Trp Ser
                325                 330                 335
```

```
Ser Leu Gly Met Pro Ala His Pro Ser Met Leu Pro Val Ser His Asn
            340                 345                 350

Ala Ser Pro Pro Thr Ser Ser Gln Tyr Pro Ser Leu Trp Ser Val
            355                 360                 365

Ser Asn Gly Ala Val Thr Pro Gly Ser Gln Ala Ala Val Ser Asn
    370                 375                 380

Gly Leu Gly Ala Gln Phe Phe Arg Gly Ser Pro Ala His Tyr Thr Pro
385                 390                 395                 400

Leu Thr His Pro Val Ser Ala Pro Ser Ser Gly Ser Pro Leu Tyr
                405                 410                 415

Glu Gly Ala Ala Ala Thr Asp Ile Val Asp Ser Gln Tyr Asp Ala
            420                 425                 430

Ala Ala Gln Gly Arg Leu Ile Ala Ser Trp Thr Pro Val Ser Pro Pro
            435                 440                 445

Ser Met
    450

<210> SEQ ID NO 43
<211> LENGTH: 449
<212> TYPE: PRT
<213> ORGANISM: Artificial Sequence
<220> FEATURE:
<223> OTHER INFORMATION: Fusion protein comprising Brachyury (L254V)
      Protein encoded by SEQ ID NO:41

<400> SEQUENCE: 43

Met Ser Lys Lys Gln Val Lys Thr Gln Ser Lys Cys Asn Asn Ile Ser
1               5                   10                  15

Ser Pro Gly Thr Glu Ser Ala Gly Lys Ser Leu Gln Tyr Arg Val Asp
            20                  25                  30

His Leu Leu Ser Ala Val Glu Asn Glu Leu Gln Ala Gly Ser Glu Lys
        35                  40                  45

Gly Asp Pro Thr Glu Arg Glu Leu Arg Val Gly Leu Glu Glu Ser Glu
    50                  55                  60

Leu Trp Leu Arg Phe Lys Glu Leu Thr Asn Glu Met Ile Val Thr Lys
65                  70                  75                  80

Asn Gly Arg Arg Met Phe Pro Val Leu Lys Val Asn Val Ser Gly Leu
                85                  90                  95

Asp Pro Asn Ala Met Tyr Ser Phe Leu Leu Asp Phe Val Ala Ala Asp
            100                 105                 110

Asn His Arg Trp Lys Tyr Val Asn Gly Glu Trp Val Pro Gly Gly Lys
        115                 120                 125

Pro Glu Pro Gln Ala Pro Ser Cys Val Tyr Ile His Pro Asp Ser Pro
    130                 135                 140

Asn Phe Gly Ala His Trp Met Lys Ala Pro Val Ser Phe Ser Lys Val
145                 150                 155                 160

Lys Leu Thr Asn Lys Leu Asn Gly Gly Gly Gln Ile Met Leu Asn Ser
                165                 170                 175

Leu His Lys Tyr Glu Pro Arg Ile His Ile Val Arg Val Gly Gly Pro
            180                 185                 190

Gln Arg Met Ile Thr Ser His Cys Phe Pro Glu Thr Gln Phe Ile Ala
        195                 200                 205

Val Thr Ala Tyr Gln Asn Glu Glu Ile Thr Ala Leu Lys Ile Lys Tyr
    210                 215                 220

Asn Pro Phe Ala Lys Ala Phe Leu Asp Ala Lys Glu Arg Ser Asp His
```

```
                   225                 230                 235                 240
Lys Glu Met Met Glu Glu Pro Gly Asp Ser Gln Gln Pro Gly Tyr Ser
                245                 250                 255

Gln Trp Gly Trp Leu Leu Pro Gly Thr Ser Thr Val Cys Pro Pro Ala
                260                 265                 270

Asn Pro His Pro Gln Phe Gly Gly Ala Leu Ser Leu Pro Ser Thr His
                275                 280                 285

Ser Cys Asp Arg Tyr Pro Thr Leu Arg Ser His Arg Ser Ser Pro Tyr
            290                 295                 300

Pro Ser Pro Tyr Ala His Arg Asn Asn Ser Pro Thr Tyr Ser Asp Asn
305                 310                 315                 320

Ser Pro Ala Cys Leu Ser Met Leu Gln Ser His Asp Asn Trp Ser Ser
                325                 330                 335

Leu Gly Met Pro Ala His Pro Ser Met Leu Pro Val Ser His Asn Ala
                340                 345                 350

Ser Pro Pro Thr Ser Ser Ser Gln Tyr Pro Ser Leu Trp Ser Val Ser
                355                 360                 365

Asn Gly Ala Val Thr Pro Gly Ser Gln Ala Ala Val Ser Asn Gly
            370                 375                 380

Leu Gly Ala Gln Phe Phe Arg Gly Ser Pro Ala His Tyr Thr Pro Leu
385                 390                 395                 400

Thr His Pro Val Ser Ala Pro Ser Ser Gly Ser Pro Leu Tyr Glu
                405                 410                 415

Gly Ala Ala Ala Ala Thr Asp Ile Val Asp Ser Gln Tyr Asp Ala Ala
                420                 425                 430

Ala Gln Gly Arg Leu Ile Ala Ser Trp Thr Pro Val Ser Pro Pro Ser
            435                 440                 445
Met

<210> SEQ ID NO 44
<211> LENGTH: 1323
<212> TYPE: DNA
<213> ORGANISM: Artificial Sequence
<220> FEATURE:
<223> OTHER INFORMATION: Coding sequence encoding fusion protein
      comprising Brachyury protein Isoform 1 plus addition of 15
      nucleotides from Gene FPV 088

<400> SEQUENCE: 44
atgaaaaata acttgatgag ctcccctggc accgagagcg cgggaaagag cctgcagtac     60
cgagtggacc acctgctgag cgccgtggag aatgagctgc aggcgggcag cgagaagggc    120
gaccccacag agcgcgaact gcgcgtgggc ctggaggaga gcgagctgtg gctgcgcttc    180
aaggagctca ccaatgagat gatcgtgacc aagaacggca ggaggatgtt ccggtgctg     240 aaggtgaacg tgtctggcct ggaccccaac gccatgtact ccttcctgct ggacttcgtg    300
gcggcggaca ccaccgctg gaagtacgtg aacggggaat gggtgccggg ggcaagccg      360 gagccgcagg cgcccagctg cgtctacatc caccccgact cgcccaactt cggggcccac    420
tggatgaagg ctcccgtctc cttcagcaaa gtcaagctca ccaacaagct caacggaggg    480
ggccagatca tgctgaactc cttgcataag tatgagcctc gaatccacat agtgagagtt    540
gggggtccac agcgcatgat caccagccac tgcttccctg agacccagtt catagcggtg    600
actgcttatc agaacgagga gatcacagct cttaaaatta gtacaatcc atttgcaaaa    660 gctttccttg atgcaaagga agaagtgat cacaaagaga tgatggagga acccggagac    720
```

-continued

| | |
|---|---|
| agccagcaac ctgggtactc ccaatggggg tggcttcttc ctggaaccag caccgtttgt | 780 |
| ccacctgcaa atcctcatcc tcagtttgga ggtgccctct ccctcccctc cacgcacagc | 840 |
| tgtgacaggt acccaaccct gaggagccac cggtcctcac cctaccccag ccctatgct | 900 |
| catcggaaca attctccaac ctattctgac aactcacctg catgtttatc catgctgcaa | 960 |
| tcccatgaca attggtccag ccttggaatg cctgcccatc ccagcatgct cccgtgagc | 1020 |
| cacaatgcca gcccacctac cagctccagt cagtacccca gcctgtggtc tgtgagcaac | 1080 |
| ggcgccgtca ccccgggctc ccaggcagca gccgtgtcca acgggctggg ggcccagttc | 1140 |
| ttccgggggct cccccgcgca ctacacaccc ctcacccatc cggtctcggc gccctcttcc | 1200 |
| tcgggatccc cactgtacga aggggcggcc gcggccacag acatcgtgga cagccagtac | 1260 |
| gacgccgcag cccaaggccg cctcatagcc tcatggacac ctgtgtcgcc accttccatg | 1320 |
| tga | 1323 |

<210> SEQ ID NO 45
<211> LENGTH: 1320
<212> TYPE: DNA
<213> ORGANISM: Artificial Sequence
<220> FEATURE:
<223> OTHER INFORMATION: Coding sequence encoding fusion protein
comprising Brachyury protein Isoform 1 plus addition of 15
nucleotides from Gene FPV 088 without Brachyury protein atg start
codon

<400> SEQUENCE: 45

| | |
|---|---|
| atgaaaaata acttgagctc ccctggcacc gagagcgcgg gaaagagcct gcagtaccga | 60 |
| gtggaccacc tgctgagcgc cgtggagaat gagctgcagg cgggcagcga aagggcgac | 120 |
| cccacagagc gcgaactgcg cgtgggcctg gaggagagcg agctgtggct gcgcttcaag | 180 |
| gagctcacca atgagatgat cgtgaccaag aacggcagga ggatgtttcc ggtgctgaag | 240 |
| gtgaacgtgt ctggcctgga ccccaacgcc atgtactcct tcctgctgga cttcgtggcg | 300 |
| gcggacaacc accgctggaa gtacgtgaac ggggaatggg tgccgggggg caagccggag | 360 |
| ccgcaggcgc ccagctgcgt ctacatccac cccgactcgc caacttcgg ggcccactgg | 420 |
| atgaaggctc ccgtctcctt cagcaaagtc aagctcacca caagctcaa cggagggggc | 480 |
| cagatcatgc tgaactcctt gcataagtat gagcctcgaa tccacatagt gagagttggg | 540 |
| ggtccacagc gcatgatcac cagccactgc ttccctgaga cccagttcat agcggtgact | 600 |
| gcttatcaga acgaggagat cacagctctt aaaattaagt acaatccatt tgcaaaagct | 660 |
| ttccttgatg caaaggaaag aagtgatcac aaagagatga tggaggaacc cggagacagc | 720 |
| cagcaacctg gtactcccca atggggggtg cttcttcctg gaaccagcac cgtttgtcca | 780 |
| cctgcaaatc ctcatcctca gtttggaggt gccctctccc tccctccac gcacagctgt | 840 |
| gacaggtacc caaccctgag gagccaccgg tcctcaccct accccagccc ctatgctcat | 900 |
| cggaacaatt ctccaaccta ttctgacaac tcacctgcat gtttatccat gctgcaatcc | 960 |
| catgacaatt ggtccagcct tggaatgcct gcccatccca gcatgctccc gtgagccac | 1020 |
| aatgccagcc cacctaccag ctccagtcag taccccagcc tgtggtctgt gagcaacggc | 1080 |
| gccgtcaccc cgggctccca ggcagcagcc gtgtccaacg gctgggggc cagttcttc | 1140 |
| cggggctccc ccgcgcacta cacacccctc acccatccgg tctcggcgcc ctcttcctcg | 1200 |
| ggatccccac tgtacgaagg ggcggccgcg gccacagaca tcgtgacag ccagtacgac | 1260 |
| gccgcagccc aaggccgcct catagcctca tggacacctg tgtcgccacc ttccatgtga | 1320 |

<210> SEQ ID NO 46
<211> LENGTH: 440
<212> TYPE: PRT
<213> ORGANISM: Artificial Sequence
<220> FEATURE:
<223> OTHER INFORMATION: Fusion protein comprising Brachyury protein Isoform 1 encoded by SEQ ID NO:44

<400> SEQUENCE: 46

```
Met Lys Asn Asn Leu Met Ser Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Gly Pro Gln Arg Met Ile Thr Ser His Cys Phe
            180                 185                 190

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Leu Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
        275                 280                 285

Ser His Arg Ser Ser Pro Tyr Pro Ser Pro Tyr Ala His Arg Asn Asn
290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
        355                 360                 365
```

```
Ala Ala Ala Val Ser Asn Gly Leu Gly Ala Gln Phe Phe Arg Gly Ser
            370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Thr Asp Ile Val
                405                 410                 415

Asp Ser Gln Tyr Asp Ala Ala Ala Gln Gly Arg Leu Ile Ala Ser Trp
            420                 425                 430

Thr Pro Val Ser Pro Pro Ser Met
            435                 440

<210> SEQ ID NO 47
<211> LENGTH: 439
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:45

<400> SEQUENCE: 47

Met Lys Asn Asn Leu Ser Ser Pro Gly Thr Glu Ser Ala Gly Lys Ser
1               5                   10                  15

Leu Gln Tyr Arg Val Asp His Leu Leu Ser Ala Val Glu Asn Glu Leu
            20                  25                  30

Gln Ala Gly Ser Glu Lys Gly Asp Pro Thr Glu Arg Glu Leu Arg Val
        35                  40                  45

Gly Leu Glu Glu Ser Glu Leu Trp Leu Arg Phe Lys Glu Leu Thr Asn
    50                  55                  60

Glu Met Ile Val Thr Lys Asn Gly Arg Arg Met Phe Pro Val Leu Lys
65                  70                  75                  80

Val Asn Val Ser Gly Leu Asp Pro Asn Ala Met Tyr Ser Phe Leu Leu
                85                  90                  95

Asp Phe Val Ala Ala Asp Asn His Arg Trp Lys Tyr Val Asn Gly Glu
            100                 105                 110

Trp Val Pro Gly Gly Lys Pro Glu Pro Gln Ala Pro Ser Cys Val Tyr
        115                 120                 125

Ile His Pro Asp Ser Pro Asn Phe Gly Ala His Trp Met Lys Ala Pro
    130                 135                 140

Val Ser Phe Ser Lys Val Lys Leu Thr Asn Lys Leu Asn Gly Gly Gly
145                 150                 155                 160

Gln Ile Met Leu Asn Ser Leu His Lys Tyr Glu Pro Arg Ile His Ile
                165                 170                 175

Val Arg Val Gly Gly Pro Gln Arg Met Ile Thr Ser His Cys Phe Pro
            180                 185                 190

Glu Thr Gln Phe Ile Ala Val Thr Ala Tyr Gln Asn Glu Glu Ile Thr
        195                 200                 205

Ala Leu Lys Ile Lys Tyr Asn Pro Phe Ala Lys Ala Phe Leu Asp Ala
    210                 215                 220

Lys Glu Arg Ser Asp His Lys Glu Met Met Glu Glu Pro Gly Asp Ser
225                 230                 235                 240

Gln Gln Pro Gly Tyr Ser Gln Trp Gly Trp Leu Leu Pro Gly Thr Ser
                245                 250                 255

Thr Leu Cys Pro Pro Ala Asn Pro His Pro Gln Phe Gly Gly Ala Leu
            260                 265                 270

Ser Leu Pro Ser Thr His Ser Cys Asp Arg Tyr Pro Thr Leu Arg Ser
```

-continued

```
        275                 280                 285

His Arg Ser Ser Pro Tyr Pro Ser Pro Tyr Ala His Arg Asn Asn Ser
    290                 295                 300
Pro Thr Tyr Ser Asp Asn Ser Pro Ala Cys Leu Ser Met Leu Gln Ser
305                 310                 315                 320
His Asp Asn Trp Ser Ser Leu Gly Met Pro Ala His Pro Ser Met Leu
                325                 330                 335
Pro Val Ser His Asn Ala Ser Pro Pro Thr Ser Ser Ser Gln Tyr Pro
            340                 345                 350

Ser Leu Trp Ser Val Ser Asn Gly Ala Val Thr Pro Gly Ser Gln Ala
        355                 360                 365

Ala Ala Val Ser Asn Gly Leu Gly Ala Gln Phe Phe Arg Gly Ser Pro
    370                 375                 380
Ala His Tyr Thr Pro Leu Thr His Pro Val Ser Ala Pro Ser Ser Ser
385                 390                 395                 400

Gly Ser Pro Leu Tyr Glu Gly Ala Ala Ala Ala Thr Asp Ile Val Asp
                405                 410                 415
Ser Gln Tyr Asp Ala Ala Ala Gln Gly Arg Leu Ile Ala Ser Trp Thr
            420                 425                 430

Pro Val Ser Pro Pro Ser Met
        435
```

<210> SEQ ID NO 48
<211> LENGTH: 1353
<212> TYPE: DNA
<213> ORGANISM: Artificial Sequence
<220> FEATURE:
<223> OTHER INFORMATION: Coding sequence encoding fusion protein comprising Brachyury protein Isoform 1 plus addition of 45 nucleotides from Gene FPV 088

<400> SEQUENCE: 48

```
atgaaaaata acttgtatga agaaaaaatg aacatgagta agaaaatgag ctcccctggc     60
accgagagcg cgggaaagag cctgcagtac cgagtggacc acctgctgag cgccgtggag    120
aatgagctgc aggcgggcag cgagaagggc gaccccacag agcgcgaact gcgcgtgggc    180
ctggaggaga gcgagctgtg gctgcgcttc aaggagctca ccaatgagat gatcgtgacc    240
aagaacggca ggaggatgtt tccggtgctg aaggtgaacg tgtctggcct ggaccccaac    300
gccatgtact ccttcctgct ggacttcgtg gcggcggaca accaccgctg gaagtacgtg    360
aacggggaat gggtgccggg gggcaagccg gagccgcagg cgcccagctg cgtctacatc    420
caccccgact cgcccaactt cggggcccac tggatgaagg ctcccgtctc cttcagcaaa    480
gtcaagctca ccaacaagct caacggaggg ggccagatca tgctgaactc cttgcataag    540
tatgagcctc gaatccacat agtgagagtt gggggtccac agcgcatgat caccagccac    600
tgcttccctg agacccagtt catagcggtg actgcttatc agaacgagga gatcacagct    660
cttaaaatta agtacaatcc atttgcaaag gctttccttg atgcaaagga aagaagtgat    720
cacaaagaga tgatggagga acccggagac agccagcaac ctgggtactc ccaatggggg    780
tggcttcttc ctggaaccag caccgtttgt ccacctgcaa atcctcatcc tcagtttgga    840
ggtgccctct ccctcccctc cacgcacagc tgtgacaggt acccaaccct gaggagccac    900
cggtcctcac cctaccccag cccctatgct catcggaaca attctccaac ctattctgac    960
aactcacctg catgtttatc catgctgcaa tcccatgaca attggtccag ccttggaatg   1020
cctgcccatc ccagcatgct ccccgtgagc cacaatgcca gcccacctac cagctccagt   1080
```

```
cagtacccca gcctgtggtc tgtgagcaac ggcgccgtca ccccgggctc ccaggcagca   1140
gccgtgtcca acgggctggg ggcccagttc ttccggggct cccccgcgca ctacacaccc   1200
ctcacccatc cggtctcggc gccctcttcc tcgggatccc cactgtacga aggggcggcc   1260
gcggccacag acatcgtgga cagccagtac gacgccgcag cccaaggccg cctcatagcc   1320
tcatggacac ctgtgtcgcc accttccatg tga                               1353
```

<210> SEQ ID NO 49
<211> LENGTH: 1350
<212> TYPE: DNA
<213> ORGANISM: Artificial Sequence
<220> FEATURE:
<223> OTHER INFORMATION: Coding sequence encoding fusion protein
     comprising Brachyury protein Isoform 1 plus addition of 45
     nucleotides from Gene FPV 088 without Brachyury atg

<400> SEQUENCE: 49

```
atgaaaaata acttgtatga agaaaaaatg aacatgagta agaaaagctc ccctggcacc     60
gagagcgcgg gaaagagcct gcagtaccga gtggaccacc tgctgagcgc cgtggagaat    120
gagctgcagg cggcagcga gaagggcgac cccacagagc gcgaactgcg cgtgggcctg    180
gaggagagcg agctgtggct gcgcttcaag gagctcacca atgagatgat cgtgaccaag    240
aacggcagga ggatgtttcc ggtgctgaag gtgaacgtgt ctggcctgga ccccaacgcc    300
atgtactcct tcctgctgga cttcgtggcg gcggacaacc accgctggaa gtacgtgaac    360
ggggaatggg tgccgggggg caagccgag ccgcaggcgc ccagctgcgt ctacatccac    420
cccgactcgc ccaacttcgg ggcccactgg atgaaggctc ccgtctcctt cagcaaagtc    480
aagctcacca acaagctcaa cggagggggc cagatcatgc tgaactcctt gcataagtat    540
gagcctcgaa tccacatagt gagagttggg ggtccacagc gcatgatcac cagccactgc    600
ttccctgaga cccagttcat agcggtgact gcttatcaga cgaggagat cacagctctt    660 aaaattaagt acaatccatt tgcaaaagct ttccttgatg caaaggaaag aagtgatcac    720
aaagagatga tggaggaacc cggagacagc cagcaacctg ggtactccca atggggggtgg    780 cttcttcctg gaaccagcac cgtttgtcca cctgcaaatc ctcatcctca gtttggaggt    840
gccctctccc tccctccac gcacagctgt gacaggtacc caaccctgag gagccaccgg    900 tcctcacccct accccagccc ctatgctcat cggaacaatt ctccaaccta ttctgacaac    960
tcacctgcat gtttatccat gctgcaatcc atgacaatt ggtccagcct tggaatgcct   1020
gcccatccca gcatgctccc cgtgagccac aatgccagcc acctaccag ctccagtcag   1080 taccccagcc tgtggtctgt gagcaacggc gccgtcaccc cgggctccca ggcagcagcc   1140
gtgtccaacg gctggggcgc cagttcttc cggggctccc ccgcgcacta cacacccctc   1200
acccatccgg tctcggcgcc ctcttcctcg gatccccac tgtacgaagg ggcggccgcg   1260
gccacagaca tcgtggacag ccagtacgac gccgcagccc aaggccgcct catagcctca   1320
tggacacctg tgtcgccacc ttccatgtga                                    1350
```

<210> SEQ ID NO 50
<211> LENGTH: 450
<212> TYPE: PRT
<213> ORGANISM: Artificial Sequence
<220> FEATURE:
<223> OTHER INFORMATION: Fusion protein comprising Brachyury protein
     Isoform 1 encoded by SEQ ID NO:48

<400> SEQUENCE: 50

```
Met Lys Asn Asn Leu Tyr Glu Glu Lys Met Asn Met Ser Lys Met
1               5                   10                  15

Ser Ser Pro Gly Thr Glu Ser Ala Gly Lys Ser Leu Gln Tyr Arg Val
            20                  25                  30

Asp His Leu Leu Ser Ala Val Glu Asn Glu Leu Gln Ala Gly Ser Glu
            35                  40                  45

Lys Gly Asp Pro Thr Glu Arg Glu Leu Arg Val Gly Leu Glu Glu Ser
        50                  55                  60

Glu Leu Trp Leu Arg Phe Lys Glu Leu Thr Asn Glu Met Ile Val Thr
65                  70                  75                  80

Lys Asn Gly Arg Arg Met Phe Pro Val Leu Lys Val Asn Val Ser Gly
                85                  90                  95

Leu Asp Pro Asn Ala Met Tyr Ser Phe Leu Leu Asp Phe Val Ala Ala
                100                 105                 110

Asp Asn His Arg Trp Lys Tyr Val Asn Gly Glu Trp Val Pro Gly Gly
            115                 120                 125

Lys Pro Glu Pro Gln Ala Pro Ser Cys Val Tyr Ile His Pro Asp Ser
        130                 135                 140

Pro Asn Phe Gly Ala His Trp Met Lys Ala Pro Val Ser Phe Ser Lys
145                 150                 155                 160

Val Lys Leu Thr Asn Lys Leu Asn Gly Gly Gln Ile Met Leu Asn
                165                 170                 175

Ser Leu His Lys Tyr Glu Pro Arg Ile His Ile Val Arg Val Gly Gly
            180                 185                 190

Pro Gln Arg Met Ile Thr Ser His Cys Phe Pro Glu Thr Gln Phe Ile
        195                 200                 205

Ala Val Thr Ala Tyr Gln Asn Glu Glu Ile Thr Ala Leu Lys Ile Lys
        210                 215                 220

Tyr Asn Pro Phe Ala Lys Ala Phe Leu Asp Ala Lys Glu Arg Ser Asp
225                 230                 235                 240

His Lys Glu Met Met Glu Glu Pro Gly Asp Ser Gln Gln Pro Gly Tyr
                245                 250                 255

Ser Gln Trp Gly Trp Leu Leu Pro Gly Thr Ser Thr Leu Cys Pro Pro
            260                 265                 270

Ala Asn Pro His Pro Gln Phe Gly Gly Ala Leu Ser Leu Pro Ser Thr
        275                 280                 285

His Ser Cys Asp Arg Tyr Pro Thr Leu Arg Ser His Arg Ser Ser Pro
        290                 295                 300

Tyr Pro Ser Pro Tyr Ala His Arg Asn Asn Ser Pro Thr Tyr Ser Asp
305                 310                 315                 320

Asn Ser Pro Ala Cys Leu Ser Met Leu Gln Ser His Asp Asn Trp Ser
                325                 330                 335

Ser Leu Gly Met Pro Ala His Pro Ser Met Leu Pro Val Ser His Asn
            340                 345                 350

Ala Ser Pro Pro Thr Ser Ser Gln Tyr Pro Ser Leu Trp Ser Val
        355                 360                 365

Ser Asn Gly Ala Val Thr Pro Gly Ser Gln Ala Ala Val Ser Asn
370                 375                 380

Gly Leu Gly Ala Gln Phe Phe Arg Gly Ser Pro Ala His Tyr Thr Pro
385                 390                 395                 400

Leu Thr His Pro Val Ser Ala Pro Ser Ser Ser Gly Ser Pro Leu Tyr
            405                 410                 415
```

```
Glu Gly Ala Ala Ala Ala Thr Asp Ile Val Asp Ser Gln Tyr Asp Ala
                420                 425                 430

Ala Ala Gln Gly Arg Leu Ile Ala Ser Trp Thr Pro Val Ser Pro Pro
            435                 440                 445

Ser Met
    450

<210> SEQ ID NO 51
<211> LENGTH: 449
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:49

<400> SEQUENCE: 51

Met Lys Asn Asn Leu Tyr Glu Glu Lys Met Asn Met Ser Lys Lys Ser
1               5                   10                  15

Ser Pro Gly Thr Glu Ser Ala Gly Lys Ser Leu Gln Tyr Arg Val Asp
            20                  25                  30

His Leu Leu Ser Ala Val Glu Asn Glu Leu Gln Ala Gly Ser Glu Lys
        35                  40                  45

Gly Asp Pro Thr Glu Arg Glu Leu Arg Val Gly Leu Glu Glu Ser Glu
    50                  55                  60

Leu Trp Leu Arg Phe Lys Glu Leu Thr Asn Glu Met Ile Val Thr Lys
65                  70                  75                  80

Asn Gly Arg Arg Met Phe Pro Val Leu Lys Val Asn Val Ser Gly Leu
                85                  90                  95

Asp Pro Asn Ala Met Tyr Ser Phe Leu Leu Asp Phe Val Ala Ala Asp
            100                 105                 110

Asn His Arg Trp Lys Tyr Val Asn Gly Glu Trp Val Pro Gly Gly Lys
        115                 120                 125

Pro Glu Pro Gln Ala Pro Ser Cys Val Tyr Ile His Pro Asp Ser Pro
    130                 135                 140

Asn Phe Gly Ala His Trp Met Lys Ala Pro Val Ser Phe Ser Lys Val
145                 150                 155                 160

Lys Leu Thr Asn Lys Leu Asn Gly Gly Gly Gln Ile Met Leu Asn Ser
                165                 170                 175

Leu His Lys Tyr Glu Pro Arg Ile His Ile Val Arg Val Gly Gly Pro
            180                 185                 190

Gln Arg Met Ile Thr Ser His Cys Phe Pro Glu Thr Gln Phe Ile Ala
        195                 200                 205

Val Thr Ala Tyr Gln Asn Glu Glu Ile Thr Ala Leu Lys Ile Lys Tyr
    210                 215                 220

Asn Pro Phe Ala Lys Ala Phe Leu Asp Ala Lys Glu Arg Ser Asp His
225                 230                 235                 240

Lys Glu Met Met Glu Glu Pro Gly Asp Ser Gln Gln Pro Gly Tyr Ser
                245                 250                 255

Gln Trp Gly Trp Leu Leu Pro Gly Thr Ser Thr Leu Cys Pro Pro Ala
            260                 265                 270

Asn Pro His Pro Gln Phe Gly Gly Ala Leu Ser Leu Pro Ser Thr His
        275                 280                 285

Ser Cys Asp Arg Tyr Pro Thr Leu Arg Ser His Arg Ser Ser Pro Tyr
    290                 295                 300

Pro Ser Pro Tyr Ala His Arg Asn Asn Ser Pro Thr Tyr Ser Asp Asn
305                 310                 315                 320
```

```
Ser Pro Ala Cys Leu Ser Met Leu Gln Ser His Asp Asn Trp Ser Ser
            325                 330                 335

Leu Gly Met Pro Ala His Pro Ser Met Leu Pro Val Ser His Asn Ala
        340                 345                 350

Ser Pro Pro Thr Ser Ser Ser Gln Tyr Pro Ser Leu Trp Ser Val Ser
            355                 360                 365

Asn Gly Ala Val Thr Pro Gly Ser Gln Ala Ala Val Ser Asn Gly
        370                 375                 380

Leu Gly Ala Gln Phe Phe Arg Gly Ser Pro Ala His Tyr Thr Pro Leu
385                 390                 395                 400

Thr His Pro Val Ser Ala Pro Ser Ser Gly Ser Pro Leu Tyr Glu
            405                 410                 415

Gly Ala Ala Ala Ala Thr Asp Ile Val Asp Ser Gln Tyr Asp Ala Ala
            420                 425                 430

Ala Gln Gly Arg Leu Ile Ala Ser Trp Thr Pro Val Ser Pro Pro Ser
            435                 440                 445

Met
```

<210> SEQ ID NO 52
<211> LENGTH: 1326
<212> TYPE: DNA
<213> ORGANISM: Artificial Sequence
<220> FEATURE:
<223> OTHER INFORMATION: Coding sequence encoding fusion protein
      comprising Brachyury protein Isoform 1 plus addition of 18
      nucleotides from Gene FPV 088

<400> SEQUENCE: 52

```
atgaacatga gtaagaaaat gagctcccct ggcaccgaga gcgcgggaaa gagcctgcag    60
taccgagtgg accacctgct gagcgccgtg gagaatgagc tgcaggcggg cagcgagaag   120
ggcgacccca cagagcgcga actgcgcgtg ggcctggagg agagcgagct gtggctgcgc   180
ttcaaggagc tcaccaatga tgatcgtg accaagaacg caggaggat gtttccggtg    240 ctgaaggtga acgtgtctgg cctggacccc aacgccatgt actccttcct gctggacttc   300
gtggcggcgg acaaccaccg ctggaagtac gtgaacgggg aatgggtgcc ggggggcaag   360
ccggagccgc aggcgcccag ctgcgtctac atccaccccg actcgcccaa cttcggggcc   420
cactggatga aggctcccgt ctccttcagc aaagtcaagc tcaccaacaa gctcaacgga   480
gggggccaga tcatgctgaa ctccttgcat aagtatgagc tcgaatcca catagtgaga   540 gttggggggtc cacagcgcat gatcaccagc cactgcttcc ctgagaccca gttcatagcg   600
gtgactgctt atcagaacga ggagatcaca gctcttaaaa ttaagtacaa tccatttgca   660
aaggcttttc ttgatgcaaa ggaaagaagt gatcacaaag atgatggag ggaacccgga    720 gacagccagc aacctgggta ctcccaatgg gggtggcttc ttcctggaac cagcaccgtt   780
tgtccacctg caaatcctca tcctcagttt ggaggtgccc tctcctccc ctccacgcac   840 agctgtgaca ggtacccaac cctgaggagc accggtcct caccctaccc cagcccctat   900
gctcatcgga caattctcc aacctattct gacaactcac ctgcatgttt atccatgctg   960
caatcccatg acaattggtc cagccttgga atgcctgccc atcccagcat gctccccgtg  1020
agccacaatg ccagcccacc taccagctcc agtcagtacc cagcctgtg gtctgtgagc  1080 aacggcgccg tcaccccggg ctcccaggca gcagccgtgt ccaacgggct ggggccgcag  1140
ttcttccggg gctcccccgc gcactacaca cccctcaccc atccggtctc ggcgccctct  1200
```

```
tcctcgggat ccccactgta cgaaggggcg gccgcggcca cagacatcgt ggacagccag    1260
tacgacgccg cagcccaagg ccgcctcata gcctcatgga cacctgtgtc gccaccttcc    1320
atgtga                                                               1326

<210> SEQ ID NO 53
<211> LENGTH: 1323
<212> TYPE: DNA
<213> ORGANISM: Artificial Sequence
<220> FEATURE:
<223> OTHER INFORMATION: Coding sequence encoding fusion protein
      comprising Brachyury protein Isoform 1 plus addition of 18
      nucleotides from Gene FPV 088 without brachyury atg

<400> SEQUENCE: 53
atgaacatga gtaagaaaag ctcccctggc accgagagcg cgggaaagag cctgcagtac      60
cgagtggacc acctgctgag cgccgtggag aatgagctgc aggcgggcag cgagaagggc     120
gaccccacag agcgcgaact gcgcgtgggc ctggaggaga gcgagctgtg gctgcgcttc     180
aaggagctca ccaatgagat gatcgtgacc aagaacggca ggaggatgtt ccggtgctg      240 aaggtgaacg tgtctggcct ggaccccaac gccatgtact ccttcctgct ggacttcgtg     300
gcggcggaca ccaccgctg gaagtacgtg acgggggaat gggtgccggg gggcaagccg      360
gagccgcagg cgcccagctg cgtctacatc caccccgact cgcccaactt cggggcccac     420
tggatgaagg ctcccgtctc cttcagcaaa gtcaagctca ccaacaagct caacggaggg     480
ggccagatca tgctgaactc cttgcataag tatgagcctc gaatccacat agtgagagtt     540
gggggtccac agcgcatgat caccagccac tgcttccctg agacccagtt catagcggtg     600
actgcttatc agaacgagga gatcacagct cttaaaatta gtacaatcc atttgcaaaa      660 gctttccttg atgcaaagga aagaagtgat cacaaagaga tgatggagga acccggagac     720
agccagcaac tgggtactc ccaatggggg tggcttcttc ctggaaccag caccgtttgt      780
ccacctgcaa atcctcatcc tcagtttgga ggtgccctct ccctcccctc cacgcacagc     840
tgtgacaggt acccaacccct gaggagccac cggtcctcac cctaccccag ccctatgct    900 catcggaaca attctccaac ctattctgac aactcacctg catgtttatc catgctgcaa     960
tcccatgaca attggtccag ccttggaatg cctgcccatc cagcatgct ccccgtgagc     1020 cacaatgcca gcccacctac cagctccagt cagtaccccca gcctgtggtc tgtgagcaac    1080
ggcgccgtca ccccgggctc ccaggcagca gccgtgtcca cgggctgggg gcccagttc     1140 ttccggggct ccccgcgca ctacacaccc ctcacccatc cggtctcggc gcctcttcc      1200 tcgggatccc cactgtacga aggggcggcc gcggccacag acatcgtgga cagccagtac    1260
gacgccgcag cccaaggccg cctcatagcc tcatggacac ctgtgtcgcc accttccatg    1320
tga                                                                  1323

<210> SEQ ID NO 54
<211> LENGTH: 441
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:52

<400> SEQUENCE: 54

Met Asn Met Ser Lys Lys Met Ser Ser Pro Gly Thr Glu Ser Ala Gly
1               5                   10                  15

Lys Ser Leu Gln Tyr Arg Val Asp His Leu Leu Ser Ala Val Glu Asn
```

```
                20              25              30
Glu Leu Gln Ala Gly Ser Glu Lys Gly Asp Pro Thr Glu Arg Glu Leu
            35              40              45
Arg Val Gly Leu Glu Glu Ser Glu Leu Trp Leu Arg Phe Lys Glu Leu
         50              55              60
Thr Asn Glu Met Ile Val Thr Lys Asn Gly Arg Arg Met Phe Pro Val
 65              70              75              80
Leu Lys Val Asn Val Ser Gly Leu Asp Pro Asn Ala Met Tyr Ser Phe
                85              90              95
Leu Leu Asp Phe Val Ala Ala Asp Asn His Arg Trp Lys Tyr Val Asn
            100             105             110
Gly Glu Trp Val Pro Gly Gly Lys Pro Glu Pro Gln Ala Pro Ser Cys
         115             120             125
Val Tyr Ile His Pro Asp Ser Pro Asn Phe Gly Ala His Trp Met Lys
    130             135             140
Ala Pro Val Ser Phe Ser Lys Val Lys Leu Thr Asn Lys Leu Asn Gly
145             150             155             160
Gly Gly Gln Ile Met Leu Asn Ser Leu His Lys Tyr Glu Pro Arg Ile
            165             170             175
His Ile Val Arg Val Gly Gly Pro Gln Arg Met Ile Thr Ser His Cys
         180             185             190
Phe Pro Glu Thr Gln Phe Ile Ala Val Thr Ala Tyr Gln Asn Glu Glu
    195             200             205
Ile Thr Ala Leu Lys Ile Lys Tyr Asn Pro Phe Ala Lys Ala Phe Leu
210             215             220
Asp Ala Lys Glu Arg Ser Asp His Lys Glu Met Met Glu Glu Pro Gly
225             230             235             240
Asp Ser Gln Gln Pro Gly Tyr Ser Gln Trp Gly Trp Leu Leu Pro Gly
            245             250             255
Thr Ser Thr Leu Cys Pro Pro Ala Asn Pro His Pro Gln Phe Gly Gly
         260             265             270
Ala Leu Ser Leu Pro Ser Thr His Ser Cys Asp Arg Tyr Pro Thr Leu
    275             280             285
Arg Ser His Arg Ser Ser Pro Tyr Pro Ser Pro Tyr Ala His Arg Asn
290             295             300
Asn Ser Pro Thr Tyr Ser Asp Asn Ser Pro Ala Cys Leu Ser Met Leu
305             310             315             320
Gln Ser His Asp Asn Trp Ser Ser Leu Gly Met Pro Ala His Pro Ser
            325             330             335
Met Leu Pro Val Ser His Asn Ala Ser Pro Pro Thr Ser Ser Ser Gln
         340             345             350
Tyr Pro Ser Leu Trp Ser Val Ser Asn Gly Ala Val Thr Pro Gly Ser
    355             360             365
Gln Ala Ala Ala Val Ser Asn Gly Leu Gly Ala Gln Phe Phe Arg Gly
370             375             380
Ser Pro Ala His Tyr Thr Pro Leu Thr His Pro Val Ser Ala Pro Ser
385             390             395             400
Ser Ser Gly Ser Pro Leu Tyr Glu Gly Ala Ala Ala Thr Asp Ile
            405             410             415
Val Asp Ser Gln Tyr Asp Ala Ala Ala Gln Gly Arg Leu Ile Ala Ser
         420             425             430
Trp Thr Pro Val Ser Pro Pro Ser Met
    435             440
```

<210> SEQ ID NO 55
<211> LENGTH: 440
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:53

<400> SEQUENCE: 55

```
Met Asn Met Ser Lys Lys Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
    130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Gly Pro Gln Arg Met Ile Thr Ser His Cys Phe
            180                 185                 190

Pro Glu Thr Gln Phe Ile Ala Val Thr Ala Tyr Gln Asn Glu Glu Ile
        195                 200                 205

Thr Ala Leu Lys Ile Lys Tyr Asn Pro Phe Ala Lys Ala Phe Leu Asp
    210                 215                 220

Ala Lys Glu Arg Ser Asp His Lys Glu Met Met Glu Glu Pro Gly Asp
225                 230                 235                 240

Ser Gln Gln Pro Gly Tyr Ser Gln Trp Gly Trp Leu Leu Pro Gly Thr
                245                 250                 255

Ser Thr Leu Cys Pro Pro Ala Asn Pro His Pro Gln Phe Gly Gly Ala
            260                 265                 270

Leu Ser Leu Pro Ser Thr His Ser Cys Asp Arg Tyr Pro Thr Leu Arg
        275                 280                 285

Ser His Arg Ser Ser Pro Tyr Pro Ser Pro Tyr Ala His Arg Asn Asn
    290                 295                 300

Ser Pro Thr Tyr Ser Asp Asn Ser Pro Ala Cys Leu Ser Met Leu Gln
305                 310                 315                 320

Ser His Asp Asn Trp Ser Ser Leu Gly Met Pro Ala His Pro Ser Met
                325                 330                 335

Leu Pro Val Ser His Asn Ala Ser Pro Pro Thr Ser Ser Ser Gln Tyr
            340                 345                 350

Pro Ser Leu Trp Ser Val Ser Asn Gly Ala Val Thr Pro Gly Ser Gln
```

```
                 355                 360                 365
Ala Ala Ala Val Ser Asn Gly Leu Gly Ala Gln Phe Phe Arg Gly Ser
    370                 375                 380

Pro Ala His Tyr Thr Pro Leu Thr His Pro Val Ser Ala Pro Ser Ser
385                 390                 395                 400

Ser Gly Ser Pro Leu Tyr Glu Gly Ala Ala Ala Thr Asp Ile Val
                405                 410                 415

Asp Ser Gln Tyr Asp Ala Ala Gln Gly Arg Leu Ile Ala Ser Trp
                420                 425                 430

Thr Pro Val Ser Pro Pro Ser Met
            435                 440
```

<210> SEQ ID NO 56
<211> LENGTH: 1320
<212> TYPE: DNA
<213> ORGANISM: Artificial Sequence
<220> FEATURE:
<223> OTHER INFORMATION: Coding sequence encoding Fusion protein comprising Brachyury protein Isoform 1 plus addition of 12 nucleotides from Gene FPV 088

<400> SEQUENCE: 56

```
atgagtaaga aaatgagctc ccctggcacc gagagcgcgg gaaagagcct gcagtaccga      60
gtggaccacc tgctgagcgc cgtggagaat gagctgcagg cgggcagcga aagggcgac     120
cccacagagc gcgaactgcg cgtgggcctg gaggagagcg agctgtggct gcgcttcaag     180
gagctcacca tgagatgat cgtgaccaag aacggcagga ggatgtttcc ggtgctgaag     240
gtgaacgtgt ctggcctgga ccccaacgcc atgtactcct tcctgctgga cttcgtggcg     300
gcggacaacc accgctggaa gtacgtgaac ggggaatggg tgccgggggg caagccggag     360
ccgcaggcgc ccagctgcgt ctacatccac cccgactcgc caacttcgg ggcccactgg     420
atgaaggctc ccgtctcctt cagcaaagtc aagctcacca acaagctcaa cggaggggc     480
cagatcatgc tgaactcctt gcataagtat gagcctcgaa tccacatagt gagagttggg     540
ggtccacagc gcatgatcac cagccactgc ttccctgaga cccagttcat agcggtgact     600
gcttatcaga cgaggagat cacagctctt aaaattaagt acaatccatt tgcaaaagct     660
ttccttgatg caaggaaag aagtgatcac aaagagatga tggaggaacc cggagacagc     720
cagcaacctg gtactccca tgggggtgg cttcttcctg aaccagcac cgtttgtcca     780
cctgcaaatc ctcatcctca gtttggaggt gccctctccc tcccctccac gcacagctgt     840
gacaggtacc caaccctgag gagccaccgg tcctcaccct accccagccc ctatgctcat     900
cggaacaatt ctccaaccta ttctgacaac tcacctgcat gtttatccat gctgcaatcc     960
catgacaatt ggtccagcct tggaatgcct gcccatccca gcatgctccc cgtgagccac    1020
aatgccagcc cacctaccag ctccagtcag taccccagcc tgtggtctgt gagcaacggc    1080
gccgtcaccc cgggctccca ggcagcagcc gtgtccaacg gctggggc ccagttcttc    1140
cggggctccc ccgcgcacta cacccctc acccatccgg tctcggcgcc ctcttcctcg    1200
ggatccccac tgtacgaagg ggcggccgcg gccacagaca tcgtggacag ccagtacgac    1260
gccgcagccc aaggccgcct catagcctca tggacacctg tgtcgccacc ttccatgtga    1320
```

<210> SEQ ID NO 57
<211> LENGTH: 1317
<212> TYPE: DNA
<213> ORGANISM: Artificial Sequence
<220> FEATURE:

<223> OTHER INFORMATION: Coding sequence encoding Fusion protein
      comprising Brachyury protein Isoform 1 plus addition of 12
      nucleotides from Gene FPV 088 without Brachyury atg start codon

<400> SEQUENCE: 57

```
atgagtaaga aaagctcccc tggcaccgag agcgcgggaa agagcctgca gtaccgagtg      60
gaccacctgc tgagcgccgt ggagaatgag ctgcaggcgg gcagcgagaa gggcgacccc     120
acagagcgcg aactgcgcgt gggcctggag gagagcgagc tgtggctgcg cttcaaggag     180
ctcaccaatg agatgatcgt gaccaagaac ggcaggagga tgtttccggt gctgaaggtg     240
aacgtgtctg gcctggaccc caacgccatg tactccttcc tgctggactt cgtggcggcg     300
gacaaccacc gctggaagta cgtgaacggg gaatgggtgc cggggggcaa gccggagccg     360
caggcgccca gctgcgtcta catccacccc gactcgccca acttcggggc ccactggatg     420
aaggctcccg tctccttcag caaagtcaag ctcaccaaca agctcaacgg aggggggccag     480
atcatgctga actccttgca taagtatgag cctcgaatcc acatagtgag agttgggggt     540
ccacagcgca tgatcaccag ccactgcttc cctgagaccc agttcatagc ggtgactgct     600
tatcagaacg aggagatcac agctcttaaa attaagtaca atccatttgc aaaagctttc     660
cttgatgcaa aggaaagaag tgatcacaaa gagatgatgg aggaacccgg agacagccag     720
caacctgggt actcccaatg ggggtggctt cttcctggaa ccagcaccgt ttgtccacct     780
gcaaatcctc atcctcagtt tggaggtgcc ctctccctcc cctccacgca cagctgtgac     840
aggtacccaa ccctgaggag ccaccggtcc tcaccctacc ccagcccta tgctcatcgg     900
aacaattctc aacctattc tgacaactca cctgcatgtt tatccatgct gcaatcccat     960
gacaattggt ccagccttgg aatgcctgcc catcccagca tgctccccgt gagccacaat    1020
gccagcccac ctaccagctc cagtcagtac cccagcctgt ggtctgtgag caacggcgcc    1080
gtcaccccgg ctcccaggc agcagccgtg tccaacgggc tgggggccca gttcttccgg    1140
ggctcccccg cgcactacac accccctcacc catccggtct cggcgccctc ttcctcggga    1200
tccccactgt acgaaggggc ggccgcggcc acagacatcg tggacagcca gtacgacgcc    1260
gcagcccaag ccgcctcat agcctcatgg acacctgtgt cgccaccttc catgtga       1317
```

<210> SEQ ID NO 58
<211> LENGTH: 439
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO: 56

<400> SEQUENCE: 58

```
Met Ser Lys Lys Met Ser Ser Pro Gly Thr Glu Ser Ala Gly Lys Ser
1               5                   10                  15

Leu Gln Tyr Arg Val Asp His Leu Leu Ser Ala Val Glu Asn Glu Leu
            20                  25                  30

Gln Ala Gly Ser Glu Lys Gly Asp Pro Thr Glu Arg Glu Leu Arg Val
        35                  40                  45

Gly Leu Glu Glu Ser Glu Leu Trp Leu Arg Phe Lys Glu Leu Thr Asn
    50                  55                  60

Glu Met Ile Val Thr Lys Asn Gly Arg Arg Met Phe Pro Val Leu Lys
65                  70                  75                  80

Val Asn Val Ser Gly Leu Asp Pro Asn Ala Met Tyr Ser Phe Leu Leu
                85                  90                  95
```

```
Asp Phe Val Ala Ala Asp Asn His Arg Trp Lys Tyr Val Asn Gly Glu
            100                 105                 110

Trp Val Pro Gly Gly Lys Pro Glu Pro Gln Ala Pro Ser Cys Val Tyr
        115                 120                 125

Ile His Pro Asp Ser Pro Asn Phe Gly Ala His Trp Met Lys Ala Pro
    130                 135                 140

Val Ser Phe Ser Lys Val Lys Leu Thr Asn Lys Leu Asn Gly Gly Gly
145                 150                 155                 160

Gln Ile Met Leu Asn Ser Leu His Lys Tyr Glu Pro Arg Ile His Ile
                165                 170                 175

Val Arg Val Gly Gly Pro Gln Arg Met Ile Thr Ser His Cys Phe Pro
            180                 185                 190

Glu Thr Gln Phe Ile Ala Val Thr Ala Tyr Gln Asn Glu Glu Ile Thr
        195                 200                 205

Ala Leu Lys Ile Lys Tyr Asn Pro Phe Ala Lys Ala Phe Leu Asp Ala
    210                 215                 220

Lys Glu Arg Ser Asp His Lys Glu Met Met Glu Pro Gly Asp Ser
225                 230                 235                 240

Gln Gln Pro Gly Tyr Ser Gln Trp Gly Trp Leu Leu Pro Gly Thr Ser
                245                 250                 255

Thr Leu Cys Pro Pro Ala Asn Pro His Pro Gln Phe Gly Gly Ala Leu
            260                 265                 270

Ser Leu Pro Ser Thr His Ser Cys Asp Arg Tyr Pro Thr Leu Arg Ser
        275                 280                 285

His Arg Ser Ser Pro Tyr Pro Ser Pro Tyr Ala His Arg Asn Asn Ser
    290                 295                 300

Pro Thr Tyr Ser Asp Asn Ser Pro Ala Cys Leu Ser Met Leu Gln Ser
305                 310                 315                 320

His Asp Asn Trp Ser Ser Leu Gly Met Pro Ala His Pro Ser Met Leu
                325                 330                 335

Pro Val Ser His Asn Ala Ser Pro Pro Thr Ser Ser Ser Gln Tyr Pro
            340                 345                 350

Ser Leu Trp Ser Val Ser Asn Gly Ala Val Thr Pro Gly Ser Gln Ala
        355                 360                 365

Ala Ala Val Ser Asn Gly Leu Gly Ala Gln Phe Phe Arg Gly Ser Pro
    370                 375                 380

Ala His Tyr Thr Pro Leu Thr His Pro Val Ser Ala Pro Ser Ser Ser
385                 390                 395                 400

Gly Ser Pro Leu Tyr Glu Gly Ala Ala Ala Thr Asp Ile Val Asp
                405                 410                 415

Ser Gln Tyr Asp Ala Ala Ala Gln Gly Arg Leu Ile Ala Ser Trp Thr
            420                 425                 430

Pro Val Ser Pro Pro Ser Met
        435

<210> SEQ ID NO 59
<211> LENGTH: 438
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:57

<400> SEQUENCE: 59

Met Ser Lys Lys Ser Ser Pro Gly Thr Glu Ser Ala Gly Lys Ser Leu
1               5                   10                  15
```

```
Gln Tyr Arg Val Asp His Leu Leu Ser Ala Val Glu Asn Glu Leu Gln
                 20                  25                  30

Ala Gly Ser Glu Lys Gly Asp Pro Thr Glu Arg Glu Leu Arg Val Gly
             35                  40                  45

Leu Glu Glu Ser Glu Leu Trp Leu Arg Phe Lys Glu Leu Thr Asn Glu
 50                  55                  60

Met Ile Val Thr Lys Asn Gly Arg Arg Met Phe Pro Val Leu Lys Val
 65                  70                  75                  80

Asn Val Ser Gly Leu Asp Pro Asn Ala Met Tyr Ser Phe Leu Leu Asp
                 85                  90                  95

Phe Val Ala Ala Asp Asn His Arg Trp Lys Tyr Val Asn Gly Glu Trp
                100                 105                 110

Val Pro Gly Gly Lys Pro Glu Pro Gln Ala Pro Ser Cys Val Tyr Ile
            115                 120                 125

His Pro Asp Ser Pro Asn Phe Gly Ala His Trp Met Lys Ala Pro Val
130                 135                 140

Ser Phe Ser Lys Val Lys Leu Thr Asn Lys Leu Asn Gly Gly Gly Gln
145                 150                 155                 160

Ile Met Leu Asn Ser Leu His Lys Tyr Glu Pro Arg Ile His Ile Val
                165                 170                 175

Arg Val Gly Gly Pro Gln Arg Met Ile Thr Ser His Cys Phe Pro Glu
            180                 185                 190

Thr Gln Phe Ile Ala Val Thr Ala Tyr Gln Asn Glu Glu Ile Thr Ala
        195                 200                 205

Leu Lys Ile Lys Tyr Asn Pro Phe Ala Lys Ala Phe Leu Asp Ala Lys
        210                 215                 220

Glu Arg Ser Asp His Lys Glu Met Met Glu Glu Pro Gly Asp Ser Gln
225                 230                 235                 240

Gln Pro Gly Tyr Ser Gln Trp Gly Trp Leu Leu Pro Gly Thr Ser Thr
                245                 250                 255

Leu Cys Pro Pro Ala Asn Pro His Pro Gln Phe Gly Gly Ala Leu Ser
            260                 265                 270

Leu Pro Ser Thr His Ser Cys Asp Arg Tyr Pro Thr Leu Arg Ser His
        275                 280                 285

Arg Ser Ser Pro Tyr Pro Ser Pro Tyr Ala His Arg Asn Asn Ser Pro
290                 295                 300

Thr Tyr Ser Asp Asn Ser Pro Ala Cys Leu Ser Met Leu Gln Ser His
305                 310                 315                 320

Asp Asn Trp Ser Ser Leu Gly Met Pro Ala His Pro Ser Met Leu Pro
                325                 330                 335

Val Ser His Asn Ala Ser Pro Pro Thr Ser Ser Ser Gln Tyr Pro Ser
            340                 345                 350

Leu Trp Ser Val Ser Asn Gly Ala Val Thr Pro Gly Ser Gln Ala Ala
        355                 360                 365

Ala Val Ser Asn Gly Leu Gly Ala Gln Phe Phe Arg Gly Ser Pro Ala
        370                 375                 380

His Tyr Thr Pro Leu Thr His Pro Val Ser Ala Pro Ser Ser Ser Gly
385                 390                 395                 400

Ser Pro Leu Tyr Glu Gly Ala Ala Ala Thr Asp Ile Val Asp Ser
                405                 410                 415

Gln Tyr Asp Ala Ala Ala Gln Gly Arg Leu Ile Ala Ser Trp Thr Pro
            420                 425                 430
```

Val Ser Pro Pro Ser Met
      435

<210> SEQ ID NO 60
<211> LENGTH: 1386
<212> TYPE: DNA
<213> ORGANISM: Artificial Sequence
<220> FEATURE:
<223> OTHER INFORMATION: Coding sequence encoding Fusion protein
      comprising Brachyury protein Isoform 1 plus addition of 75
      nucleotides from Gene FPV 088 and an atc

<400> SEQUENCE: 60

| | |
|---|---|
| atgaaaaata acttgtatga agaaaaaatg aacatgagta agaaacaagt aaaaactcaa | 60 |
| agtaaatgta ataatatcat gagctcccct ggcaccgaga gcgcgggaaa gagcctgcag | 120 |
| taccgagtgg accacctgct gagcgccgtg gagaatgagc tgcaggcggg cagcgagaag | 180 |
| ggcgacccca cagagcgcga actgcgcgtg ggcctggagg agagcgagct gtggctgcgc | 240 |
| ttcaaggagc tcaccaatga gatgatcgtg accaagaacg gcaggaggat gtttccggtg | 300 |
| ctgaaggtga acgtgtctgg cctggacccc aacgccatgt actccttcct gctggacttc | 360 |
| gtggcggcgg acaaccaccg ctggaagtac gtgaacgggg aatgggtgcc ggggggcaag | 420 |
| ccggagccgc aggcgcccag ctgcgtctac atccaccccg actcgcccaa cttcggggcc | 480 |
| cactggatga aggctcccgt ctccttcagc aaagtcaagc tcaccaacaa gctcaacgga | 540 |
| gggggccaga tcatgctgaa ctccttgcat aagtatgagc ctcgaatcca catagtgaga | 600 |
| gttgggggtc cacagcgcat gatcaccagc cactgcttcc ctgagaccca gttcatagcg | 660 |
| gtgactgctt atcagaacga ggagatcaca gctcttaaaa ttaagtacaa tccatttgca | 720 |
| aaagcttttc ttgatgcaaa ggaaagaagt gatcacaaag atgatggag gaacccggga | 780 |
| gacagccagc aacctgggta ctcccaatgg gggtggcttc ttcctggaac cagcaccgtt | 840 |
| tgtccacctg caaatcctca tcctcagttt ggaggtgccc tctccctccc ctccacgcac | 900 |
| agctgtgaca ggtacccaac cctgaggagc caccggtcct caccctaccc cagcccctat | 960 |
| gctcatcgga caattctcc aacctattct gacaactcac ctgcatgttt atccatgctg | 1020 |
| caatcccatg acaattggtc cagccttgga atgcctgccc atcccagcat gctccccgtg | 1080 |
| agccacaatg ccagcccacc taccagctcc agtcagtacc ccagcctgtg gtctgtgagc | 1140 |
| aacggcgccg tcaccccggg ctcccaggca gcagccgtgt ccaacgggct gggggcccag | 1200 |
| ttcttccggg gctcccccgc gcactacaca cccctcaccc atccggtctc ggcgccctct | 1260 |
| tcctcgggat ccccactgta cgaaggggcg gccgcggcca cagacatcgt ggacagccag | 1320 |
| tacgacgccg cagcccaagg ccgcctcata gcctcatgga cacctgtgtc gccaccttcc | 1380 |
| atgtga | 1386 |

<210> SEQ ID NO 61
<211> LENGTH: 1383
<212> TYPE: DNA
<213> ORGANISM: Artificial Sequence
<220> FEATURE:
<223> OTHER INFORMATION: Coding sequence encoding Fusion protein
      comprising Brachyury protein Isoform 1 plus addition of 75
      nucleotides from Gene FPV 088 and an atc, without Brachyury atg
      start codon

<400> SEQUENCE: 61

| | |
|---|---|
| atgaaaaata acttgtatga agaaaaaatg aacatgagta agaaacaagt aaaaactcaa | 60 |
| agtaaatgta ataatatcag ctcccctggc accgagagcg cgggaaagag cctgcagtac | 120 |

-continued

```
cgagtggacc acctgctgag cgccgtggag aatgagctgc aggcgggcag cgagaagggc    180
gaccccacag agcgcgaact gcgcgtgggc ctggaggaga cgagctgtg gctgcgcttc     240 aaggagctca ccaatgagat gatcgtgacc aagaacggca ggaggatgtt tccggtgctg    300
aaggtgaacg tgtctggcct ggaccccaac gccatgtact ccttcctgct ggacttcgtg    360
gcggcggaca accaccgctg gaagtacgtg aacggggaat gggtgccggg gggcaagccg    420
gagccgcagg cgcccagctg cgtctacatc caccccgact cgcccaactt cggggcccac    480
tggatgaagg ctcccgtctc cttcagcaaa gtcaagctca ccaacaagct caacggaggg    540
ggccagatca tgctgaactc cttgcataag tatgagcctc gaatccacat agtgagagtt    600
gggggtccac agcgcatgat caccagccac tgcttccctg agacccagtt catagcggtg    660
actgcttatc agaacgagga gatcacagct cttaaaatta agtacaatcc atttgcaaaa    720
gctttccttg atgcaaagga agaagtgat cacaaagaga tgatggagga acccggagac    780
agccagcaac ctgggtactc ccaatggggg tggcttcttc ctggaaccag caccgtttgt    840
ccacctgcaa atcctcatcc tcagtttgga ggtgccctct ccctcccctc cacgcacagc    900
tgtgacaggt acccaacccct gaggagccac cggtcctcac cctaccccag ccctatgct    960 catcggaaca attctccaac ctattctgac aactcacctg catgtttatc catgctgcaa   1020
tcccatgaca attggtccag ccttggaatg cctgcccatc ccagcatgct ccccgtgagc   1080
cacaatgcca gcccacctac cagctccagt cagtacccca gcctgtggtc tgtgagcaac   1140
ggcgccgtca ccccgggctc ccaggcagca gccgtgtcca acgggctggg ggcccagttc   1200
ttccggggct ccccgcgca ctacacaccc ctcacccatc cggtctcggc gccctcttcc    1260
tcgggatccc cactgtacga aggggcggcc gcggccacag acatcgtgga cagccagtac   1320
gacgccgcag cccaaggccg cctcatagcc tcatggacac ctgtgtcgcc accttccatg   1380
tga                                                                  1383
```

```
<210> SEQ ID NO 62
<211> LENGTH: 461
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:60

<400> SEQUENCE: 62

Met Lys Asn Asn Leu Tyr Glu Glu Lys Met Asn Met Ser Lys Lys Gln
1               5                   10                  15

Val Lys Thr Gln Ser Lys Cys Asn Asn Ile Met Ser Ser Pro Gly Thr
            20                  25                  30

Glu Ser Ala Gly Lys Ser Leu Gln Tyr Arg Val Asp His Leu Leu Ser
        35                  40                  45

Ala Val Glu Asn Glu Leu Gln Ala Gly Ser Glu Lys Gly Asp Pro Thr
    50                  55                  60

Glu Arg Glu Leu Arg Val Gly Leu Glu Glu Ser Glu Leu Trp Leu Arg
65                  70                  75                  80

Phe Lys Glu Leu Thr Asn Glu Met Ile Val Thr Lys Asn Gly Arg Arg
                85                  90                  95

Met Phe Pro Val Leu Lys Val Asn Val Ser Gly Leu Asp Pro Asn Ala
            100                 105                 110

Met Tyr Ser Phe Leu Leu Asp Phe Val Ala Ala Asp Asn His Arg Trp
        115                 120                 125
```

```
Lys Tyr Val Asn Gly Glu Trp Val Pro Gly Lys Pro Glu Pro Gln
            130                 135                 140

Ala Pro Ser Cys Val Tyr Ile His Pro Asp Ser Pro Asn Phe Gly Ala
145                 150                 155                 160

His Trp Met Lys Ala Pro Val Ser Phe Ser Lys Val Lys Leu Thr Asn
                165                 170                 175

Lys Leu Asn Gly Gly Gly Gln Ile Met Leu Asn Ser Leu His Lys Tyr
            180                 185                 190

Glu Pro Arg Ile His Ile Val Arg Val Gly Gly Pro Gln Arg Met Ile
            195                 200                 205

Thr Ser His Cys Phe Pro Glu Thr Gln Phe Ile Ala Val Thr Ala Tyr
            210                 215                 220

Gln Asn Glu Glu Ile Thr Ala Leu Lys Ile Lys Tyr Asn Pro Phe Ala
225                 230                 235                 240

Lys Ala Phe Leu Asp Ala Lys Glu Arg Ser Asp His Lys Glu Met Met
                245                 250                 255

Glu Glu Pro Gly Asp Ser Gln Gln Pro Gly Tyr Ser Gln Trp Gly Trp
            260                 265                 270

Leu Leu Pro Gly Thr Ser Thr Leu Cys Pro Pro Ala Asn Pro His Pro
            275                 280                 285

Gln Phe Gly Gly Ala Leu Ser Leu Pro Ser Thr His Ser Cys Asp Arg
            290                 295                 300

Tyr Pro Thr Leu Arg Ser His Arg Ser Ser Pro Tyr Pro Ser Pro Tyr
305                 310                 315                 320

Ala His Arg Asn Asn Ser Pro Thr Tyr Ser Asp Asn Ser Pro Ala Cys
                325                 330                 335

Leu Ser Met Leu Gln Ser His Asp Asn Trp Ser Ser Leu Gly Met Pro
            340                 345                 350

Ala His Pro Ser Met Leu Pro Val Ser His Asn Ala Ser Pro Pro Thr
            355                 360                 365

Ser Ser Ser Gln Tyr Pro Ser Leu Trp Ser Val Ser Asn Gly Ala Val
370                 375                 380

Thr Pro Gly Ser Gln Ala Ala Ala Val Ser Asn Gly Leu Gly Ala Gln
385                 390                 395                 400

Phe Phe Arg Gly Ser Pro Ala His Tyr Thr Pro Leu Thr His Pro Val
                405                 410                 415

Ser Ala Pro Ser Ser Ser Gly Ser Pro Leu Tyr Glu Gly Ala Ala Ala
            420                 425                 430

Ala Thr Asp Ile Val Asp Ser Gln Tyr Asp Ala Ala Ala Gln Gly Arg
            435                 440                 445

Leu Ile Ala Ser Trp Thr Pro Val Ser Pro Pro Ser Met
450                 455                 460

<210> SEQ ID NO 63
<211> LENGTH: 460
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:61

<400> SEQUENCE: 63

Met Lys Asn Asn Leu Tyr Glu Glu Lys Met Asn Met Ser Lys Lys Gln
1               5                   10                  15

Val Lys Thr Gln Ser Lys Cys Asn Asn Ile Ser Ser Pro Gly Thr Glu
```

```
            20                  25                  30
Ser Ala Gly Lys Ser Leu Gln Tyr Arg Val Asp His Leu Leu Ser Ala
            35                  40                  45

Val Glu Asn Glu Leu Gln Ala Gly Ser Glu Lys Gly Asp Pro Thr Glu
            50                  55                  60

Arg Glu Leu Arg Val Gly Leu Glu Glu Ser Glu Leu Trp Leu Arg Phe
65                  70                  75                  80

Lys Glu Leu Thr Asn Glu Met Ile Val Thr Lys Asn Gly Arg Arg Met
                85                  90                  95

Phe Pro Val Leu Lys Val Asn Val Ser Gly Leu Asp Pro Asn Ala Met
            100                 105                 110

Tyr Ser Phe Leu Leu Asp Phe Val Ala Ala Asp Asn His Arg Trp Lys
            115                 120                 125

Tyr Val Asn Gly Glu Trp Val Pro Gly Gly Lys Pro Glu Pro Gln Ala
            130                 135                 140

Pro Ser Cys Val Tyr Ile His Pro Asp Ser Pro Asn Phe Gly Ala His
145                 150                 155                 160

Trp Met Lys Ala Pro Val Ser Phe Ser Lys Val Lys Leu Thr Asn Lys
                165                 170                 175

Leu Asn Gly Gly Gly Gln Ile Met Leu Asn Ser Leu His Lys Tyr Glu
            180                 185                 190

Pro Arg Ile His Ile Val Arg Val Gly Gly Pro Gln Arg Met Ile Thr
            195                 200                 205

Ser His Cys Phe Pro Glu Thr Gln Phe Ile Ala Val Thr Ala Tyr Gln
            210                 215                 220

Asn Glu Glu Ile Thr Ala Leu Lys Ile Lys Tyr Asn Pro Phe Ala Lys
225                 230                 235                 240

Ala Phe Leu Asp Ala Lys Glu Arg Ser Asp His Lys Glu Met Met Glu
                245                 250                 255

Glu Pro Gly Asp Ser Gln Gln Pro Gly Tyr Ser Gln Trp Gly Trp Leu
            260                 265                 270

Leu Pro Gly Thr Ser Thr Leu Cys Pro Pro Ala Asn Pro His Pro Gln
            275                 280                 285

Phe Gly Gly Ala Leu Ser Leu Pro Ser Thr His Ser Cys Asp Arg Tyr
            290                 295                 300

Pro Thr Leu Arg Ser His Arg Ser Ser Pro Tyr Pro Ser Pro Tyr Ala
305                 310                 315                 320

His Arg Asn Asn Ser Pro Thr Tyr Ser Asp Asn Ser Pro Ala Cys Leu
                325                 330                 335

Ser Met Leu Gln Ser His Asp Asn Trp Ser Ser Leu Gly Met Pro Ala
            340                 345                 350

His Pro Ser Met Leu Pro Val Ser His Asn Ala Ser Pro Pro Thr Ser
            355                 360                 365

Ser Ser Gln Tyr Pro Ser Leu Trp Ser Val Ser Asn Gly Ala Val Thr
            370                 375                 380

Pro Gly Ser Gln Ala Ala Val Ser Asn Gly Leu Gly Ala Gln Phe
385                 390                 395                 400

Phe Arg Gly Ser Pro Ala His Tyr Thr Pro Leu Thr His Pro Val Ser
                405                 410                 415

Ala Pro Ser Ser Ser Gly Ser Pro Leu Tyr Glu Gly Ala Ala Ala Ala
            420                 425                 430

Thr Asp Ile Val Asp Ser Gln Tyr Asp Ala Ala Ala Gln Gly Arg Leu
            435                 440                 445
```

```
Ile Ala Ser Trp Thr Pro Val Ser Pro Pro Ser Met
    450                 455                 460
```

<210> SEQ ID NO 64
<211> LENGTH: 1359
<212> TYPE: DNA
<213> ORGANISM: Artificial Sequence
<220> FEATURE:
<223> OTHER INFORMATION: Coding sequence encoding Fusion protein
      comprising Brachyury protein Isoform 1 plus addition of 48
      nucleotides from Gene FPV 088 and an atc

<400> SEQUENCE: 64

```
atgaacatga gtaagaaaca agtaaaaact caaagtaaat gtaataatat catgagctcc      60
cctggcaccg agagcgcggg aaagagcctg cagtaccgag tggaccacct gctgagcgcc     120
gtggagaatg agctgcaggc gggcagcgag aagggcgacc ccacagagcg cgaactgcgc     180
gtgggcctgg aggagagcga gctgtggctg cgcttcaagg agctcaccaa tgagatgatc     240
gtgaccaaga cggcaggag gatgtttccg gtgctgaagg tgaacgtgtc tggcctggac     300
cccaacgcca tgtactcctt cctgctggac ttcgtggcgg cggacaacca ccgctggaag     360
tacgtgaacg gggaatgggt gccgggggggc aagccggagc gcaggcgcc cagctgcgtc     420
tacatccacc ccgactcgcc caacttcggg gcccactgga tgaaggctcc cgtctccttc     480
agcaaagtca agctcaccaa caagctcaac ggagggggcc agatcatgct gaactccttg     540
cataagtatg agcctcgaat ccacatagtg agagttgggg gtccacagcg catgatcacc     600
agccactgct ccctgagac ccagttcata gcggtgactg cttatcagaa cgaggagatc     660
acagctctta aaattaagta caatccattt gcaaaagctt ccttgatgc aaaggaaaga     720
agtgatcaca agagatgat ggaggaaccc ggagacagcc agcaacctgg gtactcccaa     780
tgggggtggc ttcttcctgg aaccagcacc gtttgtccac ctgcaaatcc tcatcctcag     840
tttggaggtg ccctctccct cccctccacg cacagctgtg acaggtaccc aaccctgagg     900
agccaccggt cctcacccta ccccagcccc tatgctcatc ggaacaattc tccaacctat     960
tctgacaact cacctgcatg tttatccatg ctgcaatccc atgacaattg gtccagcctt    1020
ggaatgcctg cccatcccag catgctcccc gtgagccaca atgccagccc acctaccagc    1080
tccagtcagt accccagcct gtggtctgtg agcaacggcg ccgtcacccc gggctcccag    1140
gcagcagccg tgtccaacgg gctgggggcc cagttcttcc ggggctcccc cgcgcactac    1200
acacccctca cccatccggt ctcggcgccc tcttcctcgg gatccccact gtacgaaggg    1260
gcggccgcgg ccacagacat cgtggacagc cagtacgacg ccgcagccca aggccgcctc    1320
atagcctcat ggacacctgt gtcgccacct tccatgtga                          1359
```

<210> SEQ ID NO 65
<211> LENGTH: 1356
<212> TYPE: DNA
<213> ORGANISM: Artificial Sequence
<220> FEATURE:
<223> OTHER INFORMATION: Coding sequence encoding Fusion protein
      comprising Brachyury protein Isoform 1 plus addition of 48
      nucleotides from Gene FPV 088 and an atc, without Brachyury atg
      start codon

<400> SEQUENCE: 65

```
atgaacatga gtaagaaaca agtaaaaact caaagtaaat gtaataatat cagctcccct      60
ggcaccgaga gcgcgggaaa gagcctgcag taccgagtgg accacctgct gagcgccgtg     120
```

```
gagaatgagc tgcaggcggg cagcgagaag ggcgacccca cagagcgcga actgcgcgtg    180
ggcctggagg agagcgagct gtggctgcgc ttcaaggagc tcaccaatga gatgatcgtg    240
accaagaacg gcaggaggat gtttccggtg ctgaaggtga acgtgtctgg cctggacccc    300
aacgccatgt actccttcct gctggacttc gtggcggcgg acaaccaccg ctggaagtac    360
gtgaacgggg aatgggtgcc ggggggcaag ccggagccgc aggcgcccag ctgcgtctac    420
atccaccccg actcgcccaa cttcgggggcc actggatgaa ggctcccgt ctccttcagc    480 aaagtcaagc tcaccaacaa gctcaacgga ggggggccaga tcatgctgaa ctccttgcat    540
aagtatgagc tcgaatcca catagtgaga gttgggggtc cacagcgcat gatcaccagc    600
cactgcttcc ctgagaccca gttcatagcg gtgactgctt atcagaacga ggagatcaca    660
gctcttaaaa ttaagtacaa tccatttgca aaagctttcc ttgatgcaaa ggaaagaagt    720
gatcacaaag agatgatgga ggaacccgga gacagccagc aacctgggta ctcccaatgg    780
gggtggcttc ttcctggaac cagcaccgtt tgtccacctg caaatcctca tcctcagttt    840
ggaggtgccc tctccctccc ctccacgcac agctgtgaca ggtacccaac cctgaggagc    900
caccggtcct caccctaccc cagcccctat gctcatcgga caattctccc aacctattct    960
gacaactcac ctgcatgttt atccatgctg caatcccatg acaattggtc cagccttgga   1020
atgcctgccc atcccagcat gctccccgtg agccacaatg ccagcccacc taccagctcc   1080
agtcagtacc cagcctgtg gtctgtgagc aacggcgccg tcaccccggg ctcccaggca   1140
gcagccgtgt ccaacgggct ggggggccag ttcttccggg gctcccccgc gcactacaca   1200
cccctcaccc atccggtctc ggcgccctct tcctcgggat cccactgta cgaaggggcg   1260 gccgcggcca cagacatcgt ggacagccag tacgacgccg cagcccaagg ccgcctcata   1320
gcctcatgga cacctgtgtc gccaccttcc atgtga                             1356
```

<210> SEQ ID NO 66
<211> LENGTH: 452
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:64

<400> SEQUENCE: 66

Met Asn Met Ser Lys Lys Gln Val Lys Thr Gln Ser Lys Cys Asn Asn
1               5                   10                  15

Ile Met Ser Ser Pro Gly Thr Glu Ser Ala Gly Lys Ser Leu Gln Tyr
            20                  25                  30

Arg Val Asp His Leu Leu Ser Ala Val Glu Asn Glu Leu Gln Ala Gly
        35                  40                  45

Ser Glu Lys Gly Asp Pro Thr Glu Arg Glu Leu Arg Val Gly Leu Glu
    50                  55                  60

Glu Ser Glu Leu Trp Leu Arg Phe Lys Glu Leu Thr Asn Glu Met Ile
65                  70                  75                  80

Val Thr Lys Asn Gly Arg Arg Met Phe Pro Val Leu Lys Val Asn Val
                85                  90                  95

Ser Gly Leu Asp Pro Asn Ala Met Tyr Ser Phe Leu Leu Asp Phe Val
            100                 105                 110

Ala Ala Asp Asn His Arg Trp Lys Tyr Val Asn Gly Glu Trp Val Pro
        115                 120                 125

Gly Gly Lys Pro Glu Pro Gln Ala Pro Ser Cys Val Tyr Ile His Pro
    130                 135                 140

```
Asp Ser Pro Asn Phe Gly Ala His Trp Met Lys Ala Pro Val Ser Phe
145                 150                 155                 160

Ser Lys Val Lys Leu Thr Asn Lys Leu Asn Gly Gly Gly Gln Ile Met
            165                 170                 175

Leu Asn Ser Leu His Lys Tyr Glu Pro Arg Ile His Ile Val Arg Val
        180                 185                 190

Gly Gly Pro Gln Arg Met Ile Thr Ser His Cys Phe Pro Glu Thr Gln
    195                 200                 205

Phe Ile Ala Val Thr Ala Tyr Gln Asn Glu Glu Ile Thr Ala Leu Lys
210                 215                 220

Ile Lys Tyr Asn Pro Phe Ala Lys Ala Phe Leu Asp Ala Lys Glu Arg
225                 230                 235                 240

Ser Asp His Lys Glu Met Met Glu Pro Gly Asp Ser Gln Gln Pro
                245                 250                 255

Gly Tyr Ser Gln Trp Gly Trp Leu Leu Pro Gly Thr Ser Thr Leu Cys
        260                 265                 270

Pro Pro Ala Asn Pro His Pro Gln Phe Gly Gly Ala Leu Ser Leu Pro
        275                 280                 285

Ser Thr His Ser Cys Asp Arg Tyr Pro Thr Leu Arg Ser His Arg Ser
        290                 295                 300

Ser Pro Tyr Pro Ser Pro Tyr Ala His Arg Asn Asn Ser Pro Thr Tyr
305                 310                 315                 320

Ser Asp Asn Ser Pro Ala Cys Leu Ser Met Leu Gln Ser His Asp Asn
                325                 330                 335

Trp Ser Ser Leu Gly Met Pro Ala His Pro Ser Met Leu Pro Val Ser
            340                 345                 350

His Asn Ala Ser Pro Pro Thr Ser Ser Ser Gln Tyr Pro Ser Leu Trp
            355                 360                 365

Ser Val Ser Asn Gly Ala Val Thr Pro Gly Ser Gln Ala Ala Ala Val
    370                 375                 380

Ser Asn Gly Leu Gly Ala Gln Phe Phe Arg Gly Ser Pro Ala His Tyr
385                 390                 395                 400

Thr Pro Leu Thr His Pro Val Ser Ala Pro Ser Ser Ser Gly Ser Pro
                405                 410                 415

Leu Tyr Glu Gly Ala Ala Ala Thr Asp Ile Val Asp Ser Gln Tyr
            420                 425                 430

Asp Ala Ala Gln Gly Arg Leu Ile Ala Ser Trp Thr Pro Val Ser
        435                 440                 445

Pro Pro Ser Met
    450

<210> SEQ ID NO 67
<211> LENGTH: 451
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:65

<400> SEQUENCE: 67

Met Asn Met Ser Lys Lys Gln Val Lys Thr Gln Ser Lys Cys Asn Asn
1               5                   10                  15

Ile Ser Ser Pro Gly Thr Glu Ser Ala Gly Lys Ser Leu Gln Tyr Arg
            20                  25                  30

Val Asp His Leu Leu Ser Ala Val Glu Asn Glu Leu Gln Ala Gly Ser
```

```
            35                  40                  45
Glu Lys Gly Asp Pro Thr Glu Arg Glu Leu Arg Val Gly Leu Glu Glu
 50                  55                  60

Ser Glu Leu Trp Leu Arg Phe Lys Glu Leu Thr Asn Glu Met Ile Val
 65                  70                  75                  80

Thr Lys Asn Gly Arg Arg Met Phe Pro Val Leu Lys Val Asn Val Ser
                 85                  90                  95

Gly Leu Asp Pro Asn Ala Met Tyr Ser Phe Leu Leu Asp Phe Val Ala
                100                 105                 110

Ala Asp Asn His Arg Trp Lys Tyr Val Asn Gly Glu Trp Val Pro Gly
                115                 120                 125

Gly Lys Pro Glu Pro Gln Ala Pro Ser Cys Val Tyr Ile His Pro Asp
            130                 135                 140

Ser Pro Asn Phe Gly Ala His Trp Met Lys Ala Pro Val Ser Phe Ser
145                 150                 155                 160

Lys Val Lys Leu Thr Asn Lys Leu Asn Gly Gly Gln Ile Met Leu
                165                 170                 175

Asn Ser Leu His Lys Tyr Glu Pro Arg Ile His Ile Val Arg Val Gly
                180                 185                 190

Gly Pro Gln Arg Met Ile Thr Ser His Cys Phe Pro Glu Thr Gln Phe
            195                 200                 205

Ile Ala Val Thr Ala Tyr Gln Asn Glu Glu Ile Thr Ala Leu Lys Ile
210                 215                 220

Lys Tyr Asn Pro Phe Ala Lys Ala Phe Leu Asp Ala Lys Glu Arg Ser
225                 230                 235                 240

Asp His Lys Glu Met Met Glu Glu Pro Gly Asp Ser Gln Gln Pro Gly
                245                 250                 255

Tyr Ser Gln Trp Gly Trp Leu Leu Pro Gly Thr Ser Thr Leu Cys Pro
                260                 265                 270

Pro Ala Asn Pro His Pro Gln Phe Gly Gly Ala Leu Ser Leu Pro Ser
            275                 280                 285

Thr His Ser Cys Asp Arg Tyr Pro Thr Leu Arg Ser His Arg Ser Ser
        290                 295                 300

Pro Tyr Pro Ser Pro Tyr Ala His Arg Asn Asn Ser Pro Thr Tyr Ser
305                 310                 315                 320

Asp Asn Ser Pro Ala Cys Leu Ser Met Leu Gln Ser His Asp Asn Trp
                325                 330                 335

Ser Ser Leu Gly Met Pro Ala His Pro Ser Met Leu Pro Val Ser His
                340                 345                 350

Asn Ala Ser Pro Pro Thr Ser Ser Gln Tyr Pro Ser Leu Trp Ser
            355                 360                 365

Val Ser Asn Gly Ala Val Thr Pro Gly Ser Gln Ala Ala Val Ser
370                 375                 380

Asn Gly Leu Gly Ala Gln Phe Phe Arg Gly Ser Pro Ala His Tyr Thr
385                 390                 395                 400

Pro Leu Thr His Pro Val Ser Ala Pro Ser Ser Ser Gly Ser Pro Leu
                405                 410                 415

Tyr Glu Gly Ala Ala Ala Ala Thr Asp Ile Val Asp Ser Gln Tyr Asp
                420                 425                 430

Ala Ala Ala Gln Gly Arg Leu Ile Ala Ser Trp Thr Pro Val Ser Pro
            435                 440                 445

Pro Ser Met
        450
```

<210> SEQ ID NO 68
<211> LENGTH: 1353
<212> TYPE: DNA
<213> ORGANISM: Artificial Sequence
<220> FEATURE:
<223> OTHER INFORMATION: Coding sequence encoding Fusion protein
      comprising Brachyury protein Isoform 1  plus addition of 42
      nucleotides from Gene FPV 088 and an atc

<400> SEQUENCE: 68

```
atgagtaaga aacaagtaaa aactcaaagt aaatgtaata atatcatgag ctcccctggc     60
accgagagcg cgggaaagag cctgcagtac cgagtggacc acctgctgag cgccgtggag    120
aatgagctgc aggcgggcag cgagaagggc gaccccacag agcgcgaact gcgcgtgggc    180
ctggaggaga cgagctgtg gctgcgcttc aaggagctca ccaatgagat gatcgtgacc    240
aagaacggca ggaggatgtt tccggtgctg aaggtgaacg tgtctggcct ggaccccaac    300
gccatgtact ccttcctgct ggacttcgtg gcggcggaca ccaccgctg gaagtacgtg     360
aacggggaat gggtgccggg gggcaagccg agccgcagg cgcccagctg cgtctacatc     420
cacccccgact cgcccaactt cggggcccac tggatgaagg ctcccgtctc cttcagcaaa    480
gtcaagctca ccaacaagct caacggaggg ggccagatca tgctgaactc cttgcataag    540
tatgagcctc gaatccacat agtgagagtt gggggtccac agcgcatgat caccagccac    600
tgcttccctg agacccagtt catagcggtg actgcttatc agaacgagga gatcacagct    660
cttaaaatta agtacaatcc atttgcaaaa gctttccttg atgcaaagga agaagtgat    720
cacaaagaga tgatggagga acccggagac agccagcaac tgggtactc ccaatggggg    780
tggcttcttc ctggaaccag caccgtttgt ccacctgcaa atcctcatcc tcagtttgga    840
ggtgccctct ccctcccctc cacgcacagc tgtgacaggt acccaaccct gaggagccac    900
cggtcctcac cctaccccag cccctatgct catcggaaca attctccaac ctattctgac    960
aactcacctg catgtttatc catgctgcaa tcccatgaca attggtccag ccttggaatg   1020
cctgcccatc ccagcatgct ccccgtgagc acaatgcca gcccacctac cagctccagt    1080
cagtacccca gcctgtggtc tgtgagcaac ggcgccgtca ccccgggctc ccaggcagca   1140
gccgtgtcca acgggctggg ggcccagttc ttcggggct ccccgcgca ctacacaccc     1200
ctcacccatc cggtctcggc gccctcttcc tcgggatccc cactgtacga aggggcggcc   1260
gcggccacag acatcgtgga cagccagtac gacgccgcag cccaaggccg cctcatagcc   1320
tcatggacac ctgtgtcgcc accttccatg tga                                1353
```

<210> SEQ ID NO 69
<211> LENGTH: 1350
<212> TYPE: DNA
<213> ORGANISM: Artificial Sequence
<220> FEATURE:
<223> OTHER INFORMATION: Coding sequence encoding Fusion protein
      comprising Brachyury protein Isoform 1  plus addition of 42
      nucleotides from Gene FPV 088 and an atc, without Brachyury atg
      start codon

<400> SEQUENCE: 69

```
atgagtaaga aacaagtaaa aactcaaagt aaatgtaata atatcagctc ccctggcacc     60
gagagcgcgg gaaagagcct gcagtaccga gtggaccacc tgctgagcgc cgtggagaat    120
gagctgcagg cggcagcga aagggcgac cccacagagc gcgaactgcg cgtgggcctg     180
gaggagacgc agctgtggct gcgcttcaag gagctcacca tgagatgat cgtgaccaag    240
```

```
aacggcagga ggatgtttcc ggtgctgaag gtgaacgtgt ctggcctgga ccccaacgcc    300
atgtactcct tcctgctgga cttcgtggcg gcggacaacc accgctggaa gtacgtgaac    360
ggggaatggg tgccggggggg caagccggag ccgcaggcgc ccagctgcgt ctacatccac    420
cccgactcgc ccaacttcgg ggcccactgg atgaaggctc ccgtctcctt cagcaaagtc    480
aagctcacca acaagctcaa cggagggggc cagatcatgc tgaactcctt gcataagtat    540
gagcctcgaa tccacatagt gagagttggg ggtccacagc gcatgatcac cagccactgc    600
ttccctgaga cccagttcat agcggtgact gcttatcaga acgaggagat cacagctctt    660
aaaattaagt acaatccatt tgcaaaagct ttccttgatg caaaggaaag aagtgatcac    720
aaagagatga tggaggaacc cggagacagc cagcaacctg ggtactccca atggggtgg     780 cttcttcctg gaaccagcac cgtttgtcca cctgcaaatc ctcatcctca gtttggaggt    840
gccctctccc tcccctccac gcacagctgt gacaggtacc caaccctgag gagccaccgg    900
tcctcaccct accccagccc ctatgctcat cggaacaatt ctccaaccta ttctgacaac    960
tcacctgcat gtttatccat gctgcaatcc catgacaatt ggtccagcct ggaatgcct    1020 gcccatccca gcatgctccc cgtgagccac aatgccagcc acctaccag ctccagtcag    1080 taccccagcc tgtggtctgt gagcaacggc gccgtcaccc cgggctccca ggcagcagcc    1140
gtgtccaacg gctgggggc ccagttcttc cggggctccc ccgcgcacta cacccctc     1200 acccatccgg tctcggcgcc ctcttcctcg ggatccccac tgtacgaagg ggcggccgcg    1260
gccacagaca tcgtggacag ccagtacgac gccgcagccc aaggccgcct catagcctca    1320
tggacacctg tgtcgccacc ttccatgtga                                    1350

<210> SEQ ID NO 70
<211> LENGTH: 450
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:68

<400> SEQUENCE: 70

Met Ser Lys Lys Gln Val Lys Thr Gln Ser Lys Cys Asn Asn Ile Met
1               5                   10                  15

Ser Ser Pro Gly Thr Glu Ser Ala Gly Lys Ser Leu Gln Tyr Arg Val
            20                  25                  30

Asp His Leu Leu Ser Ala Val Glu Asn Glu Leu Gln Ala Gly Ser Glu
        35                  40                  45

Lys Gly Asp Pro Thr Glu Arg Glu Leu Arg Val Gly Leu Glu Glu Ser
    50                  55                  60

Glu Leu Trp Leu Arg Phe Lys Glu Leu Thr Asn Glu Met Ile Val Thr
65                  70                  75                  80

Lys Asn Gly Arg Arg Met Phe Pro Val Leu Lys Val Asn Val Ser Gly
                85                  90                  95

Leu Asp Pro Asn Ala Met Tyr Ser Phe Leu Leu Asp Phe Val Ala Ala
            100                 105                 110

Asp Asn His Arg Trp Lys Tyr Val Asn Gly Glu Trp Val Pro Gly Gly
        115                 120                 125

Lys Pro Glu Pro Gln Ala Pro Ser Cys Val Tyr Ile His Pro Asp Ser
    130                 135                 140

Pro Asn Phe Gly Ala His Trp Met Lys Ala Pro Val Ser Phe Ser Lys
145                 150                 155                 160
```

```
Val Lys Leu Thr Asn Lys Leu Asn Gly Gly Gln Ile Met Leu Asn
                165                 170                 175

Ser Leu His Lys Tyr Glu Pro Arg Ile His Ile Val Arg Val Gly Gly
                180                 185                 190

Pro Gln Arg Met Ile Thr Ser His Cys Phe Pro Glu Thr Gln Phe Ile
                195                 200                 205

Ala Val Thr Ala Tyr Gln Asn Glu Glu Ile Thr Ala Leu Lys Ile Lys
            210                 215                 220

Tyr Asn Pro Phe Ala Lys Ala Phe Leu Asp Ala Lys Glu Arg Ser Asp
225                 230                 235                 240

His Lys Glu Met Met Glu Glu Pro Gly Asp Ser Gln Gln Pro Gly Tyr
                245                 250                 255

Ser Gln Trp Gly Trp Leu Leu Pro Gly Thr Ser Thr Leu Cys Pro Pro
                260                 265                 270

Ala Asn Pro His Pro Gln Phe Gly Gly Ala Leu Ser Leu Pro Ser Thr
            275                 280                 285

His Ser Cys Asp Arg Tyr Pro Thr Leu Arg Ser His Arg Ser Ser Pro
        290                 295                 300

Tyr Pro Ser Pro Tyr Ala His Arg Asn Asn Ser Pro Thr Tyr Ser Asp
305                 310                 315                 320

Asn Ser Pro Ala Cys Leu Ser Met Leu Gln Ser His Asp Asn Trp Ser
                325                 330                 335

Ser Leu Gly Met Pro Ala His Pro Ser Met Leu Pro Val Ser His Asn
                340                 345                 350

Ala Ser Pro Pro Thr Ser Ser Ser Gln Tyr Pro Ser Leu Trp Ser Val
            355                 360                 365

Ser Asn Gly Ala Val Thr Pro Gly Ser Gln Ala Ala Ala Val Ser Asn
        370                 375                 380

Gly Leu Gly Ala Gln Phe Phe Arg Gly Ser Pro Ala His Tyr Thr Pro
385                 390                 395                 400

Leu Thr His Pro Val Ser Ala Pro Ser Ser Ser Gly Ser Pro Leu Tyr
                405                 410                 415

Glu Gly Ala Ala Ala Thr Asp Ile Val Asp Ser Gln Tyr Asp Ala
            420                 425                 430

Ala Ala Gln Gly Arg Leu Ile Ala Ser Trp Thr Pro Val Ser Pro Pro
        435                 440                 445

Ser Met
    450

<210> SEQ ID NO 71
<211> LENGTH: 449
<212> TYPE: PRT
<213> ORGANISM: Artificial Sequence
<220> FEATURE:
<223> OTHER INFORMATION: Fusion protein comprising Brachyury protein
      Isoform 1 encoded by SEQ ID NO:69

<400> SEQUENCE: 71

Met Ser Lys Lys Gln Val Lys Thr Gln Ser Lys Cys Asn Asn Ile Ser
1               5                   10                  15

Ser Pro Gly Thr Glu Ser Ala Gly Lys Ser Leu Gln Tyr Arg Val Asp
                20                  25                  30

His Leu Leu Ser Ala Val Glu Asn Glu Leu Gln Ala Gly Ser Glu Lys
            35                  40                  45

Gly Asp Pro Thr Glu Arg Glu Leu Arg Val Gly Leu Glu Glu Ser Glu
```

```
            50                  55                  60
Leu Trp Leu Arg Phe Lys Glu Leu Thr Asn Glu Met Ile Val Thr Lys
 65                  70                  75                  80

Asn Gly Arg Arg Met Phe Pro Val Leu Lys Val Asn Val Ser Gly Leu
                 85                  90                  95

Asp Pro Asn Ala Met Tyr Ser Phe Leu Leu Asp Phe Val Ala Ala Asp
                100                 105                 110

Asn His Arg Trp Lys Tyr Val Asn Gly Glu Trp Val Pro Gly Gly Lys
            115                 120                 125

Pro Glu Pro Gln Ala Pro Ser Cys Val Tyr Ile His Pro Asp Ser Pro
        130                 135                 140

Asn Phe Gly Ala His Trp Met Lys Ala Pro Val Ser Phe Ser Lys Val
145                 150                 155                 160

Lys Leu Thr Asn Lys Leu Asn Gly Gly Gln Ile Met Leu Asn Ser
                165                 170                 175

Leu His Lys Tyr Glu Pro Arg Ile His Ile Val Arg Val Gly Gly Pro
            180                 185                 190

Gln Arg Met Ile Thr Ser His Cys Phe Pro Glu Thr Gln Phe Ile Ala
        195                 200                 205

Val Thr Ala Tyr Gln Asn Glu Glu Ile Thr Ala Leu Lys Ile Lys Tyr
    210                 215                 220

Asn Pro Phe Ala Lys Ala Phe Leu Asp Ala Lys Glu Arg Ser Asp His
225                 230                 235                 240

Lys Glu Met Met Glu Glu Pro Gly Asp Ser Gln Gln Pro Gly Tyr Ser
                245                 250                 255

Gln Trp Gly Trp Leu Leu Pro Gly Thr Ser Thr Leu Cys Pro Pro Ala
            260                 265                 270

Asn Pro His Pro Gln Phe Gly Gly Ala Leu Ser Leu Pro Ser Thr His
        275                 280                 285

Ser Cys Asp Arg Tyr Pro Thr Leu Arg Ser His Arg Ser Ser Pro Tyr
    290                 295                 300

Pro Ser Pro Tyr Ala His Arg Asn Asn Ser Pro Thr Tyr Ser Asp Asn
305                 310                 315                 320

Ser Pro Ala Cys Leu Ser Met Leu Gln Ser His Asp Asn Trp Ser Ser
                325                 330                 335

Leu Gly Met Pro Ala His Pro Ser Met Leu Pro Val Ser His Asn Ala
            340                 345                 350

Ser Pro Pro Thr Ser Ser Ser Gln Tyr Pro Ser Leu Trp Ser Val Ser
        355                 360                 365

Asn Gly Ala Val Thr Pro Gly Ser Gln Ala Ala Val Ser Asn Gly
    370                 375                 380

Leu Gly Ala Gln Phe Phe Arg Gly Ser Pro Ala His Tyr Thr Pro Leu
385                 390                 395                 400

Thr His Pro Val Ser Ala Pro Ser Ser Gly Ser Pro Leu Tyr Glu
                405                 410                 415

Gly Ala Ala Ala Ala Thr Asp Ile Val Asp Ser Gln Tyr Asp Ala Ala
            420                 425                 430

Ala Gln Gly Arg Leu Ile Ala Ser Trp Thr Pro Val Ser Pro Pro Ser
        435                 440                 445

Met
```

<210> SEQ ID NO 72
<211> LENGTH: 1516

<212> TYPE: DNA
<213> ORGANISM: Artificial Sequence
<220> FEATURE:
<223> OTHER INFORMATION: Expression Cassette found in mBN345 -
    Promoter + cDNA encoding Fusion protein comprising Brachyury
    (L254V) Protein

<400> SEQUENCE: 72

```
atccgtacag gtttgtttct gaaattcact ttgtaagata cataattaac aaattcaggg      60
ggaaaaatct ttacaaaatt agtatagaag ctatagatat atcaaaggt agacaacaaa     120
taatcagaac ctaattttt tatcaaaaaa ttaaaatata aataaaatga aaaataactt     180
gtatgaagaa aaaatgaaca tgagtaagaa aagctcccct ggcaccgaga gcgcgggaaa     240
gagcctgcag taccgagtgg accacctgct gagcgccgtg gagaatgagc tgcaggcggg     300
cagcgagaag ggcgacccca cagagcgcga actgcgcgtg ggcctggagg agagcgagct     360
gtggctgcgc ttcaaggagc tcaccaatga gatgatcgtg accaagaacg gcaggaggat     420
gtttccggtg ctgaaggtga acgtgtctgg cctggacccc aacgccatgt actccttcct     480
gctggacttc gtggcggcgg acaaccaccg ctggaagtac gtgaacgggg aatgggtgcc     540
ggggggcaag ccggagccgc aggcgcccag ctgcgtctac atccacccg actcgcccaa     600
cttcggggcc cactggatga aggctcccgt ctccttcagc aaagtcaagc tcaccaacaa     660
gctcaacgga gggggccaga tcatgctgaa ctccttgcat aagtatgagc tcgaatcca     720
catagtgaga gttgggggtc cacagcgcat gatcaccagc cactgcttcc ctgagaccca     780
gttcatagcg gtgactgctt atcagaacga ggagatcaca gctcttaaaa ttaagtacaa     840
tccatttgca aaggctttcc ttgatgcaaa ggaaagaagt gatcacaaag agatgatgga     900
ggaacccgga gacagccagc aacctgggta ctcccaatgg gggtggcttc ttcctggaac     960
cagcaccgtt tgtccacctg caaatcctca tcctcagttt ggaggtgccc tctccctccc    1020
ctccacgcac agctgtgaca ggtacccaac cctgaggagc caccggtcct cacccctaccc   1080
cagcccctat gctcatcgga acaattctcc aacctattct gacaactcac ctgcatgttt    1140
atccatgctg caatcccatg acaattggtc cagccttgga atgcctgccc atccagcat    1200
gctccccgtg agccacaatg ccagcccacc taccagctcc agtcagtacc ccagcctgtg    1260
gtctgtgagc aacggcgccg tcaccccggg ctcccaggca gcagccgtgt ccaacgggct    1320
gggggcccag ttcttccggg gctccccgc gcactacaca cccctcaccc atccggtctc    1380
ggcgccctct tcctcgggat ccccactgta cgaaggggcg ccgcggcca cagacatcgt    1440
ggacagccag tacgacgccg cagcccaagg ccgcctcata gcctcatgga cactgtgtc    1500
gccaccttcc atgtga                                                   1516
```

<210> SEQ ID NO 73
<211> LENGTH: 1552
<212> TYPE: DNA
<213> ORGANISM: Artificial Sequence
<220> FEATURE:
<223> OTHER INFORMATION: Expression Cassette found in mBN355 -
    Promoter + cDNA encoding Fusion protein comprising Brachyury
    (L254V) Protein

<400> SEQUENCE: 73

```
atccgtacag gtttgtttct gaaattcact ttgtaagata cataattaac aaattcaggg      60
ggaaaaatct ttacaaaatt agtatagaag ctatagatat atcaaaggt agacaacaaa     120
taatcagaac ctaattttt tatcaaaaaa ttaaaatata aataaaatga aaaataactt     180
```

| | |
|---|---|
| gtatgaagaa aaaatgaaca tgagtaagaa acaagtaaaa actcaaagta aatgtaataa | 240 |
| tatcatgagc tccccctggca ccgagagcgc gggaaagagc ctgcagtacc gagtggacca | 300 |
| cctgctgagc gccgtggaga tgagctgca ggcgggcagc gagaagggcg accccacaga | 360 |
| gcgcgaactg cgcgtgggcc tggaggagag cgagctgtgg ctgcgcttca aggagctcac | 420 |
| caatgagatg atcgtgacca agaacggcag gaggatgttt ccggtgctga aggtgaacgt | 480 |
| gtctggcctg accccaacg ccatgtactc cttcctgctg acttcgtgg cggcggacaa | 540 |
| ccaccgctgg aagtacgtga acggggaatg ggtgccgggg ggcaagccgg agccgcaggc | 600 |
| gcccagctgc gtctacatcc accccgactc gcccaacttc ggggcccact ggatgaaggc | 660 |
| tcccgtctcc ttcagcaaag tcaagctcac caacaagctc aacggagggg ccagatcat | 720 |
| gctgaactcc ttgcataagt atgagcctcg aatccacata gtgagagttg ggggtccaca | 780 |
| gcgcatgatc accagccact gcttccctga gacccagttc atagcggtga ctgcttatca | 840 |
| gaacgaggag atcacagctc ttaaaattaa gtacaatcca tttgcaaagg ctttccttga | 900 |
| tgcaaaggaa agaagtgatc acaaagagat gatggaggaa cccggagaca gccagcaacc | 960 |
| tgggtactcc caatgggggt ggcttcttcc tggaaccagc accgtttgtc cacctgcaaa | 1020 |
| tcctcatcct cagtttggag gtgccctctc cctcccctcc acgcacagct gtgacaggta | 1080 |
| cccaacccctg aggagccacc ggtcctcacc ctaccccagc ccctatgctc atcggaacaa | 1140 |
| ttctccaacc tattctgaca actcacctgc atgtttatcc atgctgcaat cccatgacaa | 1200 |
| ttggtccagc cttggaatgc ctgcccatcc cagcatgctc cccgtgagcc acaatgccag | 1260 |
| cccacctacc agctccagtc agtaccccag cctgtggtct gtgagcaacg cgccgtcac | 1320 |
| cccgggctcc caggcagcag ccgtgtccaa cgggctgggg gcccagttct tccggggctc | 1380 |
| ccccgcgcac tacacacccc tcacccatcc ggtctcggcg ccctcttcct cgggatcccc | 1440 |
| actgtacgaa ggggcggccg cggccacaga catcgtggac agccagtacg acgccgcagc | 1500 |
| ccaaggccgc ctcatagcct catggacacc tgtgtcgcca ccttccatgt ga | 1552 |

<210> SEQ ID NO 74
<211> LENGTH: 1464
<212> TYPE: DNA
<213> ORGANISM: Artificial Sequence
<220> FEATURE:
<223> OTHER INFORMATION: Expression Cassette found in mBN343 -
    Promoter + cDNA encoding Fusion protein comprising Brachyury
    (L254V) Protein

<400> SEQUENCE: 74

| | |
|---|---|
| taatgtatag aactaatta taataaacat agtaaatatg ggtaacttct taatagccat | 60 |
| aattaaaatt gaaaaaaaaa tatcattata aaacgtaaac gaacaaaaaa cattaattga | 120 |
| tccccccct gtctccccc tccagattga gcaatcatga gctcccctgg caccgagagc | 180 |
| gcgggaaaga gcctgcagta ccgagtggac cacctgctga gcgccgtgga aatgagctg | 240 |
| caggcgggca gcgagaaggg cgaccccaca gagcgcgaac tgcgcgtggg cctggaggag | 300 |
| agcgagctgt ggctgcgctt caaggagctc accaatgaga tgatcgtgac caagaacggc | 360 |
| aggaggatgt ttccggtgct gaaggtgaac gtgtctggcc tgaccccaa cgccatgtac | 420 |
| tccttcctgc tggacttcgt ggcggcggac aaccaccgct ggaagtacgt gaacggggaa | 480 |
| tgggtgccgg ggggcaagcc ggagccgcag gcgcccagct gcgtctacat ccaccccgac | 540 |
| tcgcccaact tcggggccca ctggatgaag gctcccgtct ccttcagcaa agtcaagctc | 600 |
| accaacaagc tcaacggagg gggccagatc atgctgaact cccttgcataa gtatgagcct | 660 |

```
cgaatccaca tagtgagagt tgggggtcca cagcgcatga tcaccagcca ctgcttccct    720
gagacccagt tcatagcggt gactgcttat cagaacgagg agatcacagc tcttaaaatt    780
aagtacaatc catttgcaaa ggctttcctt gatgcaaagg aaagaagtga tcacaaagag    840
atgatggagg aacccggaga cagccagcaa cctgggtact cccaatgggg gtggcttctt    900
cctggaacca gcaccgtttg tccacctgca atcctcatc ctcagtttgg aggtgccctc     960
tccctcccct ccacgcacag ctgtgacagg tacccaaccc tgaggagcca ccggtcctca   1020
ccctacccca gccctatgc tcatcggaac aattctccaa cctattctga caactcacct   1080
gcatgtttat ccatgctgca atcccatgac aattggtcca gccttggaat gcctgcccat   1140
cccagcatgc tccccgtgag ccacaatgcc agcccaccta ccagctccag tcagtacccc   1200
agcctgtggt ctgtgagcaa cggcgccgtc accccgggct cccaggcagc agccgtgtcc   1260
aacgggctgg gggcccagtt cttccggggc tcccccgcgc actacacacc cctcacccat   1320
ccggtctcgg cgccctcttc ctcgggatcc ccactgtacg aaggggcggc cgcggccaca   1380
gacatcgtgg acagccagta cgacgccgca gcccaaggcc gcctcatagc ctcatggaca   1440
cctgtgtcgc caccttccat gtga                                          1464
```

<210> SEQ ID NO 75
<211> LENGTH: 1478
<212> TYPE: DNA
<213> ORGANISM: Artificial Sequence
<220> FEATURE:
<223> OTHER INFORMATION: Expression Cassette found in mBN344 -
      Promoter + cDNA encoding Fusion protein comprising Brachyury
      (L254V) Protein

<400> SEQUENCE: 75

```
tatccgtaca ggtttgtttc tgaaattcac tttgtaagat acataattaa caaattcagg     60
gggaaaaatc tttacaaaat tagtatagaa gctatagata tatcaaaagg tagacaacaa    120
ataatcagaa cctaattttt ttatcaaaaa attaaaatat aaataaaatc atgagctccc    180
ctggcaccga gagcgcggga aagagcctgc agtaccgagt ggaccacctg ctgagcgccg    240
tggagaatga gctgcaggcg ggcagcgaga agggcgaccc cacagagcgc gaactgcgcg    300
tgggcctgga ggagagcgag ctgtggctgc gcttcaagga gctcaccaat gagatgatcg    360
tgaccaagaa cggcaggagg atgtttccgg tgctgaaggt gaacgtgtct ggcctggacc    420
ccaacgccat gtactccttc ctgctggact tcgtggcggc ggacaaccac cgctggaagt    480
acgtgaacgg ggaatgggtg ccggggggca gccggagcc gcaggcgccc agctgcgtct    540
acatccaccc cgactcgccc aacttcgggg cccactggat gaaggctccc gtctccttca    600
gcaaagtcaa gctcaccaac aagctcaacg agggggccca gatcatgctg aactccttgc    660
ataagtatga gcctcgaatc cacatagtga gagttggggg tccacagcgc atgatcacca    720
gccactgctt ccctgagacc cagttcatag cggtgactgc ttatcagaac gaggagatca    780
cagctcttaa aattaagtac aatccatttg caaaggcttt ccttgatgca aaggaaagaa    840
gtgatcacaa agagatgatg gaggaacccg gagacagcca gcaacctggg tactcccaat    900 ggggggtggct tcttcctgga accagcaccg tttgtccacc tgcaaatcct catcctcagt    960
ttggaggtgc cctctcccctc ccctccacgc acagctgtga caggtaccca accctgagga   1020
gccaccggtc ctcaccctac cccagcccct atgctcatcg gaacaattct ccaacctatt   1080
ctgacaactc acctgcatgt ttatccatgc tgcaatccca tgacaattgg tccagccttg   1140
```

```
gaatgcctgc ccatcccagc atgctccccg tgagccacaa tgccagccca cctaccagct    1200
ccagtcagta ccccagcctg tggtctgtga gcaacggcgc cgtcaccccg ggctcccagg    1260
cagcagccgt gtccaacggg ctgggggccc agttcttccg gggctccccc gcgcactaca    1320 caccccctcac ccatccggtc tcggcgccct cttcctcggg atccccactg tacgaagggg    1380
cggccgcggc cacagacatc gtggacagcc agtacgacgc cgcagcccaa ggccgcctca    1440
tagcctcatg gacacctgtg tcgccaccct tccatgtga                           1478
```

<210> SEQ ID NO 76
<211> LENGTH: 1486
<212> TYPE: DNA
<213> ORGANISM: Artificial Sequence
<220> FEATURE:
<223> OTHER INFORMATION: Expression Cassette found in mBN354 -
      Promoter + cDNA encoding Fusion protein comprising Brachyury
      (L254V) Protein

<400> SEQUENCE: 76

```
atccgtacag gtttgtttct gaaattcact ttgtaagata cataattaac aaattcaggg      60
ggaaaaatct ttacaaaatt agtatagaag ctatagatat atcaaaaggt agacaacaaa     120
taatcagaac ctaattttt tatcaaaaaa ttaaaatata aataaaatga aaaataactt     180
gagctcccct ggcaccgaga gcgcgggaaa gagcctgcag taccgagtgg accacctgct    240
gagcgccgtg gagaatgagc tgcaggcggg cagcgagaag ggcgacccca cagagcgcga    300
actgcgcgtg ggcctggagg agagcgagct gtggctgcgc ttcaaggagc tcaccaatga    360
gatgatcgtg accaagaacg gcaggaggat gtttccggtg ctgaaggtga acgtgtctgg    420
cctggacccc aacgccatgt actccttcct gctggacttc gtggcggcgg acaaccaccg    480
ctggaagtac gtgaacgggg aatgggtgcc gggggggcaag ccggagccgc aggcgcccag    540
ctgcgtctac atccaccccg actcgcccaa cttcggggcc cactggatga aggctcccgt    600
ctccttcagc aaagtcaagc tcaccaacaa gctcaacgga gggggccaga tcatgctgaa    660
ctccttgcat aagtatgagc ctcgaatcca catagtgaga gttgggggtc cacagcgcat    720
gatcaccagc cactgcttcc ctgagaccca gttcatagcg gtgactgctt atcagaacga    780
ggagatcaca gctcttaaaa ttaagtacaa tccatttgca aaggctttcc ttgatgcaaa    840
ggaaagaagt gatcacaaag agatgatgga ggaacccgga gacagccagc aacctgggta    900
ctcccaatgg gggtggcttc ttcctggaac cagcaccgtt tgtccacctg caaatcctca    960
tcctcagttt ggaggtgccc tctccctccc ctccacgcac agctgtgaca ggtacccaac    1020
cctgaggagc caccggtcct caccctaccc cagcccctat gctcatcgga caattctcc    1080 aacctattct gacaactcac ctgcatgttt atccatgctg caatcccatg acaattggtc    1140
cagccttgga atgcctgccc atcccagcat gctccccgtg agccacaatg ccagcccacc    1200
taccagctcc agtcagtacc ccagcctgtg gtctgtgagc aacggcgccg tcaccccggg    1260
ctcccaggca gcagccgtgt ccaacgggct gggggcccag ttcttccggg gctcccccgc    1320
gcactacaca cccctcaccc atccggtctc ggcgccctct tcctcgggat ccccactgta    1380
cgaaggggcg gccgcggcca cagacatcgt ggacagccag tacgacgccg cagcccaagg    1440
ccgcctcata gcctcatgga cacctgtgtc gccaccttcc atgtga                   1486
```

<210> SEQ ID NO 77
<211> LENGTH: 182
<212> TYPE: DNA
<213> ORGANISM: Artificial Sequence -continued

```
<220> FEATURE:
<223> OTHER INFORMATION: Promoter Sequence with nucleotides 5' of Gene
      FPV 088 + 15 nucleotides

<400> SEQUENCE: 77
tatccgtaca ggtttgtttc tgaaattcac tttgtaagat acataattaa caaattcagg      60
gggaaaaatc tttacaaaat tagtatagaa gctatagata tatcaaaagg tagacaacaa     120
ataatcagaa cctaattttt ttatcaaaaa attaaaatat aaataaaatg aaaaataact     180
tg                                                                    182
```

CASSETTE ENCODING A FPV/BRACHYURY FUSION PROTEIN

This application is a National Phase application under 35 U.S.C. § 371 of International Application No. PCT/IB2016/001183, filed Jul. 28, 2016, and claims the benefit under 35 U.S.C. § 119(e) of U.S. Provisional Patent Application 62/199,681, filed Jul. 31, 2015, the disclosures of which are incorporated by reference herein in their entirety.

FIELD OF THE INVENTION

The present invention relates to one or more novel promoters of protein expression in poxviruses, especially avipoxviruses such as fowlpoxvirus and canarypoxvirus. The invention further relates to polynucleotides comprising said promoter, in particular, polynucleotides comprising said promoter and a nucleic acid to be expressed; vectors comprising the same; host cells comprising the above constructs; and compositions comprising any of the above. Additionally the invention relates to one or more novel polypeptides operably linked to the one or more promoters. More particularly, the one or more novel polypeptides are related to the Brachury protein.

BACKGROUND OF THE INVENTION

Recombinant poxviruses have been used as vaccines for infectious organisms and, more recently, for tumors. Mastrangelo et al. J Clin Invest. 2000; 105(8):1031-1034. Two of these poxvirus groups, avipoxvirus and orthopoxvirus, have been shown to be effective at battling tumors and have been involved with potential cancer treatments. Id.

One exemplary avipoxvirus species, fowlpox, has been shown to be a safe vehicle for human administrations as fowlpox virus enters mammalian cells and expresses proteins, but replicates abortively. Skinner et al. Expert Rev Vaccines. 2005 February; 4(1):63-76. Additionally, the use of fowlpox virus as a vehicle for expression is being evaluated in numerous clinical trials of vaccines against cancer, malaria, tuberculosis, AIDS, and EBOLA. Id.

Recombinant poxviruses, such as fowlpox, has been used to express a wide range of inserted genes, including several infectious disease and tumor associated genes such as p97, HER-2/neu, p53 and ETA (Paoletti, et al., 1993). One exemplary tumor antigen that is recently being studied is Brachyury (also known as "T").

Brachyury was identified in mice as a dominant short tail mutant that is also a recessive lethal; homozygous T/T embryos die in mid-gestation due to a failure of posterior mesoderm formation (Chesley, J. Exp. Zool., 70: 429-459, 1935). The murine Brachyury gene has been cloned (Herrmann et al., Nature (Lond.), 343: 617-622, 1990), as well as the homologs in other species, such as humans. The expression of the human homologue of the mouse Brachyury was detected by RT-PCR in the notochord remnant, the nucleus pulposus, of human abortuses at 14-15 weeks gestation (Edwards et al., Genome Res., 6: 226-233, 1996).

Brachyury has generally proved to be a valuable marker for recognition of mesodermal differentiation (Herrmann et al., Trends Genet., 10: 280-286, 1994). For example, apart from expression in embryos themselves, Brachyury has been reported to be activated during the differentiation of certain murine EC and ES cell lines differentiating along mesodermal lineages in vitro (see, for example, Bain et al., Biochem. Biophys. Res. Commun., 223: 691-694, 1996). In humans, Brachyury has been shown to be expressed in teratocarcinomas (Gokhele et al., Cell Growth and Differentiation 11:157-62, 2000), chordomas (Vujovic et al., J. Pathol. 2: 157-65, 2006) and hemagioblastomas (Glasker et al., Cancer Res. 66: 4167-4172, 2006).

More recently, it has been described that poxviruses expressing Brachyury can be effective as an active immunotherapeutic against tumors. (See, WO 2014/043535).

There is clearly a substantial unmet medical need for improving infectious disease and cancer treatments, including active immunotherapies and vaccines. Based on the above, a need in the art exists for improving expression of antigens, like Brachyury, used in active immunotherapies. The present invention fulfills this need.

BRIEF SUMMARY OF THE INVENTION

The present invention provides one or more promoters, nucleic acids, expression cassettes, recombinant peptides, and recombinant poxviruses associated with enhancements in expression of coding sequences and antigens incorporated as part of poxviruses In one aspect of the invention, there is an expression cassette comprising:

a. a promoter comprising a nucleic sequence having at least 70% identity to any one of SEQ ID NOs: 1-10, and 77; and b. a coding sequence operably linked to the promoter;

wherein expression of the coding sequence is controlled by the promoter.

In further aspects of the present invention, the expression cassette can be incorporated as part of a vector such as a virus or plasmid, for enhanced expression of the coding sequence therein. Preferably, the expression cassette is part of a poxvirus, such as but not limited to, orthopoxvirus and avipoxvirus. More preferably, the expression cassette is an avipoxvirus such as fowlpoxvirus. In still further aspects, the expression cassette is not an expression cassette that naturally occurs in the genome of a poxvirus.

In additional aspects, there are one or more promoters comprising or consisting of a) a nucleic acid sequence selected from the group consisting of SEQ ID NOs: 1-10, b) a subsequence of any one of SEQ ID NOs: 1-10, and 77, or c) a derivative sequence of any one of SEQ ID NOs: 1-10, and 77, wherein the derivative has one or more substitutions, deletions, and/or insertions, and wherein the derivative sequence is active as a poxvirus promoter and/or active in a poxvirus infected cell.

In still additional aspects, the present invention includes one or more nucleic acid sequences encoding one or more novel Brachyury proteins selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71. In yet further aspects, the present invention includes one more novel nucleic acid sequences selected from the group consisting of: 16-17, 20-21, 24-25, 28-29, 32-33, 36-37, 40-41, 44-45, 48-49, 52-53, 56-57, 60-61, 64-65, 68, and 69.

In still further aspects, the present invention includes an expression cassette comprising:

a. a promoter comprising a nucleic acid sequence having at least 70% identity to any one of SEQ ID NOs: 1-10, and 77; and b. a coding sequence operably linked to the promoter, wherein the coding sequences includes either i) a nucleic acid encoding a Brachyury protein selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71 or ii) comprises or consists of a nucleic acid having at least 70% identity to any one of the nucleic acids selected from the group consisting of: SEQ ID NOs12, 14-17, 20-21, 24-25, 28-29, 32-33, 36-37, 40-41, 44-45, 48-49, 52-53, 56-57, 60-61, 64-65, 68, and 69; wherein expression of the coding sequence is controlled by the promoter.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 6 depicts expression of Brachyury and TRICOM proteins in CMMT cells (a rhesus macaque mammary tumor cell line) infected with a recombinant virus FPV-mBN345B assessed by flow cytometry, as described in Example 4.

DETAILED DESCRIPTION OF THE INVENTION

Figure 1:
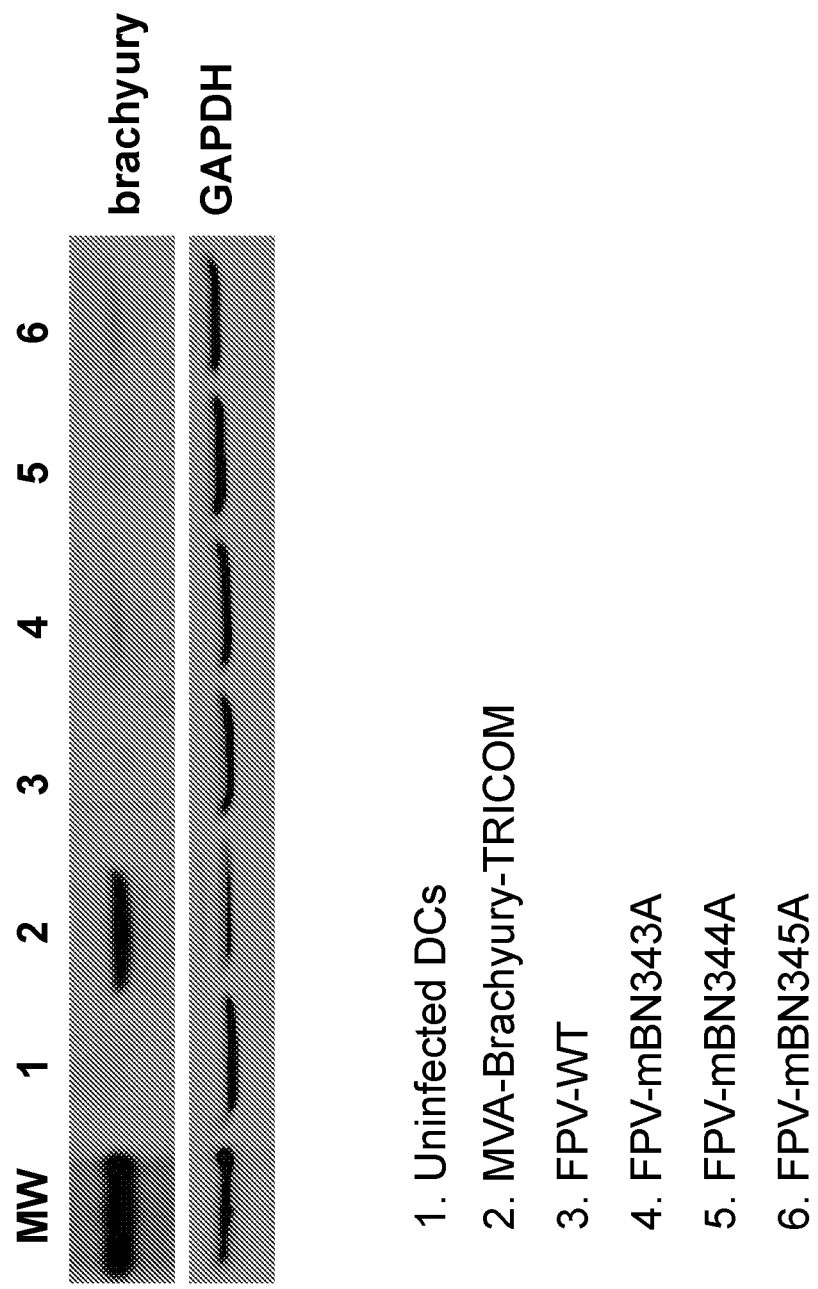
FIG. 1 illustrates expression of the Brachyury protein in human dendritic cells (DCs) infected with the non-recombinant virus FPV-WT, or recombinant viruses FPV-mBN343A, FPV-mBN344A, or FPV-mBN345A. A western blot analysis was performed using rabbit monoclonal anti-Brachyury antibody as detailed in Example 1.

The invention is based on the surprising determination that the promoter sequences as set out in SEQ ID NOs:1-10, and 77 enhance expression of the tumor antigen Brachyury. Shown in FIGS. 1-6 and described in more detail herein, expression of Brachyury antigen is enhanced when using promoters of present invention. Expression is further enhanced when the promoters and Brachyury antigen are used as part of a recombinant poxvirus.

In at least one aspect, the various embodiments of the present disclosure were created as a result of insufficient expression levels of Brachyury protein using known Vaccinia promoters, such as PrS and Vaccinia virus 40k (VV-40K). In trying to enhance Brachyury expression levels, the present inventors analyzed various vaccinia promoters and associated proteins (e.g., VV-40k, 13, etc.) and any possible homologues in FPV. The inventors realized that some FPV homologous sequences were previously discovered. See, e.g., Zantinge, J Gen Virol. 1996 April; 77 (Pt 4):603-14 and Gene FPV 088 at NCBI Reference Sequence: NP 039051.1, Afonso, C. L et al., J. Virol. 74 (8), 3815-3831 (2000).

In an initial attempt to enhance Brachyury expression, a possible promoter region of Gene FPV 088 at NCBI Reference Sequence: NP_039051.1 was constructed with Brachyury by the inventors and tested yielding undesired results (see, e.g., FIGS. 1 and 2 at mBN344A) promoter. The inventors created a subsequent promoter with an addition of nucleotides from the ORF of Gene FPV 088, which similarly yielded undesired results. (see, e.g., FIGS. 1 and 2 at mBN354A). Further constructs were created by the present inventors with yet additional nucleotides from the ORF of Gene FPV 088, which, as described and illustrated herein, enhance expression of the tumor antigen Brachyury.

Thus, in various embodiments, the present invention is directed to one or more nucleic acid sequences, one or more promoters comprising the nucleic acids sequences, one or more expression cassettes comprising the nucleic acids, one or more peptides and/or peptide sequences for enhancing/ expression of coding sequences and/or nucleic acids in expression vectors such as, but not limited to, plasmids, recombinant virus and so forth. In further embodiments, the present invention is directed to one or more recombinant poxviruses comprising one or more of the nucleic acid sequences, promoters, expression cassettes, and/or peptides and/or peptide sequences described herein.

Additionally, in various embodiments of the invention, there are one or more nucleic acids sequences encoding brachyury polypeptides. In one embodiment, the one or more nucleic acids encoding a brachyury polypeptide are selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71. The nucleotide sequences encoding the brachyury polypeptides according to the present invention are selected from the group consisting of: SEQ ID NOs: 12, 14-17, 20-21, 24-25, 28-29, 32-33, 36-37, 40-41, 44-45, 48-49, 52-53, 56-57, 60-61, 64-65, 68, and 69.

Definitions

It must be noted that, as used herein, the singular forms "a", "an", and "the", include plural references unless the context clearly indicates otherwise. Thus, for example, reference to "an epitope" includes one or more of epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), though less preferred, whenever used herein in the context of an aspect or embodiment of the present invention can be substituted with the term "consisting of." When used herein "consisting of excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "promoter" denotes a regulatory region of nucleic acid, usually DNA, located upstream of the sequence of a nucleic acid to be expressed, which contains specific DNA sequence elements, that are recognized and bound e.g. by protein transcription factors and polymerases responsible for synthesizing the RNA from the coding region of the gene being promoted. As promoters are typically immediately adjacent to the gene in question, positions in the promoter are designated relative to the transcriptional start site, where transcription of DNA begins for a particular gene (i.e., positions upstream are negative numbers counting back from −1, for example −100 is a position 100 base pairs upstream). Thus, the promoter sequence may comprise nucleotides until position −1. However, nucleotides from position +1 are not part of the promoter, i.e. in this regard it has to be noted that the translation initiation codon (ATG or AUG) is not part of the promoter. Thus, SEQ ID NOs: 1-10, and 77 are polynucleotides comprising promoters of the invention.

As used herein, the term "enhancing" or "enhanced" when used with respect to expression levels of a coding sequence, nucleic acid, protein, and/or antigen, refers to an increase in expression of a coding sequence, nucleic acid, protein, and/or antigen when associated with and/or as part of one or more of the promoters, expression cassettes, nucleic acids, proteins, and/or vectors of the present invention relative to expression levels of a coding sequence, nucleic acids, protein, and/or antigen when associated with and/or as part of one or more of the promoters know in the art, such as PrS or VV-40k.

As used herein, a nucleotide sequence having "essentially the same expression characteristics" as the nucleotide sequence set out in SEQ ID NO s: 1-10, and 77 will exhibit at least 70%, preferably at least 80%, even more preferably at least 90% of the promoter activity of SEQ ID NO s: 1-10, and 77, as measured by amount of recombinant protein produced. Whether or not a promoter sequence in question has "essentially the same expression characteristics" as any of SEQ ID NO s: 1-10, and 77 may be readily determined by one of ordinary skill in the art using the methods set forth in Examples 1-4 of the present application. The promoters according to the present invention are preferably active as poxvirus promoters, preferably avipoxvirus or active as promoters in poxvirus infected cells, preferably avipoxvirus infected cells. The avipoxvirus is preferably Fowlpox virus. "Active as pox virus promoter" means that the promoter is able to direct the expression of a gene to which it is operably linked in a pox virus after infection of cells with said virus. The cells are preferably cells that allow late and/or early and/or early/late expression of the poxvirus. "A promoter active in poxvirus infected cells" includes also the situation in which the promoter is not part of a poxvirus genome, e.g. part of a plasmid or linear polynucleotide or a non-poxvirus viral genome; in such a situation the promoter according to the present invention is active if the cell comprising the promoter also comprises a poxvirus genome, e.g. if the cell is infected with a poxvirus. Under these circumstances the viral RNA polymerase recognizes the promoter according to the present invention and the expression of the gene/coding sequence that is linked to the promoter is activated.

As used herein, the term "derived from the nucleic acid set out in SEQ ID NOs: 1-10, and 77" means that the nucleotide sequence of SEQ ID NOs: 1-10, and 77 is taken as a basis for effecting the nucleotide modifications specified, for example, at least one nucleotide addition, deletion, substitution and/or inversion. The term "derived" includes the possibility, for example, of actually modifying the physical sequence corresponding to SEQ ID NOs: 1-10, and 77 by known methods, for example, error-prone PCR. The term "derived" additionally includes the possibility of performing modifications on the sequence of SEQ ID NOs: 1-10, and 77 in silico, and then synthesizing the thus determined sequence as a physical nucleic acid. For example, the term "derived" encompasses the possibility of using any known computer program for the analysis of nucleic acid sequences with regard to, for example, hybridization stability and the possibility of any secondary nucleic acid structure in modifying the starting sequence of SEQ ID NOs: 1-10, and 77. Preferably, not more than 10, 9, 8, 7, 6, 5, 4, 3, 2 or 1 nucleotides have been added, deleted, substituted and/or inverted from the nucleic acids of SEQ ID NOs: 1-10, and 77. Furthermore, addition, insertion or deletion of at least one nucleotide should not result to a start codon of the nucleic acid to be expressed.

As used herein, the terms "expressed", "express", "expression" and the like denote the transcription alone as well as both the transcription and translation of a sequence of interest. Thus, in referring to expression of a nucleic acid present in the form of DNA, the product resulting from this expression may be either RNA (resulting from transcription alone of the sequence to be expressed) or a polypeptide sequence (resulting from both transcription and translation of the sequence to be expressed). The term "expression" thus also includes the possibility that both RNA and polypeptide product result from said expression and remain together in the same shared milieu. For example, this is the case when the mRNA persists following its translation into polypeptide product.

As used herein, the term "expression cassette" is defined as a part of a vector or recombinant virus typically used for cloning and/or transformation. An expression cassette is typically comprised of a) one or more coding sequences (e.g., open reading frame (ORF), genes, nucleic acids encoding a protein and/or antigen), and b) sequences controlling expression the one or more coding sequences. Additionally, an expression cassette may comprise a 3' untranslated region that in eukaryotes usually contain a polyadenylation site.

The term "recombinant" means a polynucleotide or polypeptide of semi-synthetic, or synthetic origin which either does not occur in nature or is linked to another polynucleotide in an arrangement not found in nature.

One aspect of the invention includes promoters with nucleic acids having at least 70%, preferably 75%, 80%, 85%, 90% or 95% identity with SEQ ID NOs: 1-10, and 77 and having essentially the same expression characteristics as SEQ ID NOs: 1-10, and 77.

"Percent (%) sequence homology or identity" with respect to nucleic acid sequences described herein is defined as the percentage of nucleotides in a candidate sequence that are identical with the nucleotides in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent nucleotide sequence identity or homology can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

For example, an appropriate alignment for nucleic acid sequences is provided by the local homology algorithm of Smith and Waterman, (1981), Advances in Applied Mathematics 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6):6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://http://blast.ncbi.nlm.nih.gov/.

Promoters and Nucleic Acid Sequences

In one embodiment, the present disclosure includes a nucleic acid sequence selected from the group consisting of SEQ ID NOs: 1-10, and 77.

In another embodiment, the present disclosure includes a nucleic acid sequence having at least 70% identity with a nucleic acid selected from the group consisting of SEQ ID NOs: 1-10, and 77 and having essentially the same expression characteristics as a nucleic acid sequence selected from the group consisting of SEQ ID NOs: 1-10, and 77. In further embodiments, there is a nucleic acid sequence having at least 75%, 80%, 85%, 90%, or 95% identity with a nucleic acid selected from the group consisting of SEQ ID NOs: 1-10, and 77 and having essentially the same expression characteristics as a nucleic acid sequence selected from the group consisting of SEQ ID NOs: 1-10, and 77.

In yet additional embodiment, there is a nucleic acid having a nucleotide sequence derived from the nucleic acid set out in SEQ ID NOs: 1-10, and 77, comprising at least one nucleotide addition, deletion, substitution and/or inversion as compared to the nucleotide sequence of SEQ ID NOs: 1-10, and 77 and having essentially the same expression characteristics as the nucleic acid of SEQ ID NOs: 1-10, and 77.

In still an additional embodiment, there is a nucleic acid having a nucleotide sequence capable of hybridizing to a nucleic acid sequence selected from the group consisting of SEQ ID NOs: 1-10, and 77, and having essentially the same expression characteristics as a nucleic acid sequence selected from the group consisting of SEQ ID NOs: 1-10, and 77.

In one aspect of the invention, there is a promoter for enhancing the expression of a coding and/or gene sequence, the promoter selected from the group consisting of:
  a) a nucleic acid sequence selected from the group consisting of SEQ ID NOs: 1-10, and 77 or a subsequence thereof;
  b) a nucleic acid having a nucleotide sequence derived from the nucleic acid set out in (a), comprising at least one nucleotide addition, deletion, substitution and/or inversion as compared to the nucleotide sequence of (a) and having essentially the same expression characteristics as the nucleic acid of (a);
  c) a nucleic acid sequence having at least 70% identity with the nucleic acid of (a) and having essentially the same expression characteristics as the nucleic acid of (a); and
  d) a nucleic acid capable of hybridizing to a nucleic acid sequence of (a), (b) or (c) and having essentially the same expression characteristics as the nucleic acid of (a).
  e) a nucleic acid sequence comprising SEQ ID NOs:3, 4, 5, 6, 7, 8, or 9, wherein the nucleic acid sequence includes up to 245 nucleotides.

A further aspect of the invention relates to a nucleic acid capable of hybridizing to a nucleic acid sequence of (a), (b) or (c) and having essentially the same expression characteristics as the nucleic acid of (a). The term "capable of hybridizing" means hybridization in conditions in which any portion of the nucleic acid of (a), (b) or (c) is able to hybridize to another DNA sequence to allow detection and isolation of any DNA sequence having essentially the same expression characteristics as the nucleic acid of (a). The hybridization is carried out in stringent conditions; the more stringent the conditions, the more likely partially complementary sequences are to be forced apart, i.e. higher stringency lowers the probability of hybridization. In practice, the term "stringent conditions" means hybridization conditions with high temperature (e.g. 65° C.) and/or low salt concentration (e.g. 0.1×SSC). Increasing the temperature and/or decreasing the salt concentration increases the stringency. Under stringent conditions hybridization will occur only if there is at least 70% or preferably at least 75, 80, 85, 90 or 95% identity between the sequences. Hybridization can be carried out as set out in Ausubel et al. (2002) Short Protocols in Molecular Biology Vol. 1 5th ed. Canada.

Preferably, the promoter and/or nucleic acid of the invention has a length of up to and including 245 or 242 nucleotides. Also, the promoter and/or nucleic acid of the invention has a length of up to and including 232 or 215 nucleotides. More preferably, the promoter of the invention has a length of up to and including 212, 200, or a length of up to and including 195 nucleotides, or a length of up to and including 183, or a length of up to and including 170 or 167 nucleotides. In one embodiment, the nucleic acid of (b), (c) or (d), as set out above, comprises about 50-250 nucleotides, about 60-220 nucleotides, about 70-200 nucleotides, about 80-190 nucleotides, or about 90-180 nucleotides.

Alternatively it is within the scope of the present invention to use a derivative of these promoters, which may be a subsequence of the sequences as defined in anyone of SEQ ID NOs: 1-10, and 77. The term "subsequence of the sequences according to anyone of SEQ ID NOs: 1-10, and 77" refers to shorter fragments of anyone of SEQ ID NO: 1 to 10, and 77 that are still active as a promoter, in particular as promoter in an orthopoxvirus, such as FPV, or in an orthopoxvirus, such as FPV, infected cells.

In various embodiments, exemplary subsequences of SEQ ID NO:9 are selected from SEQ ID NOs:2-8. In one aspect, SEQ ID NOs: 4 or 5 are preferred subsequence of SEQ ID NO: 9. In other aspects, subsequences of SEQ ID NO: 8 include SEQ ID NOs: 2-7, subsequences of SEQ ID NO:7 include SEQ ID NO: s 2-6, subsequences of SEQ ID NO:6 includes SEQ ID NOs: 2-5, subsequences of SEQ ID NO:5 include SEQ ID NOs: 2-4 subsequences of SEQ ID NO:6 includes SEQ ID NOs: 2-5, subsequences of SEQ ID NO:5 include SEQ ID NOs: 2-4, subsequences of SEQ ID NO: 4 includes SEQ ID NOs: 2-3, and subsequences of SEQ ID NO: 3 includes SEQ ID NO: 2.

The derivative of the promoter comprising or consisting of a nucleotide sequence of anyone of SEQ ID NOs: 1-10, and 77 or subsequences thereof, can also be a sequence that has one or more nucleotide substitutions, deletions and/or insertions with respect to any one of the sequences of SEQ ID NOs: 1-10, and 77. The derivatives according to the present invention are still active as a promoter, in particular as orthopoxvirus and/or avipoxvirus promoter in an orthopoxvirus and/or avipoxvirus virus infected cells, more preferably as an avipoxvirus promoter in avipoxvirus infected cells. In the derivatives according to the present invention deletions, substitutions and insertions may be combined in one sequence.

Preferably the derivative has a homology of at least 40%, more preferably of at least 60%, even more preferably of at least 80%, most preferably of at least 90% when compared to anyone of the sequence of SEQ ID NOs: 1-10, and 77 or subsequences thereof, as described herein.

Brachyury Proteins

In several aspects of the present invention, the inventors' determined that as a result of synthesizing the various promoters described herein, the inventors' created one or more recombinant Brachyury proteins. In particular, the one or more recombinant Brachyury proteins are fusion proteins resulting from the combination of one or more of the promoters of the invention and the Brachyury protein. It is contemplated that one or more of the recombinant Brachyury proteins can be useful as a part of a vaccine, pharmaceutical or other therapeutic composition.

Thus, in various aspects, the invention includes one or more synthetic and novel recombinant Brachyury proteins and/or synthetic and novel nucleic acids encoding recombinant Brachyury proteins.

In one embodiment, there are one or more nucleic acids sequences having at least 70% identity to a nucleic acid encoding a Brachyury protein, wherein the Brachyury protein is selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71. In additional embodiments, there are one or more nucleic acids having at least 75%, 80%, 85%, 90%, or 95% identity to a nucleic acid encoding a Brachyury protein, wherein the Brachyury protein is selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71.

In various other embodiments of the invention, there are one or more Brachyury proteins selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71. In further embodiments, there are one or more Brachyury proteins having at least 70% identity with a peptide selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71. In still further embodiments, there is a peptide having at least 75%, 80%, 85%, 90%, or 95% identity with a peptide selected from the group consisting of SEQ ID NOs: 18-19, 22-23, 26-27, 30-31, 34-35, 38-39, 42-43, 46-47, 50-51, 54-55, 58-59, 62-63, 66-67, 70, and 71.

In another embodiment, there are one or more nucleic acids sequences encoding a Brachyury protein, the nucleic acid sequence selected from the group consisting of: SEQ ID NOs: 16-17, 20-21, 24-25, 28-29, 32-33, 36-37, 40-41, 44-45, 48-49, 52-53, 56-57, 60-61, 64-65, 68, and 69.

In other embodiments, there are one or more nucleic acid sequences having at least 70% identity with a nucleic acid selected from the group consisting of SEQ ID NOs: 16-17, 20-21, 24-25, 28-29, 32-33, 36-37, 40-41, 44-45, 48-49, 52-53, 56-57, 60-61, 64-65, 68, and 69 and having essentially the same expression characteristics as a nucleic acid sequence selected from the group consisting of SEQ ID NOs: 16-17, 20-21, 24-25, 28-29, 32-33, 36-37, 40-41, 44-45, 48-49, 52-53, 56-57, 60-61, 64-65, 68, and 69. In further embodiments, there is a nucleic acid sequence having at least 75%, 80%, 85%, 90%, or 95% identity with a nucleic acid selected from the group consisting of SEQ ID NOs: 16-17, 20-21, 24-25, 28-29, 32-33, 36-37, 40-41, 44-45, 48-49, 52-53, 56-57, 60-61, 64-65, 68, and 69 and having essentially the same expression characteristics as a nucleic acid sequence selected from the group consisting of SEQ ID NOs: 16-17, 20-21, 24-25, 28-29, 32-33, 36-37, 40-41, 44-45, 48-49, 52-53, 56-57, 60-61, 64-65, 68, and 69.

In a preferred embodiment, there are one or more nucleic acid sequences selected from the group consisting of SEQ ID NOs: 16-17, 20-21, 24-25, 28-29, 32-33, 36-37, 40-41, 44-45, 48-49, 52-53, 56-57, 60-61, 64-65, 68, and 69.

Expression Cassettes

According to a further embodiment, the present invention refers to an expression cassette comprising one or more of the promoters and/or Brachyury recombinant proteins and/or nucleic acids according to the present invention.

In one embodiment, there is an expression cassette comprising a promoter having at least 70% identity with a nucleic acid selected from the group consisting of SEQ ID NOs: 1-10 and a nucleic acid encoding a Brachyury peptide selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71. In an another embodiment, there is an expression cassette comprising a promoter selected from the group consisting of SEQ ID NOs: 1-10, and 77 and/or a nucleic acid encoding a Brachyury peptide, wherein the nucleic acid is selected from the group consisting of: SEQ ID NOs: 12, 14-17, 20-21, 24-25, 28-29, 32-33, 36-37, 40-41, 44-45, 48-49, 52-53, 56-57, 60-61, 64-65, 68, and 69.

In a preferred embodiment, there is an expression cassette comprising a nucleic acid sequence at least 70% homologous to a nucleic acid sequence selected from the group consisting of: SEQ ID NOs: 72-76. In further embodiments, there is an expression cassette comprising a nucleic acid sequence having at least 75%, 80%, 85%, 90%, or 95% identity with a nucleic acid selected from the group consisting of SEQ ID NOs:72-76.

In a more preferred embodiment, there is an expression cassette comprising SEQ ID NO: 72.

In a more preferred embodiment, there is an expression cassette comprising SEQ ID NO: 73.

In a more preferred embodiment, there is an expression cassette comprising SEQ ID NO: 74.

Recombinant Poxviruses

According to a further embodiment the nucleic acids, promoters, recombinant proteins, and/or expression cassettes according to the present invention may be part of a vector. The term "vector" refers to any vectors known to the person skilled in the art. A vector can be a plasmid vector such as pBR322 or a vector of the pUC series. More preferably the vector is a recombinant virus. In the context of the present invention the term "virus" or "recombinant virus" refers to an infectious virus comprising a viral genome. In this case the nucleic acids, promoters, recombinant proteins, and/or expression cassettes of the present invention are part of the viral genome of the respective recombinant virus. The recombinant viral genome is packaged and the obtained recombinant viruses can be used for the infection of cells and cell lines, in particular for the infection of living animals including humans. Typical recombinant viruses that may be used according to the present invention are adenoviral vectors, retroviral vectors or vectors on the basis of the adeno associated virus 2 (AAV2). Most preferred are poxviral vectors.

In several embodiments, the nucleic acids, promoters, polypeptides, and expression cassettes according to the present invention are preferably active as poxviral promoters or active as promoters in poxvirus infected cells. The poxvirus is preferably an avipoxvirus or an orthopoxvirus. More preferably, the poxvirus is an avipoxvirus.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

An example of a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5, TROVAC (U.S. Pat. No. 5,766,598), and PDXVAC-TC (U.S. Pat. No. 7,410,644). FP-1 is a Duvette strain modified to be used as a vaccine in one-day old chickens. The strain is a commercial fowlpox virus vaccine strain designated O DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

In certain embodiments, the recombinant FPV comprises a nucleic acid sequence selected from the group consisting of: SEQ ID NOs: 1-10, and 77. In various additional embodiments, the recombinant FPV comprises an expression cassette comprising a nucleic acid sequence selected from SEQ ID NOs: 72-76. In a more preferred embodiment, the recombinant FPV comprises an expression cassette comprising a nucleic acid sequence selected from SEQ ID NOs: 72, 73, and 74.

In other embodiments, the recombinant FPV comprises a nucleic acid encoding a brachyury antigen selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71. In further embodiments, the recombinant FPV comprises a Brachyury peptide selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71. In further embodiments, the recombinant FPV comprises a nucleic acid selected from the group consisting of: SEQ ID NOs: 12, 14-17, 20-21, 24-25, 28-29, 32-33, 36-37, 40-41, 44-45, 48-49, 52-53, 56-57, 60-61, 64-65, 68, and 69. In more preferred embodiments, the recombinant FPV comprises a Brachyury peptide selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71 and/or a nucleic acid selected from the group consisting of: SEQ ID NOs: 16-17, 20-21, 24-25, 28-29, 32-33, 36-37, 40-41, 44-45, 48-49, 52-53, 56-57, 60-61, 64-65, 68, and 69.

In the various other embodiments of the present disclosure, the recombinant poxvirus is an orthopoxvirus such as, but not limited to, a vaccinia virus, a Modified Vaccinia Virus Ankara (MVA), or MVA-BN.

Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. A preferred vaccinia virus (VV) strain is the Wyeth (DRYVAX) strain (U.S. Pat. No. 7,410,644). Another preferred VV strain is MVA (Sutter, G. et al. [1994], Vaccine 12: 1032-40). Another preferred VV strain is MVA-BN.

Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, with the deposition number ECACC 94012707 on Jan. 27, 1994, and MVA 575, deposited under ECACC 00120707 on Dec. 7, 2000. MVA-BN, deposited on Aug. 30, 2000 at the European Collection of Cell Cultures (ECACC) under number V00083008, and its derivatives, are additional exemplary strains.

Although MVA-BN is preferred for its higher safety (less replication competent), all MVAs are suitable for this invention. According to an embodiment of the present invention, the MVA strain is MVA-BN and its derivatives. A definition of MVA-BN and its derivatives is given in PCT/EP01/13628 which is incorporated by reference herein.

In one embodiment, the invention encompasses recombinant orthopoxviruses, preferably a vaccinia virus (VV), a Wyeth strain, ACAM 1000, ACAM 2000, MVA, or MVA-BN for cancer therapy. Recombinant orthopoxviruses are generated by insertion of heterologous sequences into an orthopoxvirus.

In certain embodiments, the MVA is MVA-BN, deposited on Aug. 30, 2000, at the European Collection of Cell Cultures (ECACC) under number V00083008, and described in International PCT publication WO2002042480 (see also e.g. U.S. Pat. Nos. 6,761,893, 6,913,752), which are incorporated by reference herein.

In certain embodiments, a recombinant MVA is a derivative of MVA-BN. Such "derivatives" include viruses exhibiting essentially the same replication characteristics as the deposited strain (ECACC No. V00083008), but exhibiting differences in one or more parts of its genome. Viruses having the same "replication characteristics" as the deposited virus are viruses that replicate with similar amplification ratios as the deposited strain in CEF cells and the cell lines, HeLa, HaCat and 143B; and that show similar replication characteristics in vivo, as determined, for example, in the AGR129 transgenic mouse model.

In certain embodiments, the recombinant orthopoxvirus comprises a nucleic acid selected from the group consisting of: SEQ ID NOs: 1-10, and 77. In various additional embodiments, the recombinant orthopoxvirus comprises an expression cassette comprising a nucleic acid sequence selected from SEQ ID NOs: 72-76. In a more preferred embodiment, the recombinant orthopoxvirus comprises an expression cassette comprising a nucleic acid sequence selected from SEQ ID NOs: 72, 73, and 74.

In other embodiments, the recombinant orthopoxvirus comprises a nucleic acid encoding a brachyury antigen selected from the group consisting of: SEQ ID NOs: 11, 13, 18-19, 22-23, 26-27, 30-31, 34-35, 38-39, 42-43, 46-47, 50-51, 54-55, 58-59, 62-63, 66-67, 70, and 71. In further embodiments, the recombinant orthopoxvirus comprises a nucleic acid selected from the group consisting of: SEQ ID NOs: 12, 14-17, 20-21, 24-25, 28-29, 32-33, 36-37, 40-41, 44-45, 48-49, 52-53, 56-57, 60-61, 64-65, 68, and 69. In more preferred embodiments, the recombinant orthopoxvirus comprises a Brachyury peptide selected from the group consisting of: SEQ ID NOs: 18-19, 22-23, 26-27, 30-31, 34-35, 38-39, 42-43, 46-47, 50-51, 54-55, 58-59, 62-63, 66-67, 70, and 71 and/or a nucleic acid selected from the group consisting of: SEQ ID NOs: 16-17, 20-21, 24-25, 28-29, 32-33, 36-37, 40-41, 44-45, 48-49, 52-53, 56-57, 60-61, 64-65, 68, and 69.

Methods are known to the person skilled in the art how the expression cassette or the promoter according to the present invention can be inserted into a viral genome, in particular into the genome of a poxvirus, most preferably into the genome of an orthopoxvirus and/or FPV. For example, the expression cassette or the promoter or derivative thereof according to the present invention may be inserted into the genome of a poxvirus by homologous recombination. To this end a nucleic acid is transfected into a permissive cell line such as CEF or BHK cells, wherein the nucleic acid comprises the expression cassette or the promoter or derivative thereof according to the present invention flanked by nucleotide stretches that are homologous to the region of the poxviral genome in which the expression cassette or the promoter or derivative thereof according to the present invention is to be inserted. The cells are infected by the poxvirus and in the infected cells homologous recombination occurs between the nucleic acid and the viral genome. Alternatively, it is also possible to first infect the cells with a poxvirus and then to transfect the nucleic acid into the infected cells. Again recombination occurs in the cells. The recombinant poxvirus is then selected by methods known in the prior art. The construction of recombinant poxvirus is not restricted to this particular method. Instead, any suitable method known to the person skilled in the art may be used to this end.

The expression cassette or the promoter according to the present invention may be introduced into any suitable part of the virus or viral vector, in particular into a viral, genome. In case of an orthopoxvirus and an avipoxvirus, the insertion may be made into non-essential parts of the viral genome or into an intergenic region of the viral genome. The term "intergenic region" refers preferably to those parts of the viral genome located between two adjacent genes that do not comprise coding sequences. If the virus is an orthopoxvirus and an avipoxvirus the insertion may also be made into a deletion site of the viral genome. The term "deletion site" refers to those parts of the viral genome that are deleted with respect to the genome of a naturally occurring orthopoxvirus or avipoxvirus. However, the insertion sites are not restricted to these preferred insertion sites in the orthopoxvirus and an avipoxvirus genome, since it is within the scope of the present invention that the expression cassette may be inserted anywhere in the viral genome as long as it is possible to obtain recombinants that can be amplified and propagated in at least one cell culture system, such as Chicken Embryo Fibroblasts (CEF cells).

The promoter according to the present invention may be used to express a gene that is already part of the vector, e.g. the genome of an orthopoxvirus and/or an avipoxvirus. Such a gene may be a gene that is naturally part of the viral genome or a foreign gene that has already been inserted into the vector. In these cases the promoter according to the present invention is inserted upstream of the gene in the vector, the expression of which is to be controlled by the promoter.

Vaccines and/or Compositions

According to a further embodiment the invention concerns the vector according to the present invention as vaccine or medicament. In more general term the invention relates to a vaccine or pharmaceutical composition comprising an expression cassette, a DNA or a vector according to the present invention. Methods are known to the person skilled in the art how the vaccine or pharmaceutical composition can be administered to the animal or human body. In case of DNA and recombinant plasmid vectors the DNA and the vector can simply be administered by injection. If the vaccine or composition is a recombinant virus such as an orthopoxvirus or an avipoxvirus, in particular a recombinant MVA or recombinant FPV, it may also be administered to the animal or human body according to the knowledge of the person skilled in the art, e.g. by intra venous, intra muscular, intra nasal, intra dermal or subcutaneous administration. Further details on the amount of virus administered are given below.

The pharmaceutical composition or the vaccine may generally include one or more pharmaceutical acceptable and/or approved carriers, additives, antibiotics, preservatives, adjuvants, diluents and/or stabilizers in addition to the promoter, expression cassette or vector according to the present invention. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of pharmaceutical compositions or vaccines, the DNA, expression cassette or vector according to the present invention, in particular a recombinant orthopoxvirus or avipoxvirus such as recombinant MVA or recombinant FPV is converted into a physiologically acceptable form. For MVA and FPV, this can be done based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titre of $5 \times 10^8$ TCID50/ml formulated in about 10 mM Tris, 140 mM NaCl pH 7.4. For the preparation of vaccine shots, e.g., $10^1$-$10^9$ particles of the recombinant virus according to the present invention are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. A typical virus containing formulation suitable for freeze-drying comprises 10 mM Tris-buffer, 140 mM NaCl, 18.9 g/l Dextran (MW 36000-40000), 45 g/l Sucrose, 0.108 g/l L-glutamic acid mono potassium salt monohydrate pH 7.4. The glass ampoule is then sealed and can be stored between 4° C. and room temperature for several months. However, as long as no need exists the ampoule is stored preferably at temperatures below −20° C.

For vaccination or therapy the lyophilisate or the freeze-dried product can be dissolved in 0.1 to 0.5 ml of an aqueous solution, preferably water, physiological saline or Tris buffer, and administered either systemically or locally, i.e. by parenteral, intramuscular or any other path of administration know to the skilled practitioner. The mode of administration, the dose and the number of administrations can be optimized by those skilled in the art in a known manner.

In one or more embodiments, the invention further concerns a method for introducing a coding sequence into a target cell, such as human cell for therapeutic purposes, comprising the introduction of the nucleic acids, promoters, recombinant proteins, and/or expression cassettes according to the present invention into the target cell. Exemplary human target cells can include antigen presenting cells (APCs) such as dendritic cells, macrophages and other non APC'S such as fibroblasts, tumor cells, and so forth.

The invention further relates to a method for producing a peptide, protein and/or virus comprising the infection of a host cell with a recombinant virus according to the present invention, followed by the cultivation of the infected host cell under suitable conditions, and further followed by the isolation and/or enrichment of the peptide and/or protein and/or viruses produced by said host cell. If it is intended to produce, i.e. amplify the virus according to the present invention the cell has to be a cell in which the virus is able to replicate. For poxviruses, in particular MVA, suitable cells are CEF (chicken embryonic fibroblast) or BHK (baby hamster kidney) cells. For avipoxviruses, such as fowlpoxvirus, suitable cells include CEF or CED (chicken embryonic dermal) cells. If it is intended to produce a peptide/protein encoded by the recombinant virus according to the present invention the cell may be any cell that can be infected by the recombinant virus vector and that allows the expression of the virus encoded proteins/peptides.

The invention further relates to a method for producing a peptide, protein and/or virus comprising the transfection of a cell with the expression cassette, a nucleic acid, promoter, recombinant protein, and/or expression cassette DNA according to the present invention, followed by the infection of the cell with a poxvirus. The infected host cell is cultivated under suitable conditions. A further step comprises the isolation and/or enrichment of the peptide and/or protein and/or viruses produced by said host cell. The step of infecting the cells with a poxvirus may be made before or after the step of transfection of the cells.

The invention further relates to cells comprising a nucleic acid, promoter, recombinant protein, and/or expression cassette according to the present invention. In particular the invention relates to cells infected with the recombinant virus according to the present invention.

EXAMPLES

The following examples further illustrate the present invention. It will be understood by a person of skill in the art that the provided examples in no way may be interpreted as limiting the applicability of the technology.

Example 1

Expression of Brachyury in Human DCs Infected with Recombinant Fowlpox Viruses

To identify expression of Brachyury protein, human dendritic cells (DC) were infected with a positive control virus, recombinant MVA comprising Brachyury and TRICOM, at a multiplicity of infection (MOI) of 2.5. Human DCs were also infected with a negative control non-recombinant fowlpox (FPV-WT) or recombinant fowlpox virus strains comprising of a Brachyury expression cassette and TRICOM in accordance with the present disclosure. Each FPV strain, (listed in more detail in Table 1) including FPV-WT, FPV-mBN343A, FPV-mBN344A, and FPV-mBN345A were used to infect DCs with an MOI of 20. FPVBrachyury expression was detected via western blot analysis performed with a rabbit monoclonal anti-Brachyury antibody. The housekeeping protein glyceraldehyde 3-phoshate dehyrdrogenase (GAPDH) was also detected via western blot analysis as a loading control.

TABLE 1

Recombinant fowlpox virus strains comprising a Brachyury expression cassette and TRICOM

| Recombinant FPV strain | Expression Cassette |
|---|---|
| FPV-mBN343A | SEQ ID NO: 74 |
| FPV-mBN344A | SEQ ID NO: 75 |

TABLE 1-continued

Recombinant fowlpox virus strains comprising a Brachyury expression cassette and TRICOM

| Recombinant FPV strain | Expression Cassette |
|---|---|
| FPV-mBN345A | SEQ ID NO: 72 |
| FPV-mBN354A | SEQ ID NO: 76 |
| FPV-mBN355A | SEQ ID NO: 73 |

Results are shown in FIG. 1. Expression of Brachyury was detected with the FPV-mBN343A and FPVmBN345 recombinant FPVs, but was not detected using the FPV-mBN344A recombinant FPV. Brachyury expression was also detected with MVA-Brachyury-TRICOM. Similar loading of samples was demonstrated by GAPDH expression.

Example 2

Expression of Brachyury in Human DCs Infected with Recombinant Fowlpox Viruses

Expression-levels of Brachyury protein were also compared between additional recombinant FPV strains expressing Brachyury with different promoters. Human dendritic cells (DC) were infected with an MOI of 5 of the positive control recombinant MVA comprising Brachyury and TRICOM, and the negative control non-recombinant strain MVA-WT. Human DCs were also infected with a recombinant FPVs comprising of a Brachyury expression cassette and TRICOM in accordance with the present disclosure (e.g., FPV-mBN343A, FPV-mBN344A, FPV-mBN345A, FPV-mBN354A, FPV-mBN355A, See Table 1). Human DCs were additionally infected with a recombinant Fowlpoxvirus (FPV) comprising a Brachyury expression cassette having either a Vaccinia Virus (VV)-40k promoter or a PrS promoter. The non-recombinant FPV-WT strain served as a negative control. All of the FPVs were used at an MOI of 40. Brachyury expression was detected via western blot analysis performed with a rabbit monoclonal anti-Brachyury antibody. GAPDH was also detected as a loading control.

Figure 2:
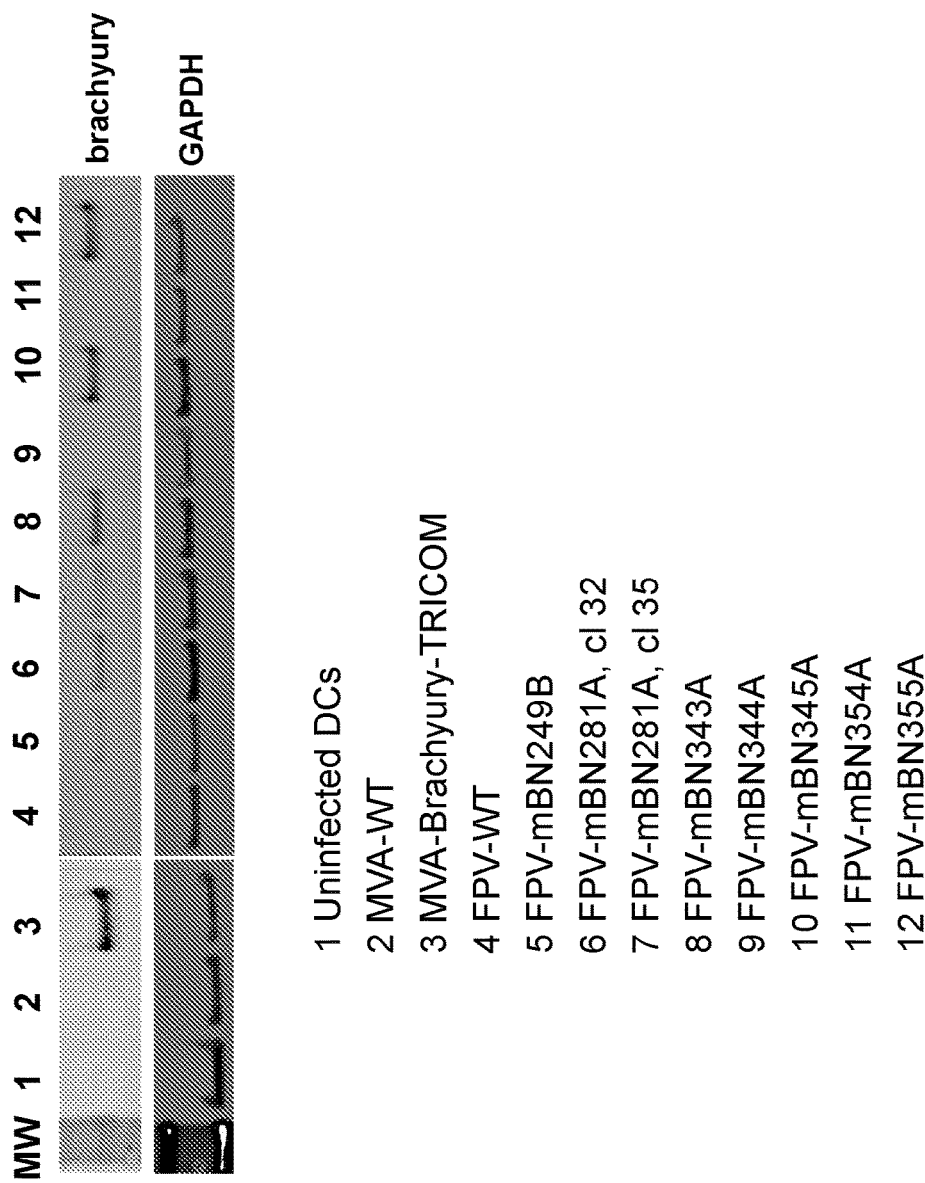
FIG. 2 illustrates expression of the Brachyury protein in human dendritic cells (DCs) infected with non-recombinant viruses MVA-WT or FPV-WT or recombinant viruses MVA-Brachyury-TRICOM, FPV-mBN249B, FPV-mBN281A clone 32, FPV-mBN281A clone 35, FPV-mBN343A, FPV-mBN344A, FPV-mBN345A, FPV-mBN354A, or FPV-mBN355A. A western blot analysis was performed using rabbit monoclonal anti-Brachyury antibody as detailed in Example 2.

Results are shown in FIG. 2. Expression of Brachyury was detected with the FPV-mBN343A and FPV-mBN345A recombinant FPVs, but was not detected using the FPV-mBN344A and FPV-mBN354A recombinant FPV. More particularly, expression of Brachyury was detected at lower levels for the recombinant FPVs having the VV-40k or PrS promoters driving Brachyury (i.e., FVP-mBN281A, FVP-mBN249B). No Brachyury expression was detected in the negative controls (uninfected DCs, MVA-WT, or FPV-WT). Similar loading of samples was demonstrated by GAPDH expression.

The Brachyury expression levels from the Western blot shown in Example 2 were normalized relative to expression of the housekeeping gene GAPDH, which is expected to be expressed at equivalent levels between cells. The intensity of each Brachyury and GAPDH band was measured and a ratio was calculated between the intensity of the Brachyury and GAPDH bands within the same sample.

Figure 3:
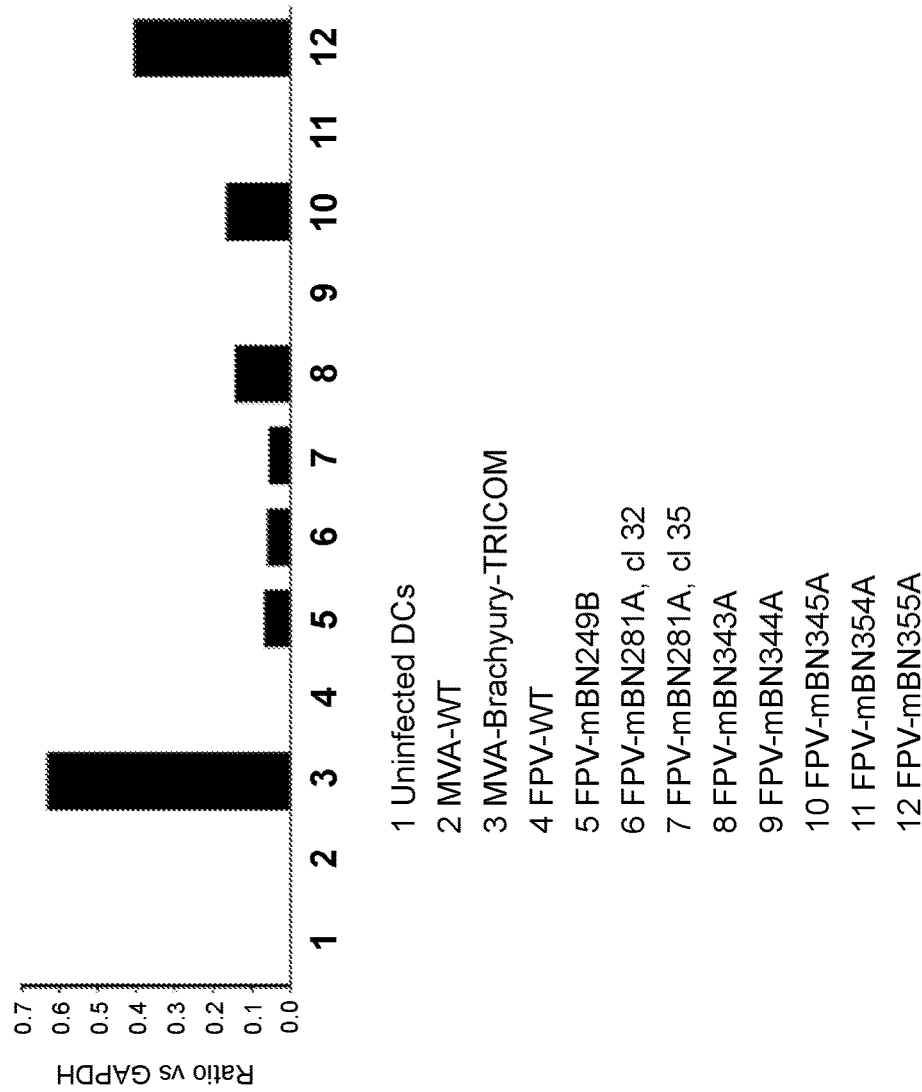
FIG. 3 depicts the relative expression of Brachyury protein compared to GAPDH from western blot analysis of human dendritic cells (DCs) infected with non-recombinant viruses MVA-WT or FPV-WT or recombinant viruses MVA-Brachyury-TRICOM, FPV-mBN249B, FPV-mBN281A clone 32, FPV-mBN281A clone 35, FPV-mBN343A, FPV-mBN344A, FPV-mBN345A, FPV-mBN354A, or FPV-mBN355A, as detailed in Example 2.

Results are shown in FIG. 3. Among the FPV constructs, the highest expression of Brachyury relative to GAPDH was detected in DCs infected with FPV-mBN355A. Moderate relative Brachyury expression was detected in DCs infected with FPV-mBN343A or FPV-mBN345A. The lowest relative Brachyury expression was detected from the recombinant FPVs having the VV-40k or PrS promoters driving Brachyury (i.e., FVP-mBN281A, FVP-mBN249B). Highest relative expression of Brachyury was observed from infection with the positive control virus MVA-Brachyury-TRICOM; no Brachyury expression was detected in the negative control samples. Therefore, among the recombinant FPV strains, superior expression of Brachyury was induced by vectors driving Brachyury expression from the FPV-mBN355, FPV-mBN345, or FPV-mBN344 promoters.

Example 3

Expression of Brachyury and TRICOM in CMMT Cells Infected with Recombinant Fowlpox Viruses Expression of the Brachyury and TRICOM proteins was also assessed by flow cytometry using fluorescently labeled antibodies specific for each protein. CMMT cells (a rhesus macaque mammary tumor cell line) were infected with the positive control recombinant MVA comprising Brachyury and TRICOM, or with a recombinant FPVs comprising of a Brachyury expression cassette and TRICOM in accordance with the present disclosure (e.g, FPV-mBN343A, FPV-mBN345A), or with the recombinant FPV having the PrS promoter driving Brachyury (FVP-mBN249B). Cells were infected with an MOI below 1, so that a mixture of uninfected and infected cells were analyzed. Uninfected CMMT cells served as a negative control.

FACS samples were acquired on the BD LSRII or Fortessa and analyzed using BD FACSDIVA software (BD Bioscience, San Jose, Calif.) or FlowJo (TreeStar Inc., Ashland, Oreg.).

Figure 4:
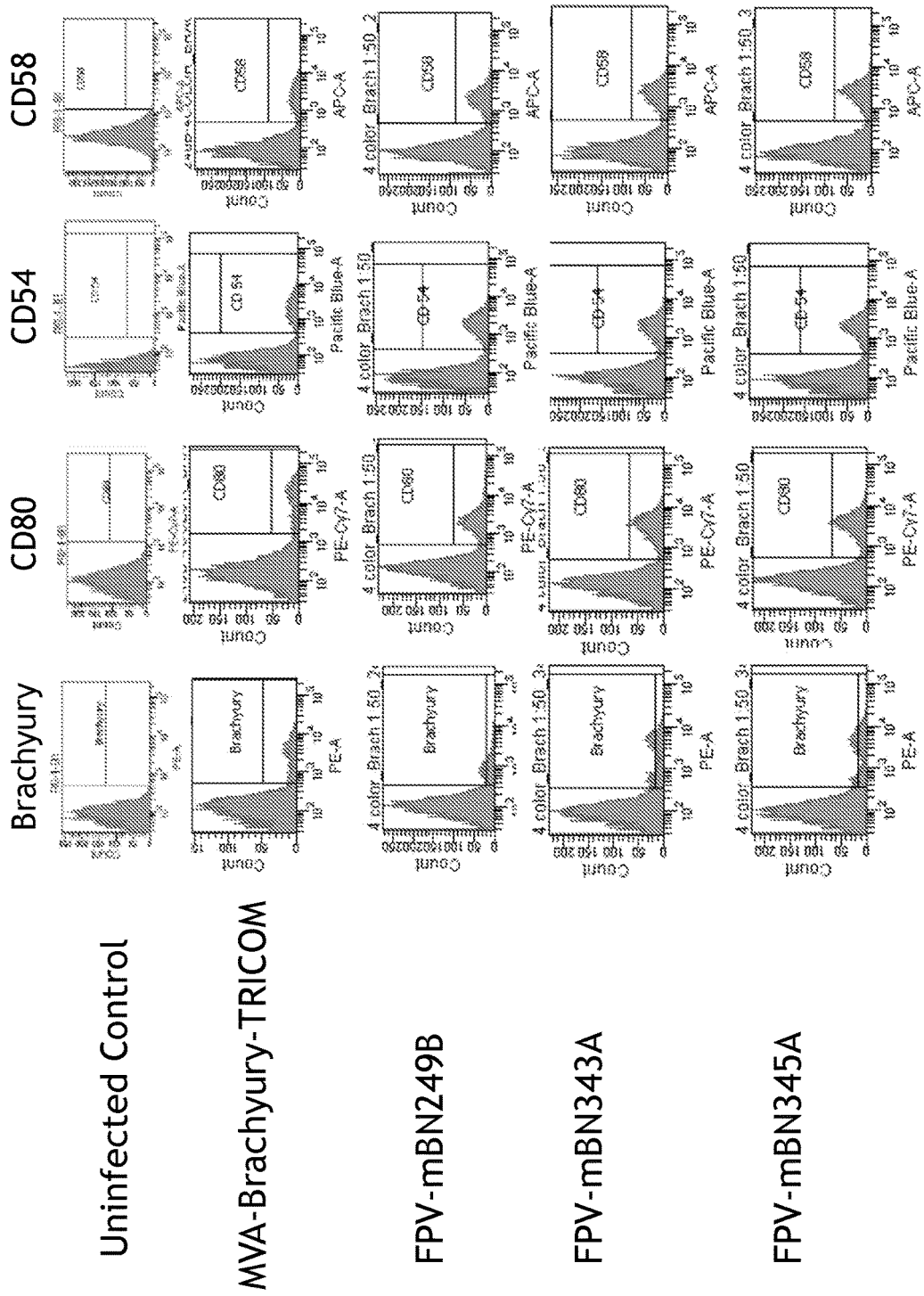
FIG. 4 illustrates expression of Brachyury and TRICOM proteins in CMMT cells (a rhesus macaque mammary tumor cell line) infected with the recombinant viruses MVA-Brachyury-TRICOM, FPV-mBN249B, FPV-mBN343A, or FPV-mBN345A assessed by flow cytometry using fluorescently labeled antibodies specific for each protein, as described in Example 3.

Results are shown in FIG. 4. Histograms of the signals detected for Brachyury and the three TRICOM proteins (CD80, CD54, and CD58) were plotted, and gates were drawn where positive signal was detected (black lines). Among the FPV constructs, the highest expression of Brachyury (shown by the biggest shift in signal along the x-axis) was detected in CMMT cells infected with FPV-mBN343A or FPV-mBN345A. The lowest Brachyury expression was detected from the recombinant FPV with the PrS promoter driving Brachyury (i.e., FVP-mBN281A, FVP-mBN249B). Similar expression levels of the TRICOM proteins were detected among the FPV constructs. Expression of Brachyury and the TRICOM proteins were also observed from infection with the positive control virus MVA-Brachyury-TRICOM.

To quantify the expression level of Brachyury in infected cells the median fluorescence intensity (MFI) was calculated for the Brachyury-positive cells gated in FIG. 4.

Figure 5:
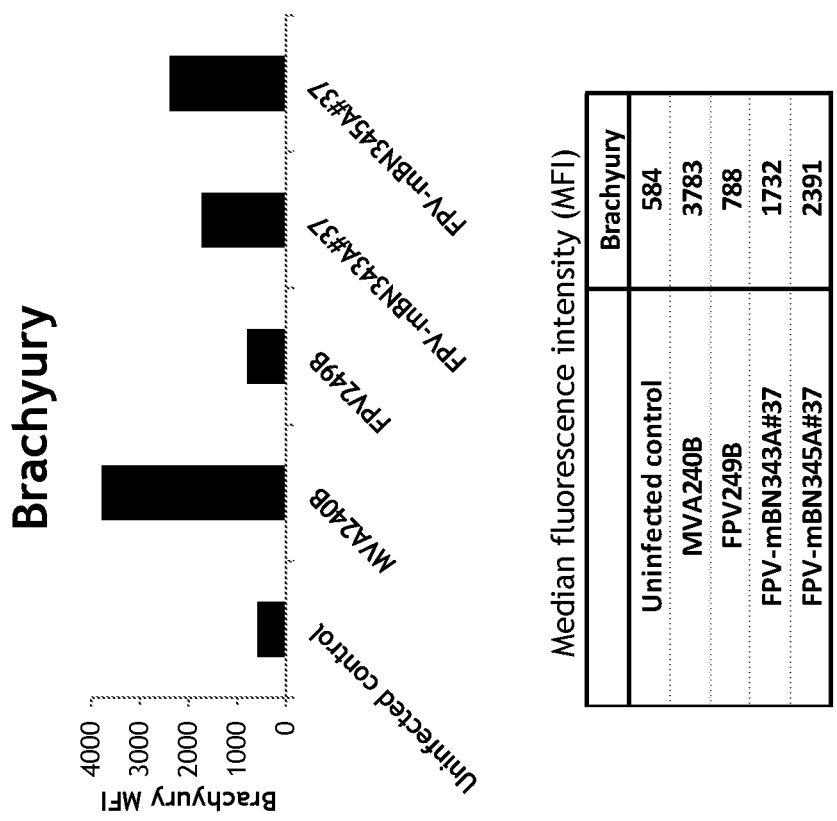
FIG. 5 depicts median expression levels of Brachyury protein in CMMT cells (a rhesus macaque mammary tumor cell line) infected with the recombinant viruses MVA-Brachyury-TRICOM, FPV-mBN249B, FPV-mBN343A, or FPV-mBN345A assessed by flow cytometry, as described in Example 3.

Results are shown in FIG. 5. Among the FPV constructs, the highest Brachyury MFI was detected in CMMT cells infected with FPV-mBN343A or FPV-mBN345A. The lowest Brachyury MFI was detected from the recombinant FPV with the PrS promoter driving Brachyury (FVP-mBN249B). The highest Brachyury MFI of all tested constructs was in cells infected with the positive control virus MVA-Brachyury-TRICOM. Therefore, the median expression level of Brachyury in infected CMMT cells was higher from vectors driving Brachyury expression from the FPV-mBN345 or FPV-mBN344 promoters than from the PrS promoter.

Example 4

Expression of Brachyury from FPV-mBN345B

The drug selection cassette used to initially generate the recombinant FPV-mBN345A strain was removed to generate a recombinant vector suitable for clinical development. This was accomplished by passaging the virus on chicken embryonic fibroblast (CEF) cells without drug selection, plaque purifying individual clones, and identifying clones lacking the selection cassette by PCR and DNA sequencing. This resulted in generation of FPV-mBN345B which comprises of a Brachyury expression cassette driven by the I3+15aa promoter and TRICOM, but does not contain the drug selection cassette.

Expression of Brachyury and the TRICOM proteins from FPV-mBN345B was confirmed in CMMT cells by infecting them with FPV-BN345B at an MOI of 0.625 to infect a subset of cells, or of 40 to infect all cells.

Results are shown in FIG. 6. Histograms of the signals detected for Brachyury and the three TRICOM proteins (CD80, CD54, and CD58) were plotted with a red lines for samples infected with an MOI of 0.625 and blue lines for samples infected with an MOI of 40. Uninfected cells served as a negative control (black lines). At the MOI of 0.625, expression of Brachyury and the three TRICOM proteins was detected as a peak shifted to the right of the taller peak from uninfected cells. At the MOI of 40, expression of Brachyury and TRICOM was detected in all cells as a peak shifted to the right of the uninfected cells.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An expression cassette comprising the nucleic acid sequence of SEQ ID NO:6 operably linked to a nucleic acid sequence encoding a Brachyury antigen, wherein the expression cassette encodes a fusion protein comprising a FPV 088 antigen and said Brachyury antigen.

2. The expression cassette of claim 1, wherein the expression cassette comprises: the nucleic acid sequence of SEQ ID NO:7; the nucleic acid sequence of SEQ ID NO:8; or the nucleic acid sequence of SEQ ID NO:9.

3. The expression cassette of claim 1, wherein the sequence encoding said Brachyury antigen is the nucleic acid sequence of SEQ ID NO: 12.

4. The expression cassette of claim 1, wherein the fusion protein comprises the amino acid sequence of SEQ ID NO: 23.

5. An expression cassette comprising the nucleic acid sequence of SEQ ID NO: 72.

6. An expression cassette comprising the nucleic acid sequence of SEQ ID NO:73.

7. A fowlpox viral vector comprising the expression cassette of claim 1.

* * * * *